US012781200B2

(12) United States Patent
Vyas et al.

(10) Patent No.: US 12,781,200 B2

(45) Date of Patent: Nov. 3, 2026

(54) RETINOID PRODUCTION

(71) Applicant: DSM IP ASSETS B.V., Heerlen (NL)

(72) Inventors: Valmik Kanubhai Vyas, Winchester, MA (US); Peter Louis Houston, Boston, MA (US); Jenna McMahon, Tewksbury, MA (US); René Marcel De Jong, Amsterdam (NL)

(73) Assignee: DSM IP ASSETS B.V., Heerlen (NL)

(*) Notice: Subject to any disclaimer, the term of this patent is extended or adjusted under 35 U.S.C. 154(b) by 265 days.

(21) Appl. No.: 18/700,931

(22) PCT Filed: Oct. 19, 2022

(86) PCT No.: PCT/EP2022/079143
§ 371 (c)(1),
(2) Date: Apr. 12, 2024

(87) PCT Pub. No.: WO2023/067030
PCT Pub. Date: Apr. 27, 2023

(65) Prior Publication Data

US 2025/0002873 A1 Jan. 2, 2025

Related U.S. Application Data

(60) Provisional application No. 63/257,222, filed on Oct. 19, 2021.

(30) Foreign Application Priority Data

Oct. 26, 2021 (EP) .................................... 21204854

(51) Int. Cl.
*C12N 9/04* (2006.01)
*C12P 7/22* (2006.01)

(52) U.S. Cl.
CPC .............. *C12N 9/0006* (2013.01); *C12P 7/22* (2013.01); *C12Y 101/01105* (2013.01)

(58) Field of Classification Search
CPC ....... C12N 9/0004; C12N 9/0006; C12P 7/62; C12P 23/00
See application file for complete search history.

(56) References Cited

U.S. PATENT DOCUMENTS

2020/0248151 A1* 8/2020 Balch ................... C12N 9/0006

FOREIGN PATENT DOCUMENTS

WO 2006102342 A2 9/2006
WO 2008042338 A2 4/2008
WO 2014096992 A1 6/2014
WO 2016172282 A1 10/2016
WO 2019057999 A1 3/2019
WO 2019058000 A1 3/2019
WO 2019058001 A1 3/2019
WO 2020141168 A1 7/2020
WO 2021009194 A1 1/2021
WO 2021136689 A1 7/2021

OTHER PUBLICATIONS

Ausubel et al., Current Protocols in Molecular Biology, https://currentprotocols.onlinelibrary.wiley.com/loi/19343647/year/1998, 5 pages, 1998.
cancer.gov, https://www.cancer.gov/publications/dictionaries/cancer-drug/def/retinyl-acetate?redirect=true, 1 page.
Dujon et al., Genome evolution in yeasts, Nature, vol. 430, pp. 35-44, Jul. 1, 2024.
Magnan et al, Oxidoreductase from Yarrowia lipolytica, 100% identical to SEQ ID No. 1, Database accession No. AOA136PN15, 1 page, 2017, Database UniProt [Online].
Needleman et al., A General Method Applicable to the Search for Similarities in the Amino Acid Sequence of Two Proteins, J. Mol. Biol. No. 48, pp. 443-453, 1970.
Prosite, Scan Prosite, https://prosite.expasy.org/scanprosite/scanprosite_doc.html, 8 pages.
Rice et al., Emboss: The European Molecular Biology Open Software Suite, TIG, vol. 16, No. 6, 2 pages, Jun. 2000.
Riley, Oxidoreductase from Wickerhamomyces anomalus, Database accession No. AOA1E3P885, 100% identical to SEQ ID No. 4, 1 page, 2016, Database UniProt [Online].
Sambrook et al., Molecular Cloning, A Laboratory Manual, Second Edition, 30 pages, 1989.
Schneider et al., Retinol Dehydrogenase 14 from Wickerhamomyces ciferrii NRRL Y—1031 F—60—10, Database UniProt, SEQ ID No. 4, Database accession No. KOKP86, 1 page, 2012.
Zeiner et al., Retinol Dehydrogenase C12R 12 from Alternaria alternata, 36.4% identical to SEQ ID No. Database accession No. AOA177DTJO, 1 page, 2016, Database UniProt.
International Search Report for PCT/EP2022/079143 mailed Mar. 1, 2022, 6 pages.
Written Opinion of the ISA for PCT/EP2022/079143 mailed Mar. 1, 2022, 6 pages.

* cited by examiner

*Primary Examiner* — Tekchand Saidha
(74) *Attorney, Agent, or Firm* — Nixon & Vanderhye, PC

(57) ABSTRACT

The present invention is related to bio-production of retinoids with improved purity profile, particularly bio-retinoids with a high percentage of retinyl acetate, wherein the flux towards retinol is increased and wherein the percentage of unwanted by-products such as dihydroretinoids or retinal is minimized to a range of below 10% by expressing retinol dehydrogenase (EC 1.1.1.105, RDH22) derived from *Yarrowia lipolytica* (*Candida lipolytica*) or *Wickerhamomyces anomalus* (*Hanensula anomala*).

15 Claims, No Drawings

Specification includes a Sequence Listing.

SEQUENCE LISTING

```
Sequence total quantity: 12
SEQ ID NO: 1            moltype = AA  length = 323
FEATURE                 Location/Qualifiers
source                  1..323
                        mol_type = protein
                        organism = Yarrowia lipolytica
SEQUENCE: 1
MTRSKFTEYK QVLRNSCVGK PQYTEKDYPD LDGKNFLVTG ATGGVGLEAT KLLLEKKSHV  60
IMVGRSKTKS QSTLDELQKT YSHGTFDFVE ADLSDLTTVE RAGEYIRSKY TTLDGAILNA  120
GVMAPPYSLT PQGHESQWGI NVVAHFLLSK YISPALISAA QTAPKDTVRL VWVSSSVVAM  180
SPYEGGIKFD DINHSKVKNP SPWTLYSQSK IGDAYLAYLW SKHHPDSGVL SVSLDPGNLA  240
SDLSRHTSWL SSIKNYVLYP PKYGAYTELS ALLNPSVKNN EHLIPWGIEG HLRQDVDDGR  300
RGKDGEELWQ GLNKDVEGFF KEE                                         323

SEQ ID NO: 2            moltype = DNA  length = 972
FEATURE                 Location/Qualifiers
source                  1..972
                        mol_type = genomic DNA
                        organism = Yarrowia lipolytica
SEQUENCE: 2
atgactcgat ccaagttcac cgaatacaaa caagtgctgc gaaacagctg cgtgggcaag  60
ccccaataca ccgagaagga ttaccctgat ctcgacggaa agaactttct tgtcactgga  120
gccactggag gagttggtct ggaggccacc aagctgctgc tagagaagaa gagccatgta  180
atcatggttg gccgatccaa aacaaagtct cagtctaccc ttgacgagct ccagaagaca  240
tactcccacg gtacctttga tttcgtcgag gctgatctgt ctgacctgac cactgtggag  300
cgagccggag agtacattcg aagtaagtac accactttgg acggtgccat tctcaacgct  360
ggagtcatgg ctcccccta tagcctcact ccccagggcc acgagtctca atggggtatc  420
aatgtggttg cccattttct gctgtccaag tatatctctc ctgctctgat ctcggccgcc  480
cagacagccc ccaaggacac cgtgcgactt gtctgggtgt cttcttctgt cgttgccatg  540
agtccttatg aaggaggtat caagtttgac gatatcaacc actctaaggt caagaaccct  600
tctccctgga ccctttactc ccagtccaag attggagatg cttacctggc ttacctgtgg  660
tcgaaacacc atcccgattc tggcgtcctg tccgtctctc tggaccccgg taacctggcc  720
tctgatctgt ccagacatac ttcttggctc tccagcatta agaactacgt gctgtatcct  780
cccaagtatg gcgcctacac cgagctgtct gctctgctga acccctccgt caagaataac  840
gagcatctca ttccctgggg tattgaggga caccttagac aggatgtcga cgatggacga  900
cgtggaaagg acggagaaga gctctggcag ggtctcaaca aggatgtcga gggcttcttt  960
aaggaggagt aa                                                     972

SEQ ID NO: 3            moltype = DNA  length = 972
FEATURE                 Location/Qualifiers
misc_feature            1..972
                        note = codon-optimized for expression in Y. lipolytica
source                  1..972
                        mol_type = other DNA
                        organism = synthetic construct
SEQUENCE: 3
atgacccgat ccaagttcac cgagtacaag caggttctcc gaaactcttg tgttggcaag  60
ccccagtaca ctgagaagga ttaccccgat ctcgacggaa agaactttct cgtcactggt  120
gctactggtg gagttggtct ggaggccact aagctgctcc ttgagaagaa gtctcacgtt  180
attatggttg gccgatctaa gactaagtct cagtctaccc ttgacgagct tcagaagact  240
tactctcacg gtactttcga tttcgttgag gctgatctct ctgaccttac cactgttgag  300
cgagccggag agtacattcg atctaagtac actacccttg acggtgccat tcttaacgct  360
ggagtcatgg ctcccccta ctctctcact ccccagggtc acgagtctca gtggggtatt  420
aacgttgttg ctcactttct cctgtctaag tacatctctc ctgctctgat ttctgctgct  480
cagactgccc ccaaggacac cgttcgactt gtttgggtgt cttcttctgt cgttgccatg  540
tctccttacg agggaggtat taagtttgac gatattaacc actctaaggt caagaaccct  600
tctccttgga ccctttactc tcagtctaag attggtgatg cttacctggc ttacctttgg  660
tctaagcacc accccgattc tggagtcctt tctgtctctc tggaccccgg taacctggct  720
tctgatctct ctcgacacac ttcttggctt tcttctatta agaactacgt tctttaccct  780
cccaagtacg gtgcctacac tgagctgtct gctcttctca acccttccgt taagaacaac  840
gagcacctta ttccctgggg tattgaggga caccttcgac aggatgtcga cgatggtcga  900
cgaggaaagg acggagagga gctctggcag ggtcttaaca aggatgtcga gggtttcttt  960
aaggaggagt aa                                                     972

SEQ ID NO: 4            moltype = AA  length = 319
FEATURE                 Location/Qualifiers
source                  1..319
                        mol_type = protein
                        organism = Wickerhamomyces anomalus
SEQUENCE: 4
MVNVAYEWLR DCWPPKPEFL PKDYPDLTGK TILITGANTG IGFESAKALL KKNATVVFAN  60
RSEEKTKIAI AKIQAELGGD SSQRSIFVKT DLSDLSSIKG TAEELKSKGI TKLHYTILNA  120
GVMQPPKGSK TKQGFELQIG TNVLGHQLLQ KFLTPLVLNA VSSDFTPRVV WLASAAHLSS  180
PPNGGIDWDS FRNADWAGTV SAYGQSKTGN IYQAYIYAQQ HKDVISVSAH PGYLASDLTR  240
AYKGYLQYLM KLLMSPPVYG SYTELFAALS PKVTLKESGR YIGPWGQFRE LRDDVQEGLT  300
DGTAQKLWDW AEAEIRPYT                                              319

SEQ ID NO: 5            moltype = DNA  length = 960
```

```
FEATURE                Location/Qualifiers
source                 1..960
                       mol_type = genomic DNA
                       organism = Wickerhamomyces anomalus
SEQUENCE: 5
atggttaacg ttgcttatga atggctaaga gactgctggc ctcctaaacc tgaattctta  60
ccaaaagatt atccagattt aacaggaaag acaatcttaa tcactggtgc caatacgggt  120
attgggtttg aaagtgctaa agccttgttg aagaaaaacg caacagttgt atttgcaaat  180
agaagcgaag agaagacaaa aatcgctatt gccaaaattc aagctgaatt aggtggtgat  240
tcatctcaaa gatcaatttt cgtcaagact gatttaagtg atttatcatc gatcaagggc  300
acagcggaag aattgaaatc aaaaggtatc acaaaattac attacaccat attgaatgct  360
ggtgttatgc aacctccaaa aggttccaag acaaaacaag gatttgaatt acaaattggt  420
acaaatgttt taggtcatca attattacaa aaatttctaa caccattagt tttgaatgca  480
gtttcatcag atttcacacc aagagttgtt tggttagcct cagctgcaca tctttcatcc  540
ccaccaaatg gtggtattga ttgggattcc ttccgtaatg ctgattgggc tggaactgtc  600
agtgcttatg gtcaatccaa gactggtaat atttatcaag cttatatcta tgctcagcaa  660
cataaagatg tcatcagtgt ctctgctcat ccagggtatt tggcttctga tttaacaaga  720
gcttataaag gttatcttca atatttgatg aaactcttga tgtctcctcc agtttatggt  780
tcttatactg aattattcgc tgctctcagt ccaaaagtta cattgaagga aagtggtaga  840
tatattggtc cttggggtca attcagagaa ttgagagatg atgttcaaga aggcttaact  900
gatggaactg ctcaaaaatt atgggattgg gctgaagctg aaattagacc atacacttag  960

SEQ ID NO: 6           moltype = DNA  length = 960
FEATURE                Location/Qualifiers
misc_feature           1..960
                       note = codon-optimized for expression in Y. lipolytica
source                 1..960
                       mol_type = other DNA
                       organism = synthetic construct
SEQUENCE: 6
atggttaacg ttgcttacga gtggcttcga gactgctggc cccctaagcc tgagttcctc  60
cctaaggatt accctgacct caccggaaag accatcctta tcactggtgc caacactggt  120
attggttttg agtccgctaa ggctctcctc aagaagaacg ctaccgttgt ttttgccaac  180
cgatccgagg agaagactaa gatcgctatt gccaagattc aggctgagct tggtggtgat  240
tcttctcagc gatctatttt cgtcaagact gacctttccg atctctcttc cattaagggc  300
actgctgagg agcttaagtc taagggtatc actaagctcc actacaccat tcttaacgct  360
ggtgttatgc agcctcccaa gggctccaag actaagcagg gttttgagct tcagattggt  420
actaacgttc ttggccacca gctcctccag aagtttctca ctccccttgt tctcaacgct  480
gtttcttctg atttcacccc tcgagttgtt tggctcgcct ctgctgctca cctttcttcc  540
cctcccaacg gtggtattga ttgggattcc ttccgaaacg ctgattgggc tggtactgtc  600
tctgcttacg gtcagtctaa gactggtaac atttaccagg cttacatcta cgctcagcag  660
cacaaggatg tcatctctgt ctctgctcac cccggatacc ttgcttctga tctcactcga  720
gcttacaagg gataccttca gtaccttatg aagctcctta tgtctcctcc cgtttacggt  780
tcttacactg agcttttcgc tgctctttct cccaaggtta ctctcaagga gtctggtcga  840
tacattggtc cttggggtca gttccgagag cttcgagatg acgttcagga gggccttacc  900
gatggtactg ctcagaagct ctgggattgg gctgaggctg agattcgacc ttacacttaa  960

SEQ ID NO: 7           moltype = DNA  length = 11606
FEATURE                Location/Qualifiers
misc_feature           1..11606
                       note = expression plasmid
source                 1..11606
                       mol_type = other DNA
                       organism = synthetic construct
SEQUENCE: 7
cgcgtggatc gccggtgcgt tgacgttggt gacctccagc cagaggtgcc cggcgccccg  60
ctcgccggcg aactccgtcg cgagccccat caacgcgcgc ccgaccccgt gcccccggtg  120
ctccggggcg acctcgatgt cctcgacggt cagccggcgg ttccacgccg agtacgagat  180
gaccacgaag cccgccaggt cgccgtcgtc cccgtacgcg acgaacgtcc gggagtccgg  240
gtcgccgtcc tccccgtcgt ccgattcgtc gtccgattcg tcgtcgggga acaccttggt  300
caggggcggg tccaccggca cctcccgcag ggtgaagccg tccccggtgg cggtgacgcg  360
gaagacggtg tcggtggtga aggacccatc cagtgcctcg atggcctcgg cgtcccccgg  420
gacactggtg cggtaccggt aagccgtgtc gtcaagagtg gtcatttttg tgtctaggtg  480
tttgtgtttg gactgcgatc agtgaagaaa agaagaggaa aaattgtgca agaaattttg  540
ctttcaagac ttggctgatg cagcagggta actctgggac acagacctat gtttgtggtt  600
aaactcaatg cacgtggtac gtgcgtggag cgcttaccca tccaagggtg tggacatgga  660
accgacggtc cgtggagttg tgtaatgtca ttttggcgac tcttgaagca aggctataaa  720
aaaattgtgt ggcttgagtc ttatcgagct cggtcactac aagagttaat cttcctgtct  780
caggcagaca ggtcaggcag ggttactttt gggtgtgctg taactcactg tatggccgtt  840
agtgcgcata gacgttgtac atactggacc gaattgtagc gtgctcaata gggccaataa  900
agctattgta gggatccgaa ttttcagaac ctaatttatc tgttacccgg cctgtggctc  960
gcacagctta aaaatggtca aactttcccc ttcttgtctt tttttcctca cattcatcag  1020
gttcttgtct tgatctttca agtgagtatt aattaccgac cttggttctt cattgggaga  1080
gcattggaag ccgtggtgca gcaaccacaa aacggttctt ccccttcgat accttcttgc  1140
ctgcctttca atacaagtcg gctcgattag cggtggtcgc ccccgccagc ggagaacatg  1200
gaactaaccc agaatgagag ctaagtggag aaagaagaga gtcagacgac tcaagcgaaa  1260
gcgccgcaag gtccgagctc gatccaaata agcggttttt aacggagatt taacactaaa  1320
tcgaagaact tttcccgttt catttgcgaa tgagctcgtt aacaaaatcc cccagttttt  1380
ttatccagct gtaaggattg acattagtaa tgaattattg tttggtatat ttaaatctgt  1440
```

-continued

```
agttcctttc tgtccgtgtc ggcaactgtc gtactcgtga tttacttgta ttgacgaata  1500
cttactgtag cgcactctgc tgctactggt cgtaaggatg tgctatttcg gtgtatggtg  1560
ggtttttttgg gggtcggaac cgaagactgt tacacgggca cggctcgttg tgtacacgca  1620
cagagctctt gcgagtcatg ttgtagctag ctcgtcgtgt tcaggaactg ttcgatggtt  1680
cggagagagt cgccgcccag aacatacgcg caccgatgtc agcagacagc cttattacaa  1740
gtatattcaa gcaagtatat ccgtagggtg cgggtgattt ggatctaagg ttcgtactca  1800
acactcacga gcagcttgcc tatgttacat ccttttatca gacataacat aattggagtt  1860
tacttacaca cggggtgtac ctgtatgagc accacctaca attgtagcac tggtacttgt  1920
acaaagaatt tattcgtacg aatcacaggg acggccgccc tcaccgaacc agcgaatacc  1980
tcagcggtcc cctgcagtga ctcaacaaag cgatatgaac atcttgcgat ggtatcctgc  2040
tgatagtttt tactgtacaa acacctgtgt agctccttct agcattttta agttattcac  2100
acctcaaggg gagggataaa ttaaataaat tccaaaagcg aagatcgaga aactaaatta  2160
aaattccaaa aacgaagttg gaacacaacc ccccgaaaaa aaacaacaaa caaaaaaccc  2220
aacaaaataa acaaaaacaa aataaatata taactaccag tatctgacta aaagttcaaa  2280
tactcgtact tacaacaaat agaaatgagc cggccaaaat tctgcagaaa aaaatttcaa  2340
acaagtactg gtataattaa attaaaaaac acatcaaagt atcataacgt tagttatttt  2400
attttattta ataaaagaaa acaacaagat gggctcaaaa ctttcaactt atacgataca  2460
taccaaataa caatttagta tttatctaag tgcttttcgt agataatgga atacaaatgg  2520
atatccagag tatacacatg gatagtatac actgacacga caattctgta tctctttatg  2580
ttaactactg tgaggcatta aatagagctt gatatataaa atgttacatt tcacagtctg  2640
aacttttgca gattacctaa tttggtaaga tattaattat gaactgaaag ttgatggcat  2700
ccctaaattt gatgaaagat gaaattgtaa atgaggtggt aaaagagcta cagtcgtttt  2760
gttttgagat accatcatct ctaacgaaat atctattaaa aatctcagtg tgatcatgag  2820
tcattgccat cctggaaaat gtcatcatgg ctgatatttc taactgttta cttgagataa  2880
atatatattt acaagaactt cccttgaaat taatttagat ataaaatgtt tgcgggcaag  2940
ttactacgag gaataaatta tatctagagg ttccgcttcc tcgctcactg actcgctgcg  3000
ctcggtcgtt cggctgcggc gagcggtatc agctcactca aaggcggtaa tacggttatc  3060
cacagaatca ggggataacg caggaaagaa catgtgagca aaaggccagc aaaaggccag  3120
gaaccgtaaa aaggccgcgt tgctggcgtt tttccatagg ctccgccccc ctgacgagca  3180
tcacaaaaat cgacgctcaa gtcagaggtg gcgaaacccg acaggactat aaagatacca  3240
ggcgtttccc cctggaagct ccctcgtgcg ctctcctgtt ccgaccctgc cgcttaccgg  3300
atacctgtcc gcctttctcc cttcgggaag cgtggcgctt tctcatagct cacgctgtag  3360
gtatctcagt tcggtgtagg tcgttcgctc caagctgggc tgtgtgcacg aaccccccgt  3420
tcagcccgac cgctgcgcct tatccggtaa ctatcgtctt gagtccaacc cggtaagaca  3480
cgacttatcg ccactggcag cagccactgg taacaggatt agcagagcga ggtatgtagg  3540
cggtgctaca gagttcttga agtggtggcc taactacggc tacactagaa ggacagtatt  3600
tggtatctgc gctctgctga agccagttac cttcggaaaa agagttggta gctcttgatc  3660
cggcaaacaa accaccgctg gtagcggtgg tttttttgtt tgcaagcagc agattacgcg  3720
cagaaaaaaa ggatctcaag aagatccttt gatcttttct acggggtctg acgctcagtg  3780
gaacgaaaac tcacgttaag ggattttggt catgagatta tcaaaaagga tcttcaccta  3840
gatcctttta aattaaaaat gaagttttaa atcaatctaa agtatatatg agtaaacttg  3900
gtctgacagt taccaatgct taatcagtga ggcacctatc tcagcgatct gtctatttcg  3960
ttcatccata gttgcctgac tccccgtcgt gtagataact acgatacggg agggcttacc  4020
atctggcccc agtgctgcaa tgataccgcg agacccacgc tcaccggctc cagatttatc  4080
agcaataaac cagccagccg gaagggccga gcgcagaagt ggtcctgcaa ctttatccgc  4140
ctccatccag tctattaatt gttgccggga agctagagta agtagttcgc cagttaatag  4200
tttgcgcaac gttgttgcca ttgctgcagg catcgtggtg tcacgctcgt cgtttggtat  4260
ggcttcattc agctccggtt cccaacgatc aaggcgagtt acatgatccc ccatgttgtg  4320
caaaaaagcg gttagctcct tcggtcctcc gatcgttgtc agaagtaagt tggccgcagt  4380
gttatcactc atggttatgg cagcactgca taattctctt actgtcatgc catccgtaag  4440
atgcttttct gtgactggtg agtactcaac caagtcattc tgagaatagt gtatgcggcg  4500
accgagttgc tcttgcccgg cgtcaacacg ggataatacc gcgccacata gcagaacttt  4560
aaaagtgctc atcattggaa aacgttcttc ggggcgaaaa ctctcaagga tcttaccgct  4620
gttgagatcc agttcgatgt aacccactcg tgcacccaac tgatcttcag catcttttac  4680
tttcaccagc gtttctgggt gagcaaaaac aggaaggcaa aatgccgcaa aaaagggaat  4740
aagggcgaca cggaaatgtt gaatactcat actcttcctt tttcaatatt attgaagcat  4800
ttatcagggt tattgtctca tgagcggata catatttgaa tgtatttaga aaaataaaca  4860
aataggggtt ccgcgcacat ttccccgaaa agtgccacct gacgtctaag aaaccattat  4920
tatcatgaca ttaacctata aaaataggcg tatcacgagg ccctttcgtc tggcctagga  4980
agcgacttcc aatcgctttg catatccagt accacaccca caggcgtttg tgctactcta  5040
ctgatagcaa tagatgcgtc ataattggtt ggcccgctga gcctccacag gatactattg  5100
cacataccct ggtcatgtgc agatcagctc atttgtggag actctggagt aacttagacg  5160
acgcctggtt caattgccgc aatgtgcgcc cacgcagata atgtattgag gggtggagcg  5220
cctcttgggg acttgctgta cttgtacggg atattaaacg cactcagcaa gaccatgacg  5280
taaaacacac ctactgtacg atacgtactg taggtattgt actcgtaccc ggtactacaa  5340
atagtacgat actatacgga gtgtatttgt accttgatat acgactggcg gagtgaagag  5400
aaggagttga acaagaccag atggggatat cagccccagt gctttgtatt acaagtacga  5460
gtacttaata gatactgtaa ggctattgat acggatggca gtaagtcatt gagtaagcaa  5520
ttgtggccca gcatctcccc tacgtacttg taccataccc catggagaca ccaatggtct  5580
ttcacgcaca ctgtcgtgtg ctgtatcgca gaatcgggtg tccaaccaaa tgccgttacc  5640
cccacgtcac agccgataga cagatacacc atcaatacca gcaggttgta tcatgcggtt  5700
ggctgaaggt aagctgattg gtctaaaaac tgtagctgtc ctaattcaac gagcgctatt  5760
tggggccaac cacctcggcc aagcggcctt taatctgcgt gccccagagg cgtctaatga  5820
ggctctggcc gccactgtag gagtgtttct ctgtgcgcac acgcagtttt gagtttgggc  5880
gactttccct ttttcccaat tgcgtacaca cacagctccg agctaagcgc tgtccttgaa  5940
ccttctccct cttttccctc tttttctctt ccccttcccc tcctccacat taaggccaaa  6000
tcctgaattg caccaactag tacaacgaca acaatggaca agaagtactc catcggtttg  6060
gacattggta ctaactctgt cggctgggcc gtcatcaccg acgagtacaa ggttccctcc  6120
aagaagttca aggtccttgg caacaccgac cgacactcta tcaagaagaa cctgatcggt  6180
```

-continued

```
gctctgctgt tcgactctgg cgagactgcc gaggccaccc gactgaagcg aaccgctcga  6240
cgccgataca cccgacgaaa gaaccgaatc tgttacctcc aggagatctt cagcaacgag  6300
atggctaagg tcgacgactc cttcttccac cgactcgagg agtctttcct ggtcgaagag  6360
gataagaagc acgagcgaca ccccatcttc ggcaacattg ttgatgaggt tgcctaccat  6420
gagaagtacc ccaccatcta ccacctccga aagaagctcg tcgactccac tgacaaggct  6480
gacctccgac tcatctacct tgctctcgcc cacatgatca agttccgagg tcacttcctc  6540
attgagggtg atctcaaccc cgacaactcc gacgttgaca agctgttcat ccagctcgtc  6600
cagacctaca accagctctt tgaggagaac cctatcaacg cttctggtgt tgacgccaag  6660
gccattctct ccgcccgact ctctaagtcc cgacgactcg agaacctcat tgcccagctg  6720
cccggcgaga agaagaacgg cctcttcggt aacctgattg ctctctctct tggtctgacc  6780
cccaacttca agtccaactt tgacctcgcc gaggacgcca agctccagct gtccaaggac  6840
acctacgatg acgatctgga caacctcctg gcccagatcg gtgaccagta cgccgatctc  6900
ttccttgccg ccaagaacct ctccgacgcc atcctgctct ccgacatcct ccgagtcaac  6960
accgagatta ccaaggctcc tctgtctgcc tctatgatca agcgatacga cgagcaccac  7020
caggatctca ctcttctcaa ggctctcgtc cgacagcagc tccccgagaa gtacaaggag  7080
atttttcttg accagtccaa gaacggttac gctggctaca ttgacggtgg tgcttcccag  7140
gaagagtttt acaagttcat caagcctatt ctggagaaga tggacggtac cgaggagctg  7200
ctcgtcaagc tcaaccgaga ggacctcctt cgaaagcagc gaaccttcga taacggctcc  7260
atcccccacc agatccacct gggtgagctc cacgccattc tccgaagaca agaggacttc  7320
taccccttcc taaaggataa ccgagagaag atcgagaaga ttctcacctt ccgaatcccc  7380
tactacgtcg gtcccctcgc tcgaggtaac tcccgatttg cttggatgac ccgaaagtcc  7440
gaggagacta tcaccccctg gaactttgaa gaggtagtcg acaagggtgc ctccgcccag  7500
tctttcattg agcggatgac caacttcgat aagaacctcc ccaacgagaa ggtccttccc  7560
aagcactctc tcctctacga gtacttcacc gtctacaacg agctgaccaa ggtcaagtac  7620
gttaccgagg gcatgcgaaa gcccgctttc ctctctggtg agcagaagaa ggccattgtc  7680
gacctcctgt tcaagactaa ccgaaaagtc accgtcaagc agctcaagga agactacttc  7740
aagaagattg agtgcttcga ctccgtcgag atttccggtg tcgaggaccg attcaacgcc  7800
tccctcggca cctaccacga tcttctgaag atcatcaagg acaaggactt tcttgataac  7860
gaggagaacg aggacattct cgaggacatc gtcctcaccc tcaccctttt cgaggatcga  7920
gagatgatcg aggagcgact caagacctac gcccatctct tcgacgacaa ggtcatgaag  7980
caactcaagc gacgacgata cactggctgg ggccgacttt cccgaaagct catcaacggc  8040
atccgagaca agcagtctgg caagaccatc ctggacttcc tgaagtccga cggtttcgcc  8100
aaccgaaact tcatgcagct catccacgac gactctctta ccttcaaaga ggatatccag  8160
aaggcccagg tttctggcca gggcgactcc ctccacgagc acattgccaa cctcgccgga  8220
tcccccgcca tcaaaaaggg tatcctccag accgtcaagg ttgtcgacga actcgtgaag  8280
gtcatgggcc gacacaagcc cgagaacatc gttatcgaga tggcccgaga gaaccagacc  8340
acccagaagg gtcagaagaa ctcccgagag cgaatgaagc gaatcgaaga gggtatcaag  8400
gagctcggtt cccagattct caaggagcac cccgtcgaga acacccagct ccagaacgag  8460
aaactctacc tgtactacct ccagaatggc cgagacatgt acgttgacca ggagctcgac  8520
atcaaccgac tctccgacta cgacgtcgac cacattgttc ctcagtcctt cctcaaggac  8580
gactccatcg acaacaaggt tctgacccga tctgacaaga accgaggtaa gtccgacaac  8640
gttccctccg aagaggtcgt taagaagatg aagaactact ggcgacagct tctcaacgcc  8700
aaactgatca cccagcgaaa gtttgacaac ctcaccaagg ccgagcgagg tggtctgtcc  8760
gagctggaca aggccggctt cattaagcga cagctggtcg agactcgaca gatcaccaag  8820
cacgtcgccc agatcctcga ctcccgaatg aacaccaagt acgacgagaa cgacaagctc  8880
atccgggagg tcaaggtcat caccctgaag tctaagcttg tctccgactt ccgaaaggac  8940
ttccagttct acaaggtccg agagatcaac aactaccacc acgcccacga cgcctacctc  9000
aacgccgttg ttggtaccgc cctcatcaag aagtatccca agctcgagtc cgagttcgtt  9060
tacggcgact acaaggttta cgatgtccga aagatgattg ccaagtccga gcaggagatc  9120
ggtaaggcca ccgccaagta ctttttctac tccaacatca tgaatttctt caagaccgag  9180
atcactctcg ccaacggtga gattcgaaag cgacccctga ttgagactaa tggtgagact  9240
ggtgagatcg tctgggataa gggccgagac ttcgccaccg tccgaaaggt cctgtccatg  9300
ccccaggtca acattgtcaa gaagaccgag gtccagaccg gtggcttctc caaggagtcc  9360
attctcccca agcgaaactc cgacaaactc atcgcccgta agaaggactg ggatccgaag  9420
aagtacggtg gtttcgattc tcccaccgtt gcctactccg tcctcgttgt tgctaaagtc  9480
gagaagggta agtctaagaa actcaagtcc gtgaaggagc tactcggtat caccatcatg  9540
gagcgatctt cttttgagaa gaaccccatt gacttcctcg aggccaaggg ttacaaagag  9600
gtcaagaagg acctgattat caagctgccc aagtactccc tctttgagct cgagaacggc  9660
cgaaagcgaa tgctggcttc cgctggtgag ctgcagaagg gcaacgagct cgctctgccc  9720
tccaagtacg tcaacttcct ctacctggcc tcccactacg agaagctcaa gggctccccc  9780
gaggacaacg agcagaagca gctgttcgtt gagcagcaca agcactacct cgacgagatc  9840
atcgagcaga tctccgagtt ctccaagcga gtcatcctcg ctgacgccaa ccttgataag  9900
gttctctctg cttacaacaa gcaccgggac aagcccatcc gagagcaggc cgagaatatc  9960
atccacctct tcactctcac caacctcggc gctcctgctg ccttcaagta cttcgacacc  10020
accattgacc gaaagaggta cacctccacc aaggaagtcc tcgacgccac cctgatccac  10080
cagtccatca ccggcctcta cgaaacccga atcgacctct cccagctcgg cggtgactct  10140
cgagccgacc ccaagaagaa gcgaaaagtc taaatatccg aagatcaaga gcgaagcaag  10200
ttgtaagtcc aggacatgtt tcccgcccac gcgagtgatt tataacacct ctctttttttg  10260
acacccgctc gccttgaaat tcatgtcaca taaattatag tcaacgacgt ttgaataact  10320
tgtcttgtag ttcgatgatg atcatatgat tacattaata gtaattactg tatttgatat  10380
atatactaat tacaatagta catattagaa catacaatag ttagtgccgt gaagtggctt  10440
aaaataccgc gagtcgatta cgtaatatta ttacctcttg cccatcgaac gtacaagtac  10500
tcctctgttc tctccttcct ttgctttgtg cacgaagaac tgcggtcagg tgacacaact  10560
ttttccatct cagggtgtgt cgcgtgtgct tcatccaaac tttagttggg gttcgggttc  10620
gcgcgagatg atcacgtgcc ctgatttggt gtcgtccccc gtcgcgctgc gcacgtgatt  10680
tatttatttc cggtggctgc tgtctacgcg gggccttctc tgcccttctg tttcaacctt  10740
cgggcggttc tcgtaaccag cagtagcaat ccatttcgaa actcaaagag ctaaaaacgt  10800
taaacctcag cagtcgctcg acgaatgggc tgcggttggg aagcccacga ggcctatagc  10860
cagagcctcg agttgacagg agcccagacg cctttttccaa cggcaacttt tatataaaat  10920
```

```
ggcaatgtat tcatgcaatt gcggccgtgt caggttggag acactggacc acactctcca  10980
ttgcttcctg aggagatgga tcattgctag tgcatctacg cgcagcaatc ccgcaagctc  11040
gacaaccgta gatgggcttt ggtgggccaa tcaattacgc aacccgcacg ttaaattgta  11100
tgaggaagga aggccacggt acaaagtggg tggtcttcac ccagtggttg ttggtggcgt  11160
catgcagacc atggccgcca gtgtgctgga attgaatatt taccgttcgt ataatgtatg  11220
ctatacgaag ttataccggt ctcgtagtgt tcacgttcag ttcacggtga gcttaaaact  11280
atcttcaaga agagatttga gacctgattt atacttgcag caatgtttac ttcttatcgc  11340
gatacacgaa tgtgatacgg atcaaagtaa gcaggactac gataagataa cgaatgcggt  11400
gcagtccatg tcgattaggt atagatacat ttattttgtg ttatgttaca ttttgggggg  11460
atactgtcct acttgtagta cctacttgta gtggcgcgtt aggggcaggg catgctcatg  11520
tagagcgcct gccgctcgcc gtccgaggcg gtgccgtcgt acagggcggt gtccaggccg  11580
cagagggtga accccatccg ccggta                                       11606

SEQ ID NO: 8           moltype = DNA  length = 14006
FEATURE                Location/Qualifiers
misc_feature           1..14006
                       note = expression plasmid
source                 1..14006
                       mol_type = other DNA
                       organism = synthetic construct
SEQUENCE: 8
gcggagccta ggccggccag cgtggcgcgt ggccatattg gccagcagct tactacagct  60
cagccaaagt ggatcatgat ggacggaaat atcggactgg aggccaaaaa ggaggtgctc  120
aaatacgcac gggacaagtc tgcacaggtg gcattcgaac ccacgtctgt ccccaaagcc  180
gctgctcttt ccgagctcaa tctgcccgtt taccccaaca actccattgc cttagccacc  240
cccaacactg cagagctcga ggccatgttc gaggcattcc acgagaaggg ccgatttgac  300
gttgacgact ggtttccagt catagacggt cttgctctcg gagctgactt tagaaacgga  360
gccaccatgt tgtcgcacca acatcgtgga ctcaaagcta ttctcgaaca aggaactctg  420
gcccaggcaa tccacatgct accatacatc ccaactttga tcatcaaggg cggagccaac  480
ggcgtcgtcg tcttccaact cattgatgat atcgagtctg ccattcattc acagcgttct  540
gcttccaata aaacgcctgg cctgttccag aagggcaacg ctgcgagtgg aaacaccaag  600
gtcggcgtct acatgcagta ctttgagccc gaagaagtgg gcagtcagtc gattgtaagc  660
gtgactggag ctggagacac tctgtttgga accctggcca tggagattgt caaggacgag  720
tcctggttga acgatatggg agacaagaag agtgcagttg tttctcgagc catgaacaat  780
gctgtgaaga ctattcagag taaggacgct gtctgcaaga gcatccttta agtgatttgc  840
catgctttct cttcttccac gatgtaaata cttattttac acactactgt gcagtagcaa  900
atacagaaca agagttgtcg cctattgaca gtacagtacg agtagtgtat gtacagtagt  960
tatacaatat ctatgtgaaa ttcgtcggca gctttcggct gatgaactac gagttcttcg  1020
taataaatca tcaacgtaat aagcttggta ccagagacgg gttggcggcg tatttgtgtc  1080
ccaaaaaaca gccccaattg ccccaattga ccccaaattg acccagtagc gggcccaacc  1140
ccggcgagag ccccccttcac cccacatatc aaacctcccc cggttcccac acttgccgtt  1200
aagggcgtag ggtactgcag tctggaatct acgcttgttc agactttgta ctagtttctt  1260
tgtctggcca tccgggtaac ccatgccgga cgcaaaatag actactgaaa atttttttgc  1320
tttgtggttg ggactttagc caagggtata aaagaccacc gtccccgaat tacctttcct  1380
cttcttttct ctctctcctt gtcaactcac acccgaaatc gttaagcatt tccttctgag  1440
tataagaatc attcgctagc cacaaaaaatg ggtgatctcg atgcccgagg aacctctgct  1500
caccccgagc tctctgagcg accttctatt atgccttcta tgtctgatat tcaggaccct  1560
tctggtgatg acaaggctac tccccgagga tctgctgctg gtctgcccca gcttgagctt  1620
gctggacacg cccgacgact tggccacctt gagaacttct ttgctgtcca ggctcgacag  1680
cagatttact cttctttgc tgttttttgt gagtttgaca ctgcttgttc tctcgctcag  1740
cttgcttctg ctgtgcgaaa cgtttgtctt tctaaccccc ttctccttca cactgttgag  1800
cctaagcacc ctgacatcgc tggattctac cactctgacg agtacctttc ccgaccttgg  1860
cctcagcacg attacatgcg agttcttcga gaggttcacg tcgctgacgt tgttatgaac  1920
ggacagaagg agcacgctca cgttgttcga gatgctgttg acgtttttca ggctcacgga  1980
aaccaggtta cttctgagct ccttgagctt atgactcaga ttgagattcc tcacgcttct  2040
cagactcgac cctcttggcg acttctctgt tttccccacg gagaggctaa ccgatggcga  2100
acctttgctt ttgtttctaa ccactgttct tctgatggtc tttctggtct taacttcttt  2160
cgagatctcc agaaggagct tgctcacggc cccacctctg gtgctcctgg tgcccccgga  2220
gcttccggag ttattttcga ttacgctcag gacgctgcta ccctgcccaa gctgcccccct  2280
cccattgatc agaagctcga ttaccgacct tctaagaagg ctcttctcgg ccttctcgct  2340
ggcaagttcg ttcgagagaa gctcggttac gtttctgctg ctcctcccac taccctacc  2400
tctgaccttg ctcaccctga gggtcaccag tactactgtt accttgttaa cgttcccact  2460
tcttctgttg cccacattaa gactcaggtg cgagagaacg ttcctcacaa gtgtactctc  2520
actccctttc tccaggcttg ttggcttgtt tctctgttca agtacggtcg agttttttct  2580
ggttcttggc ttgagcgata caccgatgtt cttgttgcta tgaacactcg acagcttctc  2640
cccgaggacc ttgagcttca gcgacagtac cgatacggtt ctaacattgg agctgttcga  2700
tacaactacc ctattgctcc ccttgacgtt cgagataacg atcagaagtt ctggtccctt  2760
gttgagtctt accgacttgc cctttctgat gcccgagata agaacgatta cctttacgct  2820
cttggtgctc ttatgctccc tgagatttac gagaagaaga acgttgatgc tgttgttaac  2880
gataccattc ttaaccagcg acgacaggga acccttcttt ctaacgttgg ttacgttcga  2940
gatgagcagc ccactgcttt tgctattaag aaccacgttt tttctcaggg agttggagct  3000
aaccgaaacg cttttgttct taacatttgt gctaccgatc agggtggtct taacatcgct  3060
atttctattg ctaagggaac ccttgcttct cgacaggagg gacaggagct ttgtgatatt  3120
tttaagtcta ctctccttcg attttaaacg cgtctatccg aagatcaaga gcgaagcaag  3180
ttgtaagtcc aggacatgtt tcccgcccac gcgagtgatt tataacacct ctcttttttg  3240
acacccgctc gccttgaaat tcatgtcaca taaattatag tcaacgacgt ttgaataact  3300
tgtcttgtag ttcgatgatg atcatatgat tacattaata gtaattactg tatctgtacc  3360
tgctgtggac cacgcacggc ggaacgtacc gtacaaatat tttcttgctc acatgactct  3420
ctctcggccg cgcacgccgg tggcaaattg ctcttgcatt ggctctgtct ctagacgtcc  3480
```

```
aaaccgtcca aagtggcagg gtgacgtgat gcgacgcacg aaggagatgg cccggtggcg  3540
aggaaccgga cacggcgagc cggcgggaaa aaaggcggaa aacgaaaagc gaagggcaca  3600
atctgacggt gcggctgcca ccaacccaag gaggctattt tgggtcgctt tccatttcac  3660
attcgccctc aatggccact ttgcggtggt gaacatggtt tctgaaacaa ccccccagaa  3720
ttagagtata ttgatgtgtt taagattggg ttgctatttg gccattgtgg gggagggtag  3780
cgacgtggag gacattccag ggcgaattga gcctagaaag tggtaccatt ccaaccgtct  3840
cagtcgtccg aattgatcgc tataactatc acctctctca catgtctact tccccaacca  3900
acatccccaa cctcccccac actaaagttc acgccaataa tgtaggcact ctttctgggt  3960
gtgggacagc agagcaatac ggaggggaga ttacacaacg agccacaatt ggggagatgg  4020
tagccatctc actcgacccg tcgacttttg gcaacgctca attacccacc aaatttgggc  4080
tggagttgag gggaccgtgt tccagcgctg taggaccagc aacacacacg gtatcaacag  4140
caaccaacgc ccccgctaat gcacccagta ctgcgcaggt gtgggccagg tgcgttccag  4200
atgcgagttg gcgaacccta agccgacagt gtactttttg ggacgggcag tagcaatcgt  4260
gggcgtagac cccggtgtat ataaaggggt ggagaggacg gattattagc accaacacac  4320
acacttatac tacatgctag ccacaaaaat gctctctttc ttctggcgaa acggtatcga  4380
gactcccgag cccctcaagg ctgacgtttc cggctctatc cctccctggc ttcagggaac  4440
ccttctccga aacggtcctg gtctgttctc cgttggcaac acttcctaca agcactggtt  4500
cgatggtatg gctctcattc actccttcac ctttaaggat ggtgaggttt tttaccgatc  4560
taagtacctg aagtctgaga cttacaagaa gaacatcgct gccgaccgaa tcgttgtgtc  4620
tgagttcgga accatggtgt accccgatcc ctgcaagaac attttctccc gagccttctc  4680
ttacatgatg aacgccattc ctgactttac cgataacaac ctcattaaca tcattaagta  4740
cggtgaggat tactacgcct cctctgaggt caactacatc aaccagattg acccccctgac  4800
ccttgagact ctcggacgaa ctaactaccg aaaccacatt gccatcaacc ttgccactgc  4860
tcaccctcac tacgacgagg agggtaacac ttacaacatg ggcactgcta ttatgaacct  4920
cggtcgaccc aagtacgtga ttttcaaggt gcccgccaac acctctgata aggagaacaa  4980
gaagcctgcc ctctctgagg tggagcaggt ttgctccatt cccatccgac cctcccttta  5040
cccttcttac ttccactctt ttggcatgac tgagaactac atcatcttcg ttgagcaggc  5100
cttcaagctg gacatcgtca agctggctac tgcttacttc cgagatatta actggggatc  5160
ttgccttaag ttcgaccagg atgacattaa cgtgttccac ctggtcaaca agaagactgg  5220
taaggctgtg tccgtgaagt actacactga ccccttttgtt accttccacc acatcaacgc  5280
ttacgaggac gatggccacg tcgtcttcga tctcattact tacaaggact ctaagctgta  5340
cgatatgttc tacattcaga acatgaagca ggacgtcaag cgatttattg agactaacaa  5400
ggacttcgct cagcccgtgt gccagcgatt tgtccttccc gtcaacgttg ataaggagac  5460
tcctcaggac atcaaccttg tcaagctgca ggacaccact gccactgctg tcctgaagga  5520
ggacggctct gtctactgca cccctgacat catttttaag ggtcttgagc tccctgctat  5580
caactacaag tttaactcta agaagaaccg atacttctac ggcacccgag tggagtggtc  5640
cccttaccct aacaaggtcg ctaaggtgga cgttgttact cgaacccaca agatttggac  5700
tgaggaggag tgttaccctt ctgagcctgt ctttattgcc tcccctgacg ccgttgatga  5760
ggatgacggt gtgattcttt cttctgtggt ttctttcaac ccccagcgac cccctttcct  5820
ggttgtcctc gatgctaagt ccttcaagga gattgctcga gctaccatcg atgcctctat  5880
tcacatggac cttcacggcc ttttcatcca cgacaagtct acctaagttt tttgatcaat  5940
gatccaatgg ctttcacata cccccccacg cctataatta aaacacagag aaatataatc  6000
taacttaata aatattacgg agaatctttc gagtgttcag cagaaatata gccattgtaa  6060
caaaagccgg ctatcgaccg ctttatcgaa gaatatttcc cgccccccag tggccaaacg  6120
atatcggtca gaaggggcag ctctaaacga agaactgcgg tcaggtgaca caactttttc  6180
catctcaggg tgtgtcgcgt gtgcttcatc caaactttag ttggggtttcg ggttcgcgcg  6240
agatgatcac gtgccctgat ttggtgtcgt cccccgtcgc gctgcgcacg tgatttattt  6300
atttccggtg gctgctgtct acgcggggcc ttctctgccc ttctgtttca accttcgggc  6360
ggttctcgta accagcagta gcaatccatt tcgaaactca aagagctaaa aacgttaaac  6420
ctcagcagtc gctcgacgaa tgggctgcgg ttgggaagcc cacgaggcct atagccagag  6480
cctcgagttg acaggagccc agacgccttt tccaacggca acttttatat aaaatggcaa  6540
tgtattcatg caattgcggc cgtgtcaggt tggagacact ggaccacact ctccattgct  6600
tcctgaggag atggatcatt gctagtgcat ctacgcgcag caatcccgca agctcgacaa  6660
ccgtagatgg gctttggtgg gccaatcaat tacgcaaccc gcacgttaaa ttgtatgagg  6720
aaggaaggcc acggtacaaa gtgggtggtc ttcacccagt ggttgttggt ggcgtcatgc  6780
agaccatgca ttggggatag cacagggttg gggtgtcttg tggactcaat gggtgaaagg  6840
agatggaaaa gggcggtgaa aagtggtaga atcgaaatcc ctgacgtcaa tttataaagt  6900
aaaatgcgtt tctgccattt tgctcccctc cttctttcgc aatcgcctcc ccaaaagttg  6960
tcgtggcagt acacatgctt gcatacaatg aagctaatcc ggcttgctca gtagttgcta  7020
tatccaggca tggtgtgaaa cccctcaaag tatatatagg agcggtgagc cccagtctgg  7080
ggtcttttct ctccatctca aaactacttt ctcacatgct agccacaaaa atgaccacta  7140
agtacacttc cgttcacgag tctcccaacg gccctggtga cgctcgaccc accgcttccc  7200
agattatcga cgattacaac cttgagggag agctttctgg caagactgtt ctcgtcaccg  7260
gctgttcctc tggtattggt gttgagactg cccgagctat ttaccgaact ggtgccaccc  7320
tttacctcac tgcccgagat gtcgataagg ccaagaccgt tcttcccgac cttgttgaca  7380
cttcccgagt ccactttctc caccttgacc ttaactctct ggagtctgtt cgaggttttg  7440
ctgagaactt caagtctaag tccactcagc ttcacattct catcgagaac gctggcgtga  7500
tggcctgtcc cgagggccga accgtcgatg gttttgagac tcagtttggt atcaaccacc  7560
ttgctcactt tctcctcttt tacctcctca aggataccct tctcaactct tctacccccg  7620
ctttcaactc ccgagttgtc atcctctctt cttgtgctca ccaggctggt tccgttcacc  7680
ttaacaacct gtctcttgag ggtggatacg agccttggaa gtcttacggc cagtccaaga  7740
ctgccaacct ttggactgcc cgagagatcg agaagcgatt tggtgcttcc ggtatccact  7800
cttgggctgt tcaccccggt tccatcgcta ctgagcttca gcgacacgtt tccgacgagc  7860
ttaagcagaa gtgggctgac gataaggagg gtgccaagct gtggaagtcc accgagcagg  7920
gtgccgccac cactgtcctt gctgctgttt cccctgagct tgagggtaag ggcggtcttt  7980
accttgagga tacccaggtt gccaagcccc ctgcccgagg aatgtttggt gttgctgact  8040
gggcttacga tgaggatggc ccctctaagc tctgggccaa gtctcttgag ctccttaagc  8100
tccagtaaag gttagactat ggatatgtaa tttaactgtg tatatagaga gcgtgcaagt  8160
atggagcgct tgttcagctt gtatgatggt cagacgacct gtctgatcga gtatgtatga  8220
```

```
tactgcacaa cctgtgtatc cgcatgatct gtccaatggg gcatgttgtt gtgtttctcg  8280
atacggagat gctgggtaca agtagctaat acgattgaac tacttatact tatatgaggc  8340
ttgaagaaag ctgacttgtg tatgacttat tctcaactac atccccagtc acaataccac  8400
cactgcacta ccactacaca ctagtggtgt gttctgtgga gcattctcac ttttggtaaa  8460
cgacattgct tcaagtgcag cggaatcaaa aagtataaag tgggcagcga gtatacctgt  8520
acagactgta ggcgataact caatccaatt accccccaca acatgactgg ccaaactgat  8580
ctcaagactt tattgaaatc agcaacaccg attctcaatg aaggcacata cttcttctgc  8640
aacattcact tgacgcctaa agttggtgag aaatggaccg acaagacata ttctgctatc  8700
cacggactgt tgcctgtgtc ggtggctaca atacgtgagt cagaagggct gacggtggtg  8760
gttcccaagg aaaaggtcga cgagtatctg tctgactcgt cattgccgcc tttggagtac  8820
gactccaact atgagtgtgc ttggatcact ttgacgatac attcttcgtt ggaggctgtg  8880
ggtctgacag ctgcgtttc ggcgcggttg gccgacaaca atatcagctg caacgtcatt  8940
gctggctttc atcatgatca catttttgtc ggcaaaggcg acgcccagag agccattgac  9000
gttctttcta atttggaccg atagccgtat agtccagtct atctataagt tcaactaact  9060
cgtaactatt accataacat atacttcact gccccagata aggttccgat aaaaagttct  9120
gcagactaaa tttatttcag tctcctcttc accaccaaaa tgccctccta cgaagctcga  9180
gctaacgtcc acaagtccgc ctttgccgct cgagtgctca agctcgtggc agccaagaaa  9240
accaacctgt gtgcttctct ggatgttacc accaccaagg agctcattga gcttgccgat  9300
aaggtcggac cttatgtgtg catgatcaag acccatatcg acatcattga cgacttcacc  9360
tacgccggca ctgtgctccc cctcaaggaa cttgctctta agcacggttt cttcctgttc  9420
gaggacagaa agttcgcaga tattggcaac actgtcaagc accagtacaa gaacggtgtc  9480
taccgaatcg ccgagtggtc cgatatcacc aacgcccacg gtgtacccgg aaccggaatc  9540
attgctggcc tgcgagctgg tgccgaggaa actgtctctg aacagaagaa ggaggacgtc  9600
tctgactacg agaactccca gtacaaggag ttcctggtcc cctctcccaa cgagaagctg  9660
gccagaggtc tgctcatgct ggccgagctg tcttgcaagg gctctctggc cactggcgag  9720
tactccaagc agaccattga gcttgcccga tccgaccccg agtttgtggt tggcttcatt  9780
gcccagaacc gacctaaggg cgactctgag gactggctta ttctgacccc cggggtgggt  9840
cttgacgaca agggagacgc tctcggacag cagtaccgaa ctgttgagga tgtcatgtct  9900
accggaacgg atatcataat tgtcggccga ggtctgtacg gccagaaccg agatcctatt  9960
gaggaggcca agcgatacca gaaggctggc tgggaggctt accagaagat taactgttag  10020
aggttagact atggatatgt aatttaactg tgtatataga gagcgtgcaa gtatggagcg  10080
cttgttcagc ttgtatgatg gtcagacgac ctgtctgatc gagtatgtat gatactgcac  10140
aacctgtgta tccgcatgat ctgtccaatg gggcatgttg ttgtgtttct cgatacggag  10200
atgctgggta caagtagcta atacgattga actacttata cttatatgag gcttgaagaa  10260
agctgacttg tgtatgactt attctcaact acatccccag tcacaatacc accactgcac  10320
taccactaca cctcgagcat gcacactatt atcacattac tacatccaaa cccctacagg  10380
gggaggagct ctccaatcaa atatgtacat taactatctc tcgtaaatca ttgttataag  10440
accgtccgtg actgtctaaa tcggttcatt cgttgtaaca aatcagtgta acaactcgtg  10500
gtacgcccgg tttgcttcgc tcacgctccc ctagattttc cgtctaggac acaacaagcc  10560
ctggtggatg acgttcaacg ccttcagcgc gtctttttcc tcaataacac acgagatgtt  10620
aatttcgttg gctccctgag aaatcatctc aatgttaata cctgcctggg ccagagtaga  10680
gaagaacatg cctgcacatc cgaccatggc cttcattctc gttccgatca gcgacacaat  10740
ggtcatgcct cgcttcacat ctactgtgcc gtactttcgc agctcctcca cagcctgctt  10800
gaggttggag tcgggagcat ggaaggccat cgacacatgg acctcagaag tggagatgag  10860
atcgacgaca agtttctgct ggtcgagagt agcaaagatc ttgttcaaga agccatgact  10920
cttggttcgc ttattcgaat gaacgttgag aacggtgata ttcgatttgg tagtgacagc  10980
tgtaggcttc ttctcgtcat ctacaggagc agacacctgg ggagtgaatg agccagagga  11040
cagagaagtt agcgagtcgg tggaagaagc cagatcctgg acattgtttt tcgttttcag  11100
gttgcccgag ccgtcagcag atgggtagat gatagttcct cctcccaggg ggtttccac  11160
gtttttgatt cggataggaa tatgggcctt aatgacctgc tccatggtga aggggtggat  11220
gacttcagat ccgtagtagg tcaactcagc ggcctcctcg gggtaatga tgggcagcag  11280
acgggcagtg gacacctttc tgggatcggc agtgaagaca ccatcgactt ctttccagat  11340
ctgaagctcc ttggcgtcca gacccacagc caccagagca gcacacagat cggtgtatcc  11400
tcgtccgatc tggcttagga ggcctccctt gacggggcca aagaaaccgg tcaacacggg  11460
caccatgttt cccttgacag gagcagagtc cgtgttagga gagccgggaa gagtgatgat  11520
ctcgcccaga acacgtccga ggtccgaata gaacttggga tcttcggcat tggtggtggt  11580
aactgcgtga gacaggtcaa agtaccgtgc gttaacacca gcgtcccgca taactgcagt  11640
catgtacatg caactgagct tctccccaat ggccatgatg gagtcgagtg ttcgggggga  11700
gatctcagaa atgatttcag cagcagccag gattcgcaac agctggtcgc actcgccgtt  11760
gatgtcggca ttgaggtttt cgagcagttc ggggttcttg acgtcacgct tagcagctgc  11820
aagatggtct tctcggatag actcaatgat ggggttgtag gcgtctgatc cgagaagagc  11880
agagtcagca gcagcaataa gacgggtggt ggttccctcg gccttggtgg cctctagatg  11940
gcctccttgg ccccattcca gctgcattaa tgaatcggcc aacgcgcggg gagaggcggt  12000
ttgcgtattg ggcgctcttc cgcttcctcg ctcactgact cgctgcgctc ggtcgttcgg  12060
ctgcggcgag cggtatcagc tcactcaaag gcggtaatac ggttatccac agaatcaggg  12120
gataacgcag gaaagaacat gtgagcaaaa ggccagcaaa aggccaggaa ccgtaaaaag  12180
gccgcgttgc tggcgttttt ccataggctc cgcccccctg acgagcatca caaaaatcga  12240
cgctcaagtc agaggtggcg aaacccgaca ggactataaa gataccaggc gtttccccct  12300
ggaagctccc tcgtgcgctc tcctgttccg accctgccgc ttaccggata cctgtccgcc  12360
tttctccctt cgggaagcgt ggcgctttct catagctcac gctgtaggta tctcagttcg  12420
gtgtaggtcg ttcgctccaa gctgggctgt gtgcacgaac cccccgttca gcccgaccgc  12480
tgcgccttat ccggtaacta tcgtcttgag tccaacccgg taagacacga cttatcgcca  12540
ctggcagcag ccactggtaa caggattagc agagcgaggt atgtaggcgg tgctacagag  12600
ttcttgaagt ggtggcctaa ctacggctac actagaagaa cagtatttgg tatctgcgct  12660
ctgctgaagc cagttacctt cggaaaaaga gttggtagct cttgatccgg caaacaaacc  12720
accgctggta gcggtggttt ttttgtttgc aagcagcaga ttacgcgcag aaaaaaagga  12780
tctcaagaag atcctttgat cttttctacg gggtctgacg ctcagtggaa cgaaaactca  12840
cgttaaggga ttttggtcat gagattatca aaaaggatct tcacctagat ccttttaaat  12900
taaaaatgaa gttttaaatc aatctaaagt atatatgagt aaacttggtc tgacagttac  12960
```

```
caatgcttaa tcagtgaggc acctatctca gcgatctgtc tatttcgttc atccatagtt  13020
gcctgactcc ccgtcgtgta gataactacg atacgggagg gcttaccatc tggccccagt  13080
gctgcaatga taccgcgaga gccacgctca ccggctccag atttatcagc aataaaccag  13140
ccagccggaa gggccgagcg cagaagtggt cctgcaactt tatccgcctc catccagtct  13200
attaattgtt gccgggaagc tagagtaagt agttcgccag ttaatagttt gcgcaacgtt  13260
gttgccattg ctacaggcat cgtggtgtca cgctcgtcgt ttggtatggc ttcattcagc  13320
tccggttccc aacgatcaag gcgagttaca tgatccccca tgttgtgcaa aaaagcggtt  13380
agctccttcg gtcctccgat cgttgtcaga agtaagttgg ccgcagtgtt atcactcatg  13440
gttatggcag cactgcataa ttctcttact gtcatgccat ccgtaagatg cttttctgtg  13500
actggtgagt actcaaccaa gtcattctga gaatagtgta tgcggcgacc gagttgctct  13560
tgcccggcgt caatacggga taataccgcg ccacatagca gaactttaaa agtgctcatc  13620
attggaaaac gttcttcggg gcgaaaactc tcaaggatct taccgctgtt gagatccagt  13680
tcgatgtaac ccactcgtgc acccaactga tcttcagcat cttttacttt caccagcgtt  13740
tctgggtgag caaaaacagg aaggcaaaat gccgcaaaaa agggaataag ggcgacacgg  13800
aaatgttgaa tactcatact cttccttttt caatattatt gaagcattta tcagggttat  13860
tgtctcatga gcggatacat atttgaatgt atttagaaaa ataaacaaat aggggttccg  13920
cgcacatttc cccgaaaagt gccacctgac gtctaagaaa ccattattat catgacatta  13980
acctataaaa ataggcgtat cacgag                                      14006
```

```
SEQ ID NO: 9            moltype = DNA  length = 21335
FEATURE                 Location/Qualifiers
misc_feature            1..21335
                        note = plasmid with Cas9; LIP8 targeting guide RNAs
source                  1..21335
                        mol_type = other DNA
                        organism = synthetic construct
SEQUENCE: 9
ggttccgctt cctcgctcac tgactcgctg cgctcggtcg ttcggctgcg gcgagcggta  60
tcagctcact caaaggcggt aatacggtta tccacagaat caggggataa cgcaggaaag  120
aacatgtgag caaaaggcca gcaaaaggcc aggaaccgta aaaaggccgc gttgctggcg  180
tttttccata ggctccgccc ccctgacgag catcacaaaa atcgacgctc aagtcagagg  240
tggcgaaacc cgacaggact ataaagatac caggcgtttc cccctggaag ctccctcgtg  300
cgctctcctg ttccgaccct gccgcttacc ggatacctgt ccgcctttct cccttcggga  360
agcgtggcgc tttctcatag ctcacgctgt aggtatctca gttcggtgta ggtcgttcgc  420
tccaagctgg gctgtgtgca cgaacccccc gttcagcccg accgctgcgc cttatccggt  480
aactatcgtc ttgagtccaa cccggtaaga cacgacttat cgccactggc agcagccact  540
ggtaacagga ttagcagagc gaggtatgta ggcggtgcta cagagttctt gaagtggtgg  600
cctaactacg gctacactag aaggacagta tttggtatct gcgctctgct gaagccagtt  660
accttcggaa aaagagttgg tagctcttga tccggcaaac aaaccaccgc tggtagcggt  720
ggtttttttg tttgcaagca gcagattacg cgcagaaaaa aaggatctca agaagatcct  780
ttgatctttt ctacggggtc tgacgctcag tggaacgaaa actcacgtta agggattttg  840
gtcatgagat tatcaaaaag gatcttcacc tagatccttt taaattaaaa atgaagtttt  900
aaatcaatct aaagtatata tgagtaaact tggtctgaca gttaccaatg cttaatcagt  960
gaggcaccta tctcagcgat ctgtctattt cgttcatcca tagttgcctg actccccgtc  1020
gtgtagataa ctacgatacg ggagggctta ccatctggcc ccagtgctgc aatgataccg  1080
cgagacccac gctcaccggc tccagattta tcagcaataa accagccagc cggaagggcc  1140
gagcgcagaa gtggtcctgc aactttatcc gcctccatcc agtctattaa ttgttgccgg  1200
gaagctagag taagtagttc gccagttaat agtttgcgca acgttgttgc cattgctgca  1260
ggcatcgtgg tgtcacgctc gtcgtttggt atggcttcat tcagctccgg ttcccaacga  1320
tcaaggcgag ttacatgatc ccccatgttg tgcaaaaaag cggttagctc cttcggtcct  1380
ccgatcgttg tcagaagtaa gttggccgca gtgttatcac tcatggttat ggcagcactg  1440
cataattctc ttactgtcat gccatccgta agatgctttt ctgtgactgg tgagtactca  1500
accaagtcat tctgagaata gtgtatgcgg cgaccgagtt gctcttgccc ggcgtcaaca  1560
cgggataata ccgcgccaca tagcagaact ttaaaagtgc tcatcattgg aaaacgttct  1620
tcggggcgaa aactctcaag gatcttaccg ctgttgagat ccagttcgat gtaacccact  1680
cgtgcaccca actgatcttc agcatctttt actttcacca gcgtttctgg gtgagcaaaa  1740
acaggaaggc aaaatgccgc aaaaaaggga ataagggcga cacggaaatg ttgaatactc  1800
atactcttcc tttttcaata ttattgaagc atttatcagg gttattgtct catgagcgga  1860
tacatatttg aatgtattta gaaaaataaa caaatagggg ttccgcgcac atttccccga  1920
aaagtgccac ctgacgtcta agaaaccatt attatcatga cattaaccta taaaaatagg  1980
cgtatcacga ggccctttcg tctggcctag gaagcgactt ccaatcgctt tgcatatcca  2040
gtaccacacc cacaggcgtt tgtgctactc tactgatagc aatagatgcg tcataattgg  2100
ttggcccgct gagcctccac aggatactat tgcacatacc ctggtcatgt gcagatcagc  2160
tcatttgtgg agactctgga gtaacttaga cgacgcctgg ttcaattgcc gcaatgtgcg  2220
cccacgcaga taatgtattg aggggtggag cgcctcttgg ggacttgctg tacttgtacg  2280
ggatattaaa cgcactcagc aagaccatga cgtaaaacac acctactgta cgatacgtac  2340
tgtaggtatt gtactcgtac ccggtactac aaatagtacg atactatacg gagtgtattt  2400
gtaccttgat atacgactgg cggagtgaag agaaggagtt gaacaagacc agatggggat  2460
atcagcccca gtgctttgta ttacaagtac gagtacttaa tagatactgt aaggctattg  2520
atacggatgg cagtaagtca ttgagtaagc aattgtggcc cagcatctcc cctacgtact  2580
tgtaccatac cccatggaga caccaatggt ctttcacgca cactgtcgtg tgctgtatcg  2640
cagaatcggg tgtccaacca aatgccgtta cccccacgtc acagccgata gacagataca  2700
ccatcaatac cagcaggttg tatcatgcgg ttggctgaag gtaagctgat tggtctaaaa  2760
actgtagctg tcctaattca acgagcgcta tttggggcca accacctcgg ccaagcggcc  2820
tttaatctgc gtgccccaga ggcgtctaat gaggctctgg ccgccactgt aggagtgttt  2880
ctctgtgcgc acacgcagtt ttgagtttgg gcgactttcc ctttttccca attgcgtaca  2940
cacacagctc cgagctaagc gctgtccttg aaccttctcc ctcttttccc tctttttctc  3000
ttccccttcc cctcctccac attaaggcca aatcctgaat tgcaccaact agtacaacga  3060
caacaatgga caagaagtac tccatcggtt tggacattgg tactaactct gtcggctggg  3120
```

-continued

```
ccgtcatcac cgacgagtac aaggttccct ccaagaagtt caaggtcctt ggcaacaccg  3180
accgacactc tatcaagaag aacctgatcg gtgctctgct gttcgactct ggcgagactg  3240
ccgaggccac ccgactgaag cgaaccgctc gacgccgata cacccgacga aagaaccgaa  3300
tctgttacct ccaggagatc ttcagcaacg agatggctaa ggtcgacgac tccttcttcc  3360
accgactcga ggagtctttc ctggtcgaag aggataagaa gcacgagcga caccccatct  3420
tcggcaacat tgttgatgag gttgcctacc atgagaagta ccccaccatc taccacctcc  3480
gaaagaagct cgtcgactcc actgacaagg ctgacctccg actcatctac cttgctctcg  3540
cccacatgat caagttccga ggtcacttcc tcattgaggg tgatctcaac cccgacaact  3600
ccgacgttga caagctgttc atccagctcg tccagaccta caaccagctc tttgaggaga  3660
accctatcaa cgcttctggt gttgacgcca aggccattct ctccgcccga ctctctaagt  3720
cccgacgact cgagaacctc attgcccagc tgcccggcga gaagaagaac ggcctcttcg  3780
gtaacctgat tgctctctct cttggtctga cccccaactt caagtccaac tttgacctcg  3840
ccgaggacgc caagctccag ctgtccaagg acacctacga tgacgatctg gacaacctcc  3900
tggcccagat cggtgaccag tacgccgatc tcttccttgc cgccaagaac ctctccgacg  3960
ccatcctgct ctccgacatc ctccgagtca acaccgagat taccaaggct cctctgtctg  4020
cctctatgat caagcgatac gacgagcacc accaggatct cactcttctc aaggctctcg  4080
tccgacagca gctccccgag aagtacaagg agattttctt tgaccagtcc aagaacggtt  4140
acgctggcta cattgacggt ggtgcttccc aggaagagtt ttacaagttc atcaagccta  4200
ttctggagaa gatggacggt accgaggagc tgctcgtcaa gctcaaccga gaggacctcc  4260
ttcgaaagca gcgaaccttc gataacggct ccatccccca ccagatccac ctgggtgagc  4320
tccacgccat tctccgaaga caagaggact tctacccctt cctaaaggat aaccgagaga  4380
agatcgagaa gattctcacc ttccgaatcc cctactacgt cggtcccctc gctcgaggta  4440
actcccgatt tgcttggatg acccgaaagt ccgaggagac tatcaccccc tggaactttg  4500
aagaggtagt cgacaagggt gcctccgccc agtctttcat tgagcggatg accaacttcg  4560
ataagaacct ccccaacgag aaggtccttc ccaagcactc tctcctctac gagtacttca  4620
ccgtctacaa cgagctgacc aaggtcaagt acgttaccga gggcatgcga aagcccgctt  4680
tcctctctgg tgagcagaag aaggccattg tcgacctcct gttcaagact aaccgaaaag  4740
tcaccgtcaa gcagctcaag gaagactact tcaagaagat tgagtgcttc gactccgtcg  4800
agatttccgg tgtcgaggac cgattcaacg cctccctcgg cacctaccac gatcttctga  4860
agatcatcaa ggacaaggac tttcttgata acgaggagaa cgaggacatt ctcgaggaca  4920
tcgtcctcac cctcaccctt ttcgaggatc gagagatgat cgaggagcga ctcaagacct  4980
acgcccatct cttcgacgac aaggtcatga agcaactcaa gcgacgacga tacactggct  5040
ggggccgact ttcccgaaag ctcatcaacg gcatccgaga caagcagtct ggcaagacca  5100
tcctggactt cctgaagtcc gacggtttcg ccaaccgaaa cttcatgcag ctcatccacg  5160
acgactctct taccttcaaa gaggatatcc agaaggccca ggtttctggc cagggcgact  5220
ccctccacga gcacattgcc aacctcgccg gatcccccgc catcaaaaag ggtatcctcc  5280
agaccgtcaa ggttgtcgac gaactcgtga aggtcatggg ccgacacaag cccgagaaca  5340
tcgttatcga gatggcccga gagaaccaga ccacccagaa gggtcagaag aactcccgag  5400
agcgaatgaa gcgaatcgaa gagggtatca aggagctcgg ttcccagatt ctcaaggagc  5460
accccgtcga gaacacccag ctccagaacg agaaactcta cctgtactac ctccagaatg  5520
gccgagacat gtacgttgac caggagctcg acatcaaccg actctccgac tacgacgtcg  5580
accacattgt tcctcagtcc ttcctcaagg acgactccat cgacaacaag gttctgaccc  5640
gatctgacaa gaaccgaggt aagtccgaca acgttccctc cgaagaggtc gttaagaaga  5700
tgaagaacta ctggcgacag cttctcaacg ccaaactgat cacccagcga aagtttgaca  5760
acctcaccaa ggccgagcga ggtggtctgt ccgagctgga caaggccggc ttcattaagc  5820
gacagctggt cgagactcga cagatcacca agcacgtcgc ccagatcctc gactcccgaa  5880
tgaacaccaa gtacgacgag aacgacaagc tcatccggga ggtcaaggtc atcaccctga  5940
agtctaagct tgtctccgac ttccgaaagg acttccagtt ctacaaggtc cgagagatca  6000
acaactacca ccacgcccac gacgcctacc tcaacgccgt tgttggtacc gccctcatca  6060
agaagtatcc caagctcgag tccgagttcg tttacggcga ctacaaggtt tacgatgtcc  6120
gaaagatgat tgccaagtcc gagcaggaga tcggtaaggc caccgccaag tacttttcct  6180
actccaacat catgaatttc ttcaagaccg agatcactct cgccaacggt gagattcgaa  6240
agcgacccct gattgagact aatggtgaga ctggtgagat cgtctgggat aagggccgag  6300
acttcgccac cgtccgaaag gtcctgtcca tgccccaggt caacattgtc aagaagaccg  6360
aggtccagac cggtggcttc tccaaggagt ccattctccc caagcgaaac tccgacaaac  6420
tcatcgcccg taagaaggac tgggatccga agaagtacgg tggtttcgat tctcccaccg  6480
ttgcctactc cgtcctcgtt gttgctaaag tcgagaaggg taagtctaag aaactcaagt  6540
ccgtgaagga gctactcggt atcaccatca tggagcgatc ttcttttgag aagaacccca  6600
ttgacttcct cgaggccaag ggttacaaag aggtcaagaa ggacctgatt atcaagctgc  6660
ccaagtactc cctctttgag ctcgagaacg gccgaaagcg aatgctggct tccgctggtg  6720
agctgcagaa gggcaacgag ctcgctctgc cctccaagta cgtcaacttc ctctacctgg  6780
cctcccacta cgagaagctc aagggctccc ccgaggacaa cgagcagaag cagctgttcg  6840
ttgagcagca caagcactac ctcgacgaga tcatcgagca gatctccgag ttctccaagc  6900
gagtcatcct cgctgacgcc aaccttgata aggttctctc tgcttacaac aagcaccggg  6960
acaagcccat ccgagagcag gccgagaata tcatccacct cttcactctc accaacctcg  7020
gcgctcctgc tgccttcaag tacttcgaca ccaccattga ccgaaagagg tacacctcca  7080
ccaaggaagt cctcgacgcc accctgatcc accagtccat caccggcctc tacgaaaccc  7140
gaatcgacct ctcccagctc ggcggtgact ctcgagccga ccccaagaag aagcgaaaag  7200
tctaaatatc cgaagatcaa gagcgaagca agttgtaagt ccaggacatg tttcccgccc  7260
acgcgagtga tttataacac ctctcttttt tgacacccgc tcgccttgaa attcatgtca  7320
cataaattat agtcaacgac gtttgaataa cttgtcttgt agttcgatga tgatcatatg  7380
attacattaa tagtaattac tgtatttgat atatatacta attacaatag tacatattag  7440
aacatacaat agttagtgcc gtgaagtggc ttaaaatacc gcgagtcgat tacgtaatat  7500
tattacctct tgcccatcga acgtacaagt actcctctgt tctctccttc ctttgctttg  7560
tgcacgaaga actgcggtca ggtgacacaa ctttttccat ctcagggtgt gtcgcgtgtg  7620
cttcatccaa actttagttg gggttcgggt tcgcgcgaga tgatcacgtg ccctgatttg  7680
gtgtcgtccc ccgtcgcgct gcgcacgtga tttatttatt tccggtggct gctgtctacg  7740
cggggccttc tctgcccttc tgtttcaacc ttcgggcggt tctcgtaacc agcagtagca  7800
atccatttcg aaactcaaag agctaaaaac gttaaacctc agcagtcgct cgacgaatgg  7860
```

```
gctgcggttg ggaagcccac gaggcctata gccagagcct cgagttgaca ggagcccaga  7920
cgccttttcc aacggcaact tttatataaa atggcaatgt attcatgcaa ttgcggccgt  7980
gtcaggttgg agacactgga ccacactctc cattgcttcc tgaggagatg gatcattgct  8040
agtgcatcta cgcgcagcaa tcccgcaagc tcgacaaccg tagatgggct ttggtgggcc  8100
aatcaattac gcaacccgca cgttaaattg tatgaggaag gaaggccacg gtacaaagtg  8160
ggtggtcttc acccagtggt tgttggtggc gtcatgcaga ccatgcattg ggatagcac   8220
agggttgggg tgtcttgtgg actcaatggg tgaaaggaga tggaaaaggg cggtgaaaag  8280
tggtagaatc gaaatccctg acgtcaattt ataaagtaaa atgcgtttct gccattttgc  8340
tcccctcctt ctttcgcaat cgcctcccca aaagttgtcg tggcagtaca catgcttgca  8400
tacaatgaag ctaatccggc ttgctcagta gttgctatat ccaggcatgg tgtgaaaccc  8460
ctcaaagtat atataggagc ggtgagcccc agtctggggt cttttctctc catctcaaaa  8520
ctactttctc acaatgacga gactgatgag tccgtgagga cgaaacgagt aagctcgtcg  8580
agggctgcaa aattcacgag ttttagagct agaaatagca agttaaaata aggctagtcc  8640
gttatcaact tgaaaaagtg gcaccgagtc ggtgcttttg gccggcatgg tcccagcctc  8700
ctcgctggcg ccggctgggc aacatgcttc ggcatggcga atgggactaa acttcgagct  8760
aatccagtag cttacgttac ccaggggcag gtcaactggc tagccacgag tctgtcccag  8820
gtcgcaattt agtgtaataa acaatatata tattgagtct aaagggaatt gtagctattg  8880
tgattgtgtg attttcgtct tgctggttct tattgtgtcc cattcgtttc atcctgatga  8940
ggacccctgg aaccggtgtt ttcttagtct ctgcaatcgc tagtcttgtt gctatgacag  9000
ttgcgtcgac actattcagg tcatctatcg gttattctga tattataata cctccggatc  9060
gatgtacctg atttatactt gcagcaatgt ttacttctta tcgttggacc ccgtcttcaa  9120
ttacacttcc caactgggaa cacccctctt tatcgaccca ttttaggtaa tttaccctag  9180
cccattgtct ccataaggaa tattacccta acccacagtc cagggtgccc aggtccttct  9240
ttggccaaat tttaacttcg gtcctatggc acagcggtag cgcgtgagat tgcaaatctt  9300
aaggtcccga gttcgaatct cggtgggacc tagttgaaaa atacctctaa tgcgccgatg  9360
gtttagtggt aaaatccatc gttgccatcg atgggccccc ggttcgattc cgggtcggcg  9420
caggttgacg tacagcaggc tgaacgagga tgttttagag ctagaaatag caagttaaaa  9480
taaggctagt ccgttatcaa cttgaaaaag tggcaccgag tcggtgcttt ttttttcgc   9540
gatacacgaa tgtgatacgg atcaaagtaa gcaggactac gataagataa cgaatgcggt  9600
gcagtccatg tcgattaggt atagatacat ttattttgtg ttatgttaca ttttgggggg  9660
atactgtcct acttgtagta cctacttgta gtggcgcgtc tattcctttg ccctcggacg  9720
agtgctgggg cgtcggtttc cactatcggc gagtacttct acacagccat cggtccagac  9780
ggccgcgctt ctgcgggcga tttgtgtacg cccgacagtc ccggctccgg atcggacgat  9840
tgcgtcgcat cgaccctgcg cccaagctgc atcatcgaaa ttgccgtcaa ccaagctctg  9900
atagagttgg tcaagaccaa tgcggagcat atacgcccgg agccgcggcg atcctgcaag  9960
ctccggatgc ctccgctcga agtagcgcgt ctgctgctcc atacaagcca accacggcct  10020
ccagaagaag atgttggcga cctcgtattg ggaatccccg aacatcgcct cgctccagtc  10080
aatgaccgct gttatgcggc cattgtccgt caggacattg ttggagccga aatccgcgtg  10140
cacgaggtgc cggacttcgg ggcagtcctc ggcccaaagc atcagctcat cgagagcctg  10200
cgcgacggac gcactgacgg tgtcgtccat cacagtttgc cagtgataca catggggatc  10260
agcaatcgcg catatgaaat cacgccatgt agtgtattga ccgattcctt gcggtccgaa  10320
tgggccgaac ccgctcgtct ggctaagatc ggccgcagcg atcgcatcca tggcctccgc  10380
gaccggctgc agaacagcgg gcagttcggt ttcaggcagg tcttgcaacg tgacaccctg  10440
tgcacggcgg gagatgcaat aggtcaggct ctcgctgaat tccccaatgt caagcacttc  10500
cggaatcggg agcgcggccg atgcaaagtg ccgataaaca taacgatctt tgtagaaacc  10560
atcggcgcag ctatttaccc gcaggacata tccacgccct cctacatcga agctgaaagc  10620
acgagattct tcgccctccg agagctgcat caggtcggag acgctgtcga acttttcgat  10680
cagaaacttc tcgacagacg tcgcggtgag ttcaggcttt ttcatatggg tacctgagaa  10740
catttttgtg tctaggtgtt tgtgtttgga ctgcgatcag tgaagaaaag aagaggaaaa  10800
attgtgcaag aaattttgct ttcaagactt ggctgatgca gcagggtaac tctgggacac  10860
agacctatgt ttgtggttaa actcaatgca cgtggtacgt gcgtggagcg cttacccatc  10920
caagggtgtg gacatggaac cgacggtccg tggagttgtg taatgtcatt ttggcgactc  10980
ttgaagcaag gctataaaaa aattgtgtgg cttgagtctt atcgagctcg gtcactacaa  11040
gagttaatct tcctgtctca ggcagacagg tcaggcaggg ttacttttgg gtgtgctgta  11100
actcactgta tggccgttag tgcgcataga cgttgtacat actggaccga attgtagcgt  11160
gctcaatagg gccaataaag ctattgtagg gatccgaatt ttcagaacct aatttatctg  11220
ttacccggcc tgtggctcgc acagcttaaa aatggtcaaa ctttcccctt cttgtctttt  11280
tttcctcaca ttcatcaggt tcttgtcttg atctttcaag tgagtattaa ttaccgacct  11340
tggttcttca ttgggagagc attggaagcc gtggtgcagc aaccacaaaa cggttcttcc  11400
ccttcgatac cttcttgcct gcctttcaat acaagtcggc tcgattagcg gtggtcgccc  11460
ccgccagcgg agaacatgga actaacccag aatgagagct aagtggagaa agaagagagt  11520
cagacgactc aagcgaaagc gccgcaaggt ccgagctcga tccaaataag cggtttttaa  11580
cggagattta acactaaatc gaagaacttt tcccgtttca tttgcgaatg agctcgttaa  11640
caaaatcccc cagttttttt atccagctgt aaggattgac attagtaatg aattattgtt  11700
tggtatattt aaatctgtag ttcctttctg tccgtgtcgg caactgtcgt actcgtgatt  11760
tacttgtatt gacgaatact tactgtagcg cactctgctg ctactggtcg taaggatgtg  11820
ctatttcggt gtatggtggg tttttggggg gtcggaaccg aagactgtta cacgggcacg  11880
gctcgttgtg tacacgcaca gagctcttgc gagtcatgtt gtagctagct cgtcgtgttc  11940
aggaactgtt cgatggttcg gagagagtcg ccgcccagaa catacgcgca ccgatgtcag  12000
cagacagcct tattacaagt atattcaagc aagtatatcc gtagggtgcg ggtgatttgg  12060
atctaaggtt cgtactcaac actcacgagc agcttgccta tgttacatcc ttttatcaga  12120
cataacataa ttggagttta cttacacacg gggtgtacct gtatgagcac cacctacaat  12180
tgtagcactg gtacttgtac aaagaattta ttcgtacgaa tcacagggac ggccgccctc  12240
accgaaccag cgaatacctc agcggtcccc tgcagtgact caacaaagcg atatgaacat  12300
cttgcgatgg tatcctgctg atagttttta ctgtacaaac acctgtgtag ctccttctag  12360
catttttaag ttattcacac ctcaagggga gggataaatt aaataaattc caaaagcgaa  12420
gatcgagaaa ctaaattaaa attccaaaaa cgaagttgga acacaacccc ccgaaaaaaa  12480
acaacaaaca aaaaacccaa caaaataaac aaaaacaaaa taaatatata actaccagta  12540
tctgactaaa agttcaaata ctcgtactta caacaaatag aaatgagccg gccaaaattc  12600
```

```
tgcagaaaaa aatttcaaac aagtactggt ataattaaat taaaaaacac atcaaagtat  12660
cataacgtta gttattttat tttatttaat aaaagaaaac aacaagatgg gctcaaaact  12720
ttcaacttat acgatacata ccaaataaca atttagtatt tatctaagtg cttttcgtag  12780
ataatggaat acaaatggat atccagagta tacacatgga tagtatacac tgacacgaca  12840
attctgtatc tctttatgtt aactactgtg aggcattaaa tagagcttga tatataaaat  12900
gttacatttc acagtctgaa cttttgcaga ttacctaatt tggtaagata ttaattatga  12960
actgaaagtt gatggcatcc ctaaatttga tgaaagatga aattgtaaat gaggtggtaa  13020
aagagctaca gtcgttttgt tttgagatac catcatctct aacgaaatat ctattaaaaa  13080
tctcagtgtg atcatgagtc attgccatcc tggaaaatgt catcatggct gatatttcta  13140
actgtttact tgagataaat atatatttac aagaacttcc cttgaaatta atttagatat  13200
aaaatgtttg cgggcaagtt actacgagga ataaattata tctagaaagc ggaagagcgc  13260
ccaatacgca aaccgcctct ccccgcgcgt tggccgattc attaatgcag ctggcacgac  13320
aggtttcccg actggaaagc gggcagtgag cgcaacgcaa ttaatgtgag ttagctcact  13380
cattaggcac cccaggcttt acactttatg cttccggctc gtatgttgtg tggaattgtg  13440
agcggataac aatttcacac aggaaacagc tatgaccatg attacgccaa gcttggtacc  13500
agagacgggt tggcggcgta tttgtgtccc aaaaaacagc cccaattgcc ccaattgacc  13560
ccaaattgac ccagtagcgg gcccaacccc ggcgagagcc cccttcaccc cacatatcaa  13620
acctcccccg gttcccacac ttgccgttaa gggcgtaggg tactgcagtc tggaatctac  13680
gcttgttcag actttgtact agtttctttg tctggccatc cgggtaaccc atgccggacg  13740
caaaatagac tactgaaaat ttttttgctt tgtggttggg actttagcca agggtataaa  13800
agaccaccgt ccccgaatta cctttcctct tcttttctct ctctccttgt caactcacac  13860
ccgaaatcgt taagcatttc cttctgagta taagaatcat tcgctagcca caaaaatgat  13920
ggctccctcc attcgaaagt tctttgctgg tggtgtgtgt cgaactaacg ttcagcttcc  13980
cggtaaggtg gttgtcatca ctggtgccaa caccggcatt ggcaaggaga ctgcccgaga  14040
gctcgcttcc cgaggagccc gagtttacat tgcttgccga gatgttctga agggcgagtc  14100
tgctgcctct gagattcgag ttgacactaa gaactcccag gtgctcgtgc gaaagctcga  14160
cctttccgac actaagtcta tccgagcctt tgctgagggc tttctcgctg aggagaagca  14220
gcttcacatt ctgattaaca acgctggagt tatgatgtgt ccttactcta agactgctga  14280
tggtttcgag actcacctcg gagtcaacca cctgggccac ttcctcctca cctacctgct  14340
cctggagcga ctcaaggtgt ctgcccctgc ccgagtggtt aacgtttcct ccgtggctca  14400
ccacattggc aagattccct tccacgacct ccagtccgag aagcgatact cccgaggttt  14460
tgcttactgc cactccaagc tggccaacgt tctctttacc cgagagctgg ccaagcgact  14520
ccagggaacc ggcgtcacca cctacgccgt tcaccccggt gtcgtccgat ccgagctggt  14580
ccgacactcc tccctgctct gcctgctctg gcgactcttc tccccccttcg ttaagaccgc  14640
ccgagagggt gcccagacct ccctgcactg cgccctggct gagggcctgg agcccctgtc  14700
tggcaagtac ttctctgact gcaagcgaac ctgggtgtct ccccgagctc gaaacaacaa  14760
gactgccgag cgactctgga acgtttcctg tgagcttctc ggtattcgat gggagtagac  14820
gcgtgcaatt aacagatagt ttgccggtga taattctctt aacctcccac actcctttga  14880
cataacgatt tatgtaacga aactgaaatt tgaccagata ttgttgtaaa tagaaaatct  14940
ggcttgtagg tggcaaacta gtggtgtgtt ctgtggagca ttctcacttt tggtaaacga  15000
cattgcttca agtgcagcgg aatcaaaaag tataaagtgg gcagcgagta tacctgtaca  15060
gactgtaggc gataactcaa tccaattacc ccccacaaca tgactggcca aactgatctc  15120
aagactttat tgaaatcagc aacaccgatt ctcaatgaag gcacatactt cttctgcaac  15180
attcacttga cgcctaaagt tggtgagaaa tggaccgaca agacatattc tgctatccac  15240
ggactgttgc ctgtgtcggt ggctacaata cgtgagtcag aagggctgac ggtggtggtt  15300
cccaaggaaa aggtcgacga gtatctgtct gactcgtcat tgccgccttt ggagtacgac  15360
tccaactatg agtgtgcttg gatcactttg acgatacatt cttcgttgga ggctgtgggt  15420
ctgacagctg cgttttcggc gcggttggcc gacaacaata tcagctgcaa cgtcattgct  15480
ggctttcatc atgatcacat ttttgtcggc aaaggcgacg cccagagagc cattgacgtt  15540
ctttctaatt tggaccgata gccgtatagt ccagtctatc tataagttca actaactcgt  15600
aactattacc ataacatata cttcactgcc ccagataagg ttccgataaa aagttctgca  15660
gactaaattt atttcagtct cctcttcacc accaaaatgc cctcctacga agctcgagct  15720
aacgtccaca agtccgcctt tgccgctcga gtgctcaagc tcgtggcagc caagaaaacc  15780
aacctgtgtg cttctctgga tgttaccacc accaaggagc tcattgagct tgccgataag  15840
gtcggacctt atgtgtgcat gatcaagacc catatcgaca tcattgacga cttcacctac  15900
gccggcactg tgctcccccct caaggaactt gctcttaagc acggtttctt cctgttcgag  15960
gacagaaagt tcgcagatat tggcaacact gtcaagcacc agtacaagaa cggtgtctac  16020
cgaatcgccg agtggtccga tatcaccaac gcccacggtg tacccggaac cggaatcatt  16080
gctggcctgc gagctggtgc cgaggaaact gtctctgaac agaagaagga ggacgtctct  16140
gactacgaga actcccagta caaggagttc ctggtcccct ctcccaacga gaagctggcc  16200
agaggtctgc tcatgctggc cgagctgtct tgcaagggct ctctggccac tggcgagtac  16260
tccaagcaga ccattgagct tgcccgatcc gaccccgagt ttgtggttgg cttcattgcc  16320
cagaaccgac ctaagggcga ctctgaggac tggcttattc tgacccccgg ggtgggtctt  16380
gacgacaagg gagacgctct cggacagcag taccgaactg ttgaggatgt catgtctacc  16440
ggaacggata tcataattgt cggccgaggt ctgtacggcc agaaccgaga tcctattgag  16500
gaggccaagc gataccagaa ggctggctgg gaggcttacc agaagattaa ctgttagagg  16560
ttagactatg gatatgtaat ttaactgtgt atatagagag cgtgcaagta tggagcgctt  16620
gttcagcttg tatgatggtc agacgacctg tctgatcgag tatgtatgat actgcacaac  16680
ctgtgtatcc gcatgatctg tccaatgggg catgttgttg tgtttctcga tacggagatg  16740
ctgggtacaa gtagctaata cgattgaact acttatactt atatgaggct tgaagaaagc  16800
tgacttgtgt atgacttatt ctcaactaca tccccagtca caataccacc actgcactac  16860
cactacacct cgagcatgca tctagtggtg tgttctgtgg agcattctca cttttggtaa  16920
acgacattgc ttcaagtgca gcggaatcaa aaagtataaa gtgggcagcg agtatacctg  16980
tacagactgt aggcgataac tcaatccaat taccccccac aacatgactg gccaaactga  17040
tctcaagact ttattgaaat cagcaacacc gattctcaat gaaggcacat acttcttctg  17100
caacattcac ttgacgccta aagttggtga gaaatggacc gacaagacat attctgctat  17160
ccacggactg ttgcctgtgt cggtggctac aatacgtgag tcagaagggc tgacggtggt  17220
ggttcccaag gaaaaggtcg acgagtatct gtctgactcg tcattgccgc ctttggagta  17280
cgactccaac tatgagtgtg cttggatcac tttgacgata cattcttcgt tggaggctgt  17340
```

```
gggtctgaca gctgcgtttt cggcgcggtt ggccgacaac aatatcagct gcaacgtcat  17400
tgctggcttt catcatgatc acatttttgt cggcaaaggc gacgcccaga gagccattga  17460
cgttctttct aatttggacc gatagccgta tagtccagtc tatctataag ttcaactaac  17520
tcgtaactat taccataaca tatacttcac tgccccagat aaggttccga taaaaagttc  17580
tgcagactaa atttatttca gtctcctctt caccaccaaa atgccctcct acgaagctcg  17640
agctaacgtc cacaagtccg cctttgccgc tcgagtgctc aagctcgtgg cagccaagaa  17700
aaccaacctg tgtgcttctc tggatgttac caccaccaag ggccgctcg agcatgcatc  17760
tagagggccc aattcgccct atagtgagtc gtattacaat tcactggccg tcgttttaca  17820
acgtcgtgac tgggaaaacc ctggcgttac ccaacttaat cgccttgcag cacatccccc  17880
tttcgccagc tggcgtaata gcgaagaggc ccgcaccgat cgcccttccc aacagttgcg  17940
cagcctgaat ggcgaatgga cgcgccctgt agcggcgcat taagcgcggc gggtgtggtg  18000
gttacgcgca gcgtgaccgc tacacttgcc agcgccctag cgcccgctcc tttcgctttc  18060
ttcccttcct ttctcgccac gttcgccggc tttccccgtc aagctctaaa tcgggggctc  18120
cctttagggt tccgatttag tgctttacgg cacctcgacc ccaaaaaact tgattagggt  18180
gatggttcac gtagtgggcc atcgccctga tagacggttt ttcgcccttt gacgttggag  18240
tccacgttct ttaatagtgg actcttgttc caaactggaa caacactcaa ccctatctcg  18300
gtctattctt ttgatttata agggattttg ccgatttcgg cctattggtt aaaaaatgag  18360
ctgatttaac aaaaatttaa cgcgaatttt aacaaaattc agggcgcaag ggctgctaaa  18420
ggaagcggaa cacgtagaaa gccagtccgc agaaacggtg ctgaccccgg atgaatgtca  18480
gctactgggc tatctggaca agggaaaacg caagcgcaaa gagaaagcag gtagcttgca  18540
gtgggcttac atggcgatag ctagactggg cggttttatg gacagcaagc gaaccggaat  18600
tgccagctgg ggcgccctct ggtaaggttg ggaagccctg caaagtaaac tggatggctt  18660
tcttgccgcc aaggatctga tggcgcaggg gatcaagatc tgatcaagag acaggatgag  18720
gatcgtttcg catgattgaa caagatggat tgcacgcagg ttctccggcc gcttgggtgg  18780
agaggctatt cggctatgac tgggcacaac agacaatcgg ctgctctgat gccgccgtgt  18840
tccggctgtc agcgcagggg cgcccggttc tttttgtcaa gaccgacctg tccggtgccc  18900
tgaatgaact gcaggacgag gcagcgcggc tatcgtggct ggccacgacg ggcgttcctt  18960
gcgcagctgt gctcgacgtt gtcactgaag cgggaaggga ctggctgcta ttgggcgaag  19020
tgccggggca ggatctcctg tcatcccacc ttgctcctgc cgagaaagta tccatcatgg  19080
ctgatgcaat gcggcggctg catacgcttg atccggctac ctgcccattc gaccaccaag  19140
cgaaacatcg catcgagcga gcacgtactc ggatggaagc cggtcttgtc gatcaggatg  19200
atctggacga agagcatcag gggctcgcgc cagccgaact gttcgccagg ctcaaggcgc  19260
gcatgcccga cggcgaggat ctcgtcgtga cccatggcga tgcctgcttg ccgaatatca  19320
tggtggaaaa tggccgcttt tctggattca tcgactgtgg ccggctgggt gtggcggacc  19380
gctatcagga catagcgttg gctacccgtg atattgctga agagcttggc ggcgaatggg  19440
ctgaccgctt cctcgtgctt tacggtatcg ccgctcccga ttcgcagcgc atcgccttct  19500
atcgccttct tgacgagttc ttctgaattg aaaaaggaag agtatgagta ttcaacattt  19560
ccgtgtcgcc cttattccct tttttgcggc attttgcctt cctgtttttg ctcacccaga  19620
aacgctggtg aaagtaaaag atgctgaaga tcagttgggt gcacgagtgg gttacatcga  19680
actggatctc aacagcggta agatccttga gagttttcgc cccgaagaac gttttccaat  19740
gatgagcact tttaaagttc tgctatgtgg cgcggtatta tcccgtattg acgccgggca  19800
agagcaactc ggtcgccgca tacactattc tcagaatgac ttggttgagt actcaccagt  19860
cacagaaaag catcttacgg atggcatgac agtaagagaa ttatgcagtg ctgccataac  19920
catgagtgat aacactgcgg ccaacttact tctgacaacg atcggaggac cgaaggagct  19980
aaccgctttt ttgcacaaca tgggggatca tgtaactcgc cttgatcgtt gggaaccgga  20040
gctgaatgaa gccataccaa acgacgagcg tgacaccacg atgcctgtag caatggcaac  20100
aacgttgcgc aaactattaa ctggcgaact acttactcta gcttcccggc aacaattaat  20160
agactggatg gaggcggata aagttgcagg accacttctg cgctcggccc ttccggctgg  20220
ctggtttatt gctgataaat ctggagccgg tgagcgtggg tctcgcggta tcattgcagc  20280
actggggcca gatggtaagc cctcccgtat cgtagttatc tacacgacgg ggagtcaggc  20340
aactatggat gaacgaaata gacagatcgc tgagataggt gcctcactga ttaagcattg  20400
gtaactgtca gaccaagttt actcatatat actttagatt gatttaaaac ttcattttta  20460
atttaaaagg atctaggtga agatcctttt tgataatctc atgaccaaaa tcccttaacg  20520
tgagttttcg ttccactgag cgtcagaccc cgtagaaaag atcaaaggat cttcttgaga  20580
tcctttttt ctgcgcgtaa tctgctgctt gcaaacaaaa aaaccaccgc taccagcggt  20640
ggtttgtttg ccggatcaag agctaccaac tctttttccg aaggtaactg gcttcagcag  20700
agcgcagata ccaaatactg ttcttctagt gtagccgtag ttaggccacc acttcaagaa  20760
ctctgtagca ccgcctacat acctcgctct gctaatcctg ttaccagtgg ctgctgccag  20820
tggcgataag tcgtgtctta ccgggttgga ctcaagacga tagttaccgg ataaggcgca  20880
gcggtcgggc tgaacggggg gttcgtgcac acagcccagc ttggagcgaa cgacctacac  20940
cgaactgaga tacctacagc gtgagctatg agaaagcgcc acgcttcccg aagggagaaa  21000
ggcggacagg tatccggtaa gcggcagggt cggaacagga gagcgcacga gggagcttcc  21060
agggggaaac gcctggtatc tttatagtcc tgtcgggttt cgccacctct gacttgagcg  21120
tcgatttttg tgatgctcgt caggggggcg gagcctatgg aaaaacgcca gcaacgcggc  21180
ctttttacgg ttcctggcct tttgctggcc ttttgctcac atgttctttc ctgcgttatc  21240
ccctgattct gtggataacc gtattaccgc ctttgagtga gctgataccg ctcgccgcag  21300
ccgaacgacc gagcgcagcg agtcagtgag cgagg                            21335

SEQ ID NO: 10          moltype = DNA  length = 8089
FEATURE                Location/Qualifiers
misc_feature           1..8089
                       note = expression plasmid
source                 1..8089
                       mol_type = other DNA
                       organism = synthetic construct
SEQUENCE: 10
aagcggaaga gcgcccaata cgcaaaccgc ctctccccgc gcgttggccg attcattaat  60
gcagctggca cgacaggttt cccgactgga aagcgggcag tgagcgcaac gcaattaatg  120
tgagttagct cactcattag gcaccccagg ctttacactt tatgcttccg gctcgtatgt  180
```

```
tgtgtggaat tgtgagcgga taacaatttc acacaggaaa cagctatgac catgattacg  240
ccaagcttgg taccagagac gggttggcgg cgtatttgtg tcccaaaaaa cagccccaat  300
tgccccaatt gaccccaaat tgacccagta gcgggcccaa ccccggcgag agcccccttc  360
accccacata tcaaacctcc cccggttccc acacttgccg ttaagggcgt agggtactgc  420
agtctggaat ctacgcttgt tcagactttg tactagtttc tttgtctggc catccgggta  480
acccatgccg gacgcaaaat agactactga aaattttttt gctttgtggt tgggacttta  540
gccaagggta taaaagacca ccgtccccga attacctttc ctcttctttt ctctctctcc  600
ttgtcaactc acacccgaaa tcgttaagca tttccttctg agtataagaa tcattcgcta  660
gccacaaaaa tgatggctcc ctccattcga aagttctttg ctggtggtgt gtgtcgaact  720
aacgttcagc ttcccggtaa ggtggttgtc atcactggtg ccaacaccgg cattggcaag  780
gagactgccc gagagctcgc ttcccgagga gcccgagttt acattgcttg ccgagatgtt  840
ctgaagggcg agtctgctgc ctctgagatt cgagttgaca ctaagaactc ccaggtgctc  900
gtgcgaaagc tcgacctttc cgacactaag tctatccgag cctttgctga gggctttctc  960
gctgaggaga agcagcttca cattctgatt aacaacgctg gagttatgat gtgtccttac  1020
tctaagactg ctgatggttt cgagactcac ctcggagtca accacctggg ccacttcctc  1080
ctcacctacc tgctcctgga gcgactcaag gtgtctgccc ctgcccgagt ggttaacgtt  1140
tcctccgtgg ctcaccacat tggcaagatt cccttccacg acctccagtc cgagaagcga  1200
tactcccgag gttttgctta ctgccactcc aagctggcca acgttctctt tacccgagag  1260
ctggccaagc gactccaggg aaccggcgtc accacctacg ccgttcaccc cggtgtcgtc  1320
cgatccgagc tggtccgaca ctcctccctg ctctgcctgc tctggcgact cttctccccc  1380
ttcgttaaga ccgcccgaga gggtgcccag acctccctgc actgcgccct ggctgagggc  1440
ctggagcccc tgtctggcaa gtacttctct gactgcaagc gaacctgggt gtctccccga  1500
gctcgaaaca acaagactgc cgagcgactc tggaacgttt cctgtgagct tctcggtatt  1560
cgatgggagt agacgcgtgc aattaacaga tagtttgccg gtgataattc tcttaacctc  1620
ccacactcct ttgacataac gatttatgta acgaaactga aatttgacca gatattgttg  1680
taaatagaaa atctggcttg taggtggcaa actagtggtg tgttctgtgg agcattctca  1740
cttttggtaa acgacattgc ttcaagtgca gcggaatcaa aaagtataaa gtgggcagcg  1800
agtatacctg tacagactgt aggcgataac tcaatccaat tacccccccac aacatgactg  1860
gccaaactga tctcaagact ttattgaaat cagcaacacc gattctcaat gaaggcacat  1920
acttcttctg caacattcac ttgacgccta aagttggtga gaaatggacc gacaagacat  1980
attctgctat ccacggactg ttgcctgtgt cggtggctac aatacgtgag tcagaagggc  2040
tgacggtggt ggttcccaag gaaaaggtcg acgagtatct gtctgactcg tcattgccgc  2100
ctttggagta cgactccaac tatgagtgtg cttggatcac tttgacgata cattcttcgt  2160
tggaggctgt gggtctgaca gctgcgtttt cggcgcggtt ggccgacaac aatatcagct  2220
gcaacgtcat tgctggcttt catcatgatc acatttttgt cggcaaaggc gacgcccaga  2280
gagccattga cgttctttct aatttggacc gatagccgta tagtccagtc tatctataag  2340
ttcaactaac tcgtaactat taccataaca tatacttcac tgccccagat aaggttccga  2400
taaaaagttc tgcagactaa atttatttca gtctcctctt caccaccaaa atgccctcct  2460
acgaagctcg agctaacgtc cacaagtccg cctttgccgc tcgagtgctc aagctcgtgg  2520
cagccaagaa aaccaacctg tgtgcttctc tggatgttac caccaccaag gagctcattg  2580
agcttgccga taaggtcgga ccttatgtgt gcatgatcaa gacccatatc gacatcattg  2640
acgacttcac ctacgccggc actgtgctcc ccctcaagga acttgctctt aagcacggtt  2700
tcttcctgtt cgaggacaga aagttcgcag atattggcaa cactgtcaag caccagtaca  2760
agaacggtgt ctaccgaatc gccgagtggt ccgatatcac caacgcccac ggtgtacccg  2820
gaaccggaat cattgctggc ctgcgagctg gtgccgagga aactgtctct gaacagaaga  2880
aggaggacgt ctctgactac gagaactccc agtacaagga gttcctggtc ccctctccca  2940
acgagaagct ggccagaggt ctgctcatgc tggccgagct gtcttgcaag ggctctctgg  3000
ccactggcga gtactccaag cagaccattg agcttgcccg atccgacccc gagtttgtgg  3060
ttggcttcat tgcccagaac cgacctaagg gcgactctga ggactggctt attctgaccc  3120
ccggggtggg tcttgacgac aagggagacg ctctcggaca gcagtaccga actgttgagg  3180
atgtcatgtc taccggaacg gatatcataa ttgtcggccg aggtctgtac ggccagaacc  3240
gagatcctat tgaggaggcc aagcgatacc agaaggctgg ctgggaggct taccagaaga  3300
ttaactgtta gaggttagac tatggatatg taatttaact gtgtatatag agagcgtgca  3360
agtatggagc gcttgttcag cttgtatgat ggtcagacga cctgtctgat cgagtatgta  3420
tgatactgca caacctgtgt atccgcatga tctgtccaat ggggcatgtt gttgtgtttc  3480
tcgatacgga gatgctgggt acaagtagct aatacgattg aactacttat acttatatga  3540
ggcttgaaga aagctgactt gtgtatgact tattctcaac tacatcccca gtcacaatac  3600
caccactgca ctaccactac acctcgagca tgcatctagt ggtgtgttct gtggagcatt  3660
ctcacttttg gtaaacgaca ttgcttcaag tgcagcggaa tcaaaaagta taaagtgggc  3720
agcgagtata cctgtacaga ctgtaggcga taactcaatc caattacccc ccacaacatg  3780
actggccaaa ctgatctcaa gactttattg aaatcagcaa caccgattct caatgaaggc  3840
acatacttct tctgcaacat tcacttgacg cctaaagttg gtgagaaatg gaccgacaag  3900
acatattctg ctatccacgg actgttgcct gtgtcggtgg ctacaatacg tgagtcagaa  3960
gggctgacgg tggtggttcc caaggaaaag gtcgacgagt atctgtctga ctcgtcattg  4020
ccgcctttgg agtacgactc caactatgag tgtgcttgga tcactttgac gatacattct  4080
tcgttggagg ctgtgggtct gacagctgcg ttttcggcgc ggttggccga caacaatatc  4140
agctgcaacg tcattgctgg ctttcatcat gatcacattt ttgtcggcaa aggcgacgcc  4200
cagagagcca ttgacgttct ttctaatttg gaccgatagc cgtatagtcc agtctatcta  4260
taagttcaac taactcgtaa ctattaccat aacatatact tcactgcccc agataaggtt  4320
ccgataaaaa gttctgcaga ctaaatttat ttcagtctcc tcttcaccac caaaatgccc  4380
tcctacgaag ctcgagctaa cgtccacaag tccgcctttg ccgctcgagt gctcaagctc  4440
gtggcagcca agaaaaccaa cctgtgtgct tctctggatg ttaccaccac caaggggccg  4500
ctcgagcatg catctagagg gcccaattcg ccctatagtg agtcgtatta caattcactg  4560
gccgtcgttt tacaacgtcg tgactgggaa aaccctggcg ttacccaact taatcgcctt  4620
gcagcacatc ccccttttcgc cagctggcgt aatagcgaag aggcccgcac cgatcgccct  4680
tcccaacagt tgcgcagcct gaatggcgaa tggacgcgcc ctgtagcggc gcattaagcg  4740
cggcgggtgt ggtggttacg cgcagcgtga ccgctacact tgccagcgcc ctagcgcccg  4800
ctcctttcgc tttcttccct tcctttctcg ccacgttcgc cggctttccc cgtcaagctc  4860
taaatcgggg gctcccttta gggttccgat ttagtgcttt acggcacctc gaccccaaaa  4920
```

```
aacttgatta gggtgatggt tcacgtagtg ggccatcgcc ctgatagacg gtttttcgcc  4980
ctttgacgtt ggagtccacg ttctttaata gtggactctt gttccaaact ggaacaacac  5040
tcaaccctat ctcggtctat tcttttgatt tataagggat tttgccgatt tcggcctatt  5100
ggttaaaaaa tgagctgatt taacaaaaat ttaacgcgaa ttttaacaaa attcagggcg  5160
caagggctgc taaaggaagc ggaacacgta gaaagccagt ccgcagaaac ggtgctgacc  5220
ccggatgaat gtcagctact gggctatctg gacaagggaa aacgcaagcg caaagagaaa  5280
gcaggtagct tgcagtgggc ttacatggcg atagctagac tgggcggttt tatggacagc  5340
aagcgaaccg gaattgccag ctggggcgcc ctctggtaag gttgggaagc cctgcaaagt  5400
aaactggatg gctttcttgc cgccaaggat ctgatggcgc aggggatcaa gatctgatca  5460
agagacagga tgaggatcgt ttcgcatgat tgaacaagat ggattgcacg caggttctcc  5520
ggccgcttgg gtggagaggc tattcggcta tgactgggca caacagacaa tcggctgctc  5580
tgatgccgcc gtgttccggc tgtcagcgca ggggcgcccg gttctttttg tcaagaccga  5640
cctgtccggt gccctgaatg aactgcagga cgaggcagcg cggctatcgt ggctggccac  5700
gacgggcgtt ccttgcgcag ctgtgctcga cgttgtcact gaagcgggaa gggactggct  5760
gctattgggc gaagtgccgg ggcaggatct cctgtcatcc caccttgctc ctgccgagaa  5820
agtatccatc atggctgatg caatgcggcg gctgcatacg cttgatccgg ctacctgccc  5880
attcgaccac caagcgaaac atcgcatcga gcgagcacgt actcggatgg aagccggtct  5940
tgtcgatcag gatgatctgg acgaagagca tcaggggctc gcgccagccg aactgttcgc  6000
caggctcaag gcgcgcatgc ccgacggcga ggatctcgtc gtgacccatg gcgatgcctg  6060
cttgccgaat atcatggtgg aaaatggccg cttttctgga ttcatcgact gtggccggct  6120
gggtgtggcg gaccgctatc aggacatagc gttggctacc cgtgatattg ctgaagagct  6180
tggcggcgaa tgggctgacc gcttcctcgt gctttacggt atcgccgctc ccgattcgca  6240
gcgcatcgcc ttctatcgcc ttcttgacga gttcttctga attgaaaaag gaagagtatg  6300
agtattcaac atttccgtgt cgcccttatt cccttttttg cggcattttg ccttcctgtt  6360
tttgctcacc cagaaacgct ggtgaaagta aaagatgctg aagatcagtt gggtgcacga  6420
gtgggttaca tcgaactgga tctcaacagc ggtaagatcc ttgagagttt tcgccccgaa  6480
gaacgttttc caatgatgag cacttttaaa gttctgctat gtggcgcggt attatcccgt  6540
attgacgccg ggcaagagca actcggtcgc cgcatacact attctcagaa tgacttggtt  6600
gagtactcac cagtcacaga aaagcatctt acggatggca tgacagtaag agaattatgc  6660
agtgctgcca taaccatgag tgataacact gcggccaact tacttctgac aacgatcgga  6720
ggaccgaagg agctaaccgc ttttttgcac aacatggggg atcatgtaac tcgccttgat  6780
cgttgggaac cggagctgaa tgaagccata ccaaacgacg agcgtgacac cacgatgcct  6840
gtagcaatgg caacaacgtt gcgcaaacta ttaactggcg aactacttac tctagcttcc  6900
cggcaacaat taatagactg gatggaggcg gataaagttg caggaccact tctgcgctcg  6960
gcccttccgg ctggctggtt tattgctgat aaatctggag ccggtgagcg tgggtctcgc  7020
ggtatcattg cagcactggg gccagatggt aagccctccc gtatcgtagt tatctacacg  7080
acggggagtc aggcaactat ggatgaacga aatagacaga tcgctgagat aggtgcctca  7140
ctgattaagc attggtaact gtcagaccaa gtttactcat atatacttta gattgattta  7200
aaacttcatt tttaatttaa aaggatctag gtgaagatcc tttttgataa tctcatgacc  7260
aaaatccctt aacgtgagtt ttcgttccac tgagcgtcag accccgtaga aaagatcaaa  7320
ggatcttctt gagatccttt ttttctgcgc gtaatctgct gcttgcaaac aaaaaaacca  7380
ccgctaccag cggtggtttg tttgccggat caagagctac caactctttt tccgaaggta  7440
actggcttca gcagagcgca gataccaaat actgttcttc tagtgtagcc gtagttaggc  7500
caccacttca agaactctgt agcaccgcct acatacctcg ctctgctaat cctgttacca  7560
gtggctgctg ccagtggcga taagtcgtgt cttaccgggt tggactcaag acgatagtta  7620
ccggataagg cgcagcggtc gggctgaacg gggggttcgt gcacacagcc cagcttggag  7680
cgaacgacct acaccgaact gagataccta cagcgtgagc tatgagaaag cgccacgctt  7740
cccgaaggga gaaaggcgga caggtatccg gtaagcggca gggtcggaac aggagagcgc  7800
acgagggagc ttccaggggg aaacgcctgg tatctttata gtcctgtcgg gtttcgccac  7860
ctctgacttg agcgtcgatt tttgtgatgc tcgtcagggg ggcggagcct atggaaaaac  7920
gccagcaacg cggccttttt acggttcctg gccttttgct ggccttttgc tcacatgttc  7980
tttcctgcgt tatcccctga ttctgtggat aaccgtatta ccgcctttga gtgagctgat  8040
accgctcgcc gcagccgaac gaccgagcgc agcgagtcag tgagcgagg              8089

SEQ ID NO: 11          moltype = DNA  length = 8159
FEATURE                Location/Qualifiers
misc_feature           1..8159
                       note = expression plasmid
source                 1..8159
                       mol_type = other DNA
                       organism = synthetic construct
SEQUENCE: 11
aagcggaaga gcgcccaata cgcaaaccgc ctctccccgc gcgttggccg attcattaat  60
gcagctggca cgacaggttt cccgactgga aagcgggcag tgagcgcaac gcaattaatg  120
tgagttagct cactcattag gcaccccagg ctttacactt tatgcttccg gctcgtatgt  180
tgtgtggaat tgtgagcgga taacaatttc acacaggaaa cagctatgac catgattacg  240
ccaagcttgg taccagagac gggttggcgg cgtatttgtg tcccaaaaaa cagccccaat  300
tgccccaatt gaccccaaat tgacccagta gcgggcccaa ccccggcgag agccccctc  360
accccacata tcaaacctcc cccggttccc acacttgccg ttaagggcgt agggtactgc  420
agtctggaat ctacgcttgt tcagactttg tactagtttc tttgtctggc catccgggta  480
acccatgccg gacgcaaaat agactactga aaattttttt gctttgtggt tgggacttta  540
gccaagggta taaaagacca ccgtccccga attacctttc ctcttctttt ctctctctcc  600
ttgtcaactc acacccgaaa tcgttaagca tttccttctg agtataagaa tcattcgcta  660
gcccacaaaa atgacccgat ccaagttcac cgagtacaag caggttctcc gaaactcttg  720
tgttggcaag ccccagtaca ctgagaagga ttaccccgat ctcgacggaa agaactttct  780
cgtcactggt gctactggtg gagttggtct ggaggccact aagctgctcc ttgagaagaa  840
gtctcacgtt attatggttg gccgatctaa gactaagtct cagtctaccc ttgacgagct  900
tcagaagact tactctcacg gtactttcga tttcgttgag gctgatctct ctgaccttac  960
cactgttgag cgagccggag agtacattcg atctaagtac actacccttg acggtgccat  1020
```

-continued

```
tcttaacgct ggagtcatgg ctccccccta ctctctcact ccccagggtc acgagtctca  1080
gtggggtatt aacgttgttg ctcactttct cctgtctaag tacatctctc ctgctctgat  1140
ttctgctgct cagactgccc ccaaggacac cgttcgactt gtttgggtgt cttcttctgt  1200
cgttgccatg tctccttacg agggaggtat taagtttgac gatattaacc actctaaggt  1260
caagaaccct tctccttgga ccctttactc tcagtctaag attggtgatg cttacctggc  1320
ttacctttgg tctaagcacc accccgattc tggagtcctt tctgtctctc tggaccccgg  1380
taacctggct tctgatctct ctcgacacac ttcttggctt tcttctatta agaactacgt  1440
tctttaccct cccaagtacg gtgcctacac tgagctgtct gctcttctca acccttccgt  1500
taagaacaac gagcacctta ttccctgggg tattgaggga caccttcgac aggatgtcga  1560
cgatggtcga cgaggaaagg acggagagga gctctggcag ggtcttaaca aggatgtcga  1620
gggtttcttt aaggaggagt aaacgcgtgc aattaacaga tagtttgccg gtgataattc  1680
tcttaacctc ccacactcct ttgacataac gatttatgta acgaaactga aatttgacca  1740
gatattgttg taaatagaaa atctggcttg taggtggcaa actagtggtg tgttctgtgg  1800
agcattctca cttttggtaa acgacattgc ttcaagtgca gcggaatcaa aaagtataaa  1860
gtgggcagcg agtatacctg tacagactgt aggcgataac tcaatccaat taccccccac  1920
aacatgactg gccaaactga tctcaagact ttattgaaat cagcaacacc gattctcaat  1980
gaaggcacat acttcttctg caacattcac ttgacgccta aagttggtga gaaatggacc  2040
gacaagacat attctgctat ccacggactg ttgcctgtgt cggtggctac aatacgtgag  2100
tcagaagggc tgacggtggt ggttcccaag gaaaaggtcg acgagtatct gtctgactcg  2160
tcattgccgc ctttggagta cgactccaac tatgagtgtg cttggatcac tttgacgata  2220
cattcttcgt tggaggctgt gggtctgaca gctgcgtttt cggcgcggtt ggccgacaac  2280
aatatcagct gcaacgtcat tgctggcttt catcatgatc acatttttgt cggcaaaggc  2340
gacgcccaga gagccattga cgttctttct aatttggacc gatagccgta tagtccagtc  2400
tatctataag ttcaactaac tcgtaactat taccataaca tatacttcac tgccccagat  2460
aaggttccga taaaaagttc tgcagactaa atttatttca gtctcctctt caccaccaaa  2520
atgccctcct acgaagctcg agctaacgtc cacaagtccg cctttgccgc tcgagtgctc  2580
aagctcgtgg cagccaagaa aaccaacctg tgtgcttctc tggatgttac caccaccaag  2640
gagctcattg agcttgccga taaggtcgga ccttatgtgt gcatgatcaa gacccatatc  2700
gacatcattg acgacttcac ctacgccggc actgtgctcc ccctcaagga acttgctctt  2760
aagcacggtt tcttcctgtt cgaggacaga aagttcgcag atattggcaa cactgtcaag  2820
caccagtaca agaacggtgt ctaccgaatc gccgagtggt ccgatatcac caacgcccac  2880
ggtgtacccg gaaccggaat cattgctggc ctgcgagctg gtgccgagga aactgtctct  2940
gaacagaaga aggaggacgt ctctgactac gagaactccc agtacaagga gttcctggtc  3000
ccctctccca acgagaagct ggccagaggt ctgctcatgc tggccgagct gtcttgcaag  3060
ggctctctgg ccactggcga gtactccaag cagaccattg agcttgcccg atccgacccc  3120
gagtttgtgg ttggcttcat tgcccagaac cgacctaagg gcgactctga ggactggctt  3180
attctgaccc ccggggtggg tcttgacgac aagggagacg ctctcggaca gcagtaccga  3240
actgttgagg atgtcatgtc taccggaacg gatatcataa ttgtcggccg aggtctgtac  3300
ggccagaacc gagatcctat tgaggaggcc aagcgatacc agaaggctgg ctgggaggct  3360
taccagaaga ttaactgtta gaggttagac tatggatatg taatttaact gtgtatatag  3420
agagcgtgca agtatggagc gcttgttcag cttgtatgat ggtcagacga cctgtctgat  3480
cgagtatgta tgatactgca caacctgtgt atccgcatga tctgtccaat ggggcatgtt  3540
gttgtgtttc tcgatacgga gatgctgggt acaagtagct aatacgattg aactacttat  3600
acttatatga ggcttgaaga aagctgactt gtgtatgact tattctcaac tacatcccca  3660
gtcacaatac caccactgca ctaccactac acctcgagca tgcatctagt ggtgtgttct  3720
gtggagcatt ctcacttttg gtaaacgaca ttgcttcaag tgcagcggaa tcaaaaagta  3780
taaagtgggc agcgagtata cctgtacaga ctgtaggcga taactcaatc caattacccc  3840
ccacaacatg actggccaaa ctgatctcaa gactttattg aaatcagcaa caccgattct  3900
caatgaaggc acatacttct tctgcaacat tcacttgacg cctaaagttg gtgagaaatg  3960
gaccgacaag acatattctg ctatccacgg actgttgcct gtgtcggtgg ctacaatacg  4020
tgagtcagaa gggctgacgg tggtggttcc caaggaaaag gtcgacgagt atctgtctga  4080
ctcgtcattg ccgcctttgg agtacgactc caactatgag tgtgcttgga tcactttgac  4140
gatacattct tcgttggagg ctgtgggtct gacagctgcg ttttcggcgc ggttggccga  4200
caacaatatc agctgcaacg tcattgctgg ctttcatcat gatcacattt ttgtcggcaa  4260
aggcgacgcc cagagagcca ttgacgttct ttctaatttg gaccgatagc cgtatagtcc  4320
agtctatcta taagttcaac taactcgtaa ctattaccat aacatatact tcactgcccc  4380
agataaggtt ccgataaaaa gttctgcaga ctaaatttat ttcagtctcc tcttcaccac  4440
caaaatgccc tcctacgaag ctcgagctaa cgtccacaag tccgcctttg ccgctcgagt  4500
gctcaagctc gtggcagcca agaaaaccaa cctgtgtgct tctctggatg ttaccaccac  4560
caaggggccg ctcgagcatg catctagagg gcccaattcg ccctatagtg agtcgtatta  4620
caattcactg gccgtcgttt tacaacgtcg tgactgggaa aaccctggcg ttacccaact  4680
taatcgcctt gcagcacatc ccccttcgc cagctggcgt aatagcgaag aggcccgcac  4740
cgatcgccct tcccaacagt tgcgcagcct gaatggcgaa tggacgcgcc ctgtagcggc  4800
gcattaagcg cggcgggtgt ggtggttacg cgcagcgtga ccgctacact tgccagcgcc  4860
ctagcgcccg ctcctttcgc tttcttccct tcctttctcg ccacgttcgc cggctttccc  4920
cgtcaagctc taaatcgggg gctcccttta gggttccgat ttagtgcttt acggcacctc  4980
gaccccaaaa aacttgatta gggtgatggt tcacgtagtg ggccatcgcc ctgatagacg  5040
gtttttcgcc ctttgacgtt ggagtccacg ttctttaata gtggactctt gttccaaact  5100
ggaacaacac tcaaccctat ctcggtctat tcttttgatt tataagggat tttgccgatt  5160
tcggcctatt ggttaaaaaa tgagctgatt taacaaaaat ttaacgcgaa ttttaacaaa  5220
attcagggcg caagggctgc taaaggaagc ggaacacgta gaaagccagt ccgcagaaac  5280
ggtgctgacc ccggatgaat gtcagctact gggctatctg gacaagggaa aacgcaagcg  5340
caaagagaaa gcaggtagct tgcagtgggc ttacatggcg atagctagac tgggcggttt  5400
tatggacagc aagcgaaccg gaattgccag ctggggcgcc ctctggtaag gttgggaagc  5460
cctgcaaagt aaactggatg gctttcttgc cgccaaggat ctgatggcgc aggggatcaa  5520
gatctgatca agagacagga tgaggatcgt ttcgcatgat tgaacaagat ggattgcacg  5580
caggttctcc ggccgcttgg gtggagaggc tattcggcta tgactgggca caacagacaa  5640
tcggctgctc tgatgccgcc gtgttccggc tgtcagcgca ggggcgcccg gttctttttg  5700
tcaagaccga cctgtccggt gccctgaatg aactgcagga cgaggcagcg cggctatcgt  5760
```

```
ggctggccac gacgggcgtt ccttgcgcag ctgtgctcga cgttgtcact gaagcgggaa  5820
gggactggct gctattgggc gaagtgccgg ggcaggatct cctgtcatcc caccttgctc  5880
ctgccgagaa agtatccatc atggctgatg caatgcggcg gctgcatacg cttgatccgg  5940
ctacctgccc attcgaccac caagcgaaac atcgcatcga gcgagcacgt actcggatgg  6000
aagccggtct tgtcgatcag gatgatctgg acgaagagca tcaggggctc gcgccagccg  6060
aactgttcgc caggctcaag gcgcgcatgc ccgacggcga ggatctcgtc gtgacccatg  6120
gcgatgcctg cttgccgaat atcatggtgg aaaatggccg cttttctgga ttcatcgact  6180
gtggccggct gggtgtggcg gaccgctatc aggacatagc gttggctacc cgtgatattg  6240
ctgaagagct tggcggcgaa tgggctgacc gcttcctcgt gctttacggt atcgccgctc  6300
ccgattcgca gcgcatcgcc ttctatcgcc ttcttgacga gttcttctga attgaaaaag  6360
gaagagtatg agtattcaac atttccgtgt cgcccttatt cccttttttg cggcattttg  6420
ccttcctgtt tttgctcacc cagaaacgct ggtgaaagta aaagatgctg aagatcagtt  6480
gggtgcacga gtgggttaca tcgaactgga tctcaacagc ggtaagatcc ttgagagttt  6540
tcgccccgaa gaacgttttc caatgatgag cacttttaaa gttctgctat gtggcgcggt  6600
attatcccgt attgacgccg ggcaagagca actcggtcgc cgcatacact attctcagaa  6660
tgacttggtt gagtactcac cagtcacaga aaagcatctt acggatggca tgacagtaag  6720
agaattatgc agtgctgcca taaccatgag tgataacact gcggccaact tacttctgac  6780
aacgatcgga ggaccgaagg agctaaccgc ttttttgcac aacatggggg atcatgtaac  6840
tcgccttgat cgttgggaac cggagctgaa tgaagccata ccaaacgacg agcgtgacac  6900
cacgatgcct gtagcaatgg caacaacgtt gcgcaaacta ttaactggcg aactacttac  6960
tctagcttcc cggcaacaat taatagactg gatggaggcg gataaagttg caggaccact  7020
tctgcgctcg gcccttccgg ctggctggtt tattgctgat aaatctggag ccggtgagcg  7080
tgggtctcgc ggtatcattg cagcactggg gccagatggt aagccctccc gtatcgtagt  7140
tatctacacg acggggagtc aggcaactat ggatgaacga aatagacaga tcgctgagat  7200
aggtgcctca ctgattaagc attggtaact gtcagaccaa gtttactcat atatacttta  7260
gattgattta aaacttcatt tttaatttaa aaggatctag gtgaagatcc tttttgataa  7320
tctcatgacc aaaatccctt aacgtgagtt ttcgttccac tgagcgtcag accccgtaga  7380
aaagatcaaa ggatcttctt gagatccttt ttttctgcgc gtaatctgct gcttgcaaac  7440
aaaaaaacca ccgctaccag cggtggtttg tttgccggat caagagctac caactctttt  7500
tccgaaggta actggcttca gcagagcgca gataccaaat actgttcttc tagtgtagcc  7560
gtagttaggc caccacttca agaactctgt agcaccgcct acatacctcg ctctgctaat  7620
cctgttacca gtggctgctg ccagtggcga taagtcgtgt cttaccgggt tggactcaag  7680
acgatagtta ccggataagg cgcagcggtc gggctgaacg gggggttcgt gcacacagcc  7740
cagcttggag cgaacgacct acaccgaact gagataccta cagcgtgagc tatgagaaag  7800
cgccacgctt cccgaaggga gaaaggcgga caggtatccg gtaagcggca gggtcggaac  7860
aggagagcgc acgagggagc ttccaggggg aaacgcctgg tatctttata gtcctgtcgg  7920
gtttcgccac ctctgacttg agcgtcgatt tttgtgatgc tcgtcagggg ggcggagcct  7980
atggaaaaac gccagcaacg cggccttttt acggttcctg gccttttgct ggccttttgc  8040
tcacatgttc tttcctgcgt tatcccctga ttctgtggat aaccgtatta ccgcctttga  8100
gtgagctgat accgctcgcc gcagccgaac gaccgagcgc agcgagtcag tgagcgagg   8159

SEQ ID NO: 12           moltype = DNA  length = 8147
FEATURE                 Location/Qualifiers
misc_feature            1..8147
                        note = expression plasmid
source                  1..8147
                        mol_type = other DNA
                        organism = synthetic construct
SEQUENCE: 12
aagcggaaga gcgcccaata cgcaaaccgc ctctccccgc gcgttggccg attcattaat  60
gcagctggca cgacaggttt cccgactgga aagcgggcag tgagcgcaac gcaattaatg  120
tgagttagct cactcattag gcaccccagg ctttacactt tatgcttccg gctcgtatgt  180
tgtgtggaat tgtgagcgga taacaatttc acacaggaaa cagctatgac catgattacg  240
ccaagcttgg taccagagac gggttggcgg cgtatttgtg tcccaaaaaa cagccccaat  300
tgccccaatt gaccccaaat tgacccagta gcgggcccaa ccccggcgag agccccccttc  360
accccacata tcaaacctcc cccggttccc acacttgccg ttaagggcgt agggtactgc  420
agtctggaat ctacgcttgt tcagactttg tactagtttc tttgtctggc catccgggta  480
acccatgccg gacgcaaaat agactactga aaattttttt gctttgtggt tgggacttta  540
gccaagggta taaaagacca ccgtccccga attacctttc ctcttctttt ctctctctcc  600
ttgtcaactc acacccgaaa tcgttaagca tttccttctg agtataagaa tcattcgcta  660
gcccacaaaa atggttaacg ttgcttacga gtggcttcga gactgctggc cccctaagcc  720
tgagttcctc cctaaggatt accctgacct caccggaaag accatcctta tcactggtgc  780
caacactggt attggttttg agtccgctaa ggctctcctc aagaagaacg ctaccgttgt  840
ttttgccaac cgatccgagg agaagactaa gatcgctatt gccaagattc aggctgagct  900
tggtggtgat tcttctcagc gatctatttt cgtcaagact gacctttccg atctctcttc  960
cattaagggc actgctgagg agcttaagtc taagggtatc actaagctcc actacaccat  1020
tcttaacgct ggtgttatgc agcctcccaa gggctccaag actaagcagg gttttgagct  1080
tcagattggt actaacgttc ttggccacca gctcctccag aagtttctca ctccccttgt  1140
tctcaacgct gtttcttctg atttcaccc tcgagttgtt tggctcgcct ctgctgctca  1200
cctttcttcc cctcccaacg gtggtattga ttgggattcc ttccgaaacg ctgattgggc  1260
tggtactgtc tctgcttacg gtcagtctaa gactggtaac atttaccagg cttacatcta  1320
cgctcagcag cacaaggatg tcatctctgt ctctgctcac cccggatacc ttgcttctga  1380
tctcactcga gcttacaagg gataccttca gtaccttatg aagctcctta tgtctcctcc  1440
cgtttacggt tcttacactg agcttttcgc tgctctttct cccaaggtta ctctcaagga  1500
gtctggtcga tacattggtc cttggggtca gttccgagag cttcgagatg acgttcagga  1560
gggccttacc gatggtactg ctcagaagct ctgggattgg gctgaggctg agattcgacc  1620
ttacacttaa acgcgtgcaa ttaacagata gtttgccggt gataattctc ttaacctccc  1680
acactccttt gacataacga tttatgtaac gaaactgaaa tttgaccaga tattgttgta  1740
aatagaaaat ctggcttgta ggtggcaaac tagtggtgtg ttctgtggag cattctcact  1800
```

-continued tttggtaaac gacattgctt caagtgcagc ggaatcaaaa agtataaagt gggcagcgag 1860
tatacctgta cagactgtag gcgataactc aatccaatta ccccccacaa catgactggc 1920
caaactgatc tcaagacttt attgaaatca gcaacaccga ttctcaatga aggcacatac 1980
ttcttctgca acattcactt gacgcctaaa gttggtgaga aatggaccga caagacatat 2040
tctgctatcc acggactgtt gcctgtgtcg gtggctacaa tacgtgagtc agaagggctg 2100
acggtggtgg ttcccaagga aaaggtcgac gagtatctgt ctgactcgtc attgccgcct 2160
ttggagtacg actccaacta tgagtgtgct tggatcactt tgacgataca ttcttcgttg 2220
gaggctgtgg gtctgacagc tgcgttttcg gcgcggttgg ccgacaacaa tatcagctgc 2280
aacgtcattg ctggctttca tcatgatcac atttttgtcg gcaaaggcga cgcccagaga 2340
gccattgacg ttctttctaa tttggaccga tagccgtata gtccagtcta tctataagtt 2400
caactaactc gtaactatta ccataacata tacttcactg ccccagataa ggttccgata 2460
aaaagttctg cagactaaat ttatttcagt ctcctcttca ccaccaaaat gccctcctac 2520
gaagctcgag ctaacgtcca caagtccgcc tttgccgctc gagtgctcaa gctcgtggca 2580
gccaagaaaa ccaacctgtg tgcttctctg gatgttacca ccaccaagga gctcattgag 2640
cttgccgata aggtcggacc ttatgtgtgc atgatcaaga cccatatcga catcattgac 2700
gacttcacct acgccggcac tgtgctcccc ctcaaggaac ttgctcttaa gcacggtttc 2760
ttcctgttcg aggacagaaa gttcgcagat attggcaaca ctgtcaagca ccagtacaag 2820
aacggtgtct accgaatcgc cgagtggtcc gatatcacca acgcccacgg tgtacccgga 2880
accggaatca ttgctggcct gcgagctggt gccgaggaaa ctgtctctga acagaagaag 2940
gaggacgtct ctgactacga gaactcccag tacaaggagt tcctggtccc ctctcccaac 3000
gagaagctgg ccagaggtct gctcatgctg gccgagctgt cttgcaaggg ctctctggcc 3060
actggcgagt actccaagca gaccattgag cttgcccgat ccgaccccga gtttgtggtt 3120
ggcttcattg cccagaaccg acctaagggc gactctgagg actggcttat tctgaccccc 3180
ggggtgggtc ttgacgacaa gggagacgct ctcggacagc agtaccgaac tgttgaggat 3240
gtcatgtcta ccggaacgga tatcataatt gtcggccgag gtctgtacgg ccagaaccga 3300
gatcctattg aggaggccaa gcgataccag aaggctggct gggaggctta ccagaagatt 3360
aactgttaga ggttagacta tggatatgta atttaactgt gtatatagag agcgtgcaag 3420
tatggagcgc ttgttcagct tgtatgatgg tcagacgacc tgtctgatcg agtatgtatg 3480
atactgcaca acctgtgtat ccgcatgatc tgtccaatgg ggcatgttgt tgtgtttctc 3540
gatacggaga tgctgggtac aagtagctaa tacgattgaa ctacttatac ttatatgagg 3600
cttgaagaaa gctgacttgt gtatgactta ttctcaacta catccccagt cacaatacca 3660
ccactgcact accactacac ctcgagcatg catctagtgg tgtgttctgt ggagcattct 3720
cacttttggt aaacgacatt gcttcaagtg cagcggaatc aaaaagtata aagtgggcag 3780
cgagtatacc tgtacagact gtaggcgata actcaatcca attacccccc acaacatgac 3840
tggccaaact gatctcaaga ctttattgaa atcagcaaca ccgattctca atgaaggcac 3900
atacttcttc tgcaacattc acttgacgcc taaagttggt gagaaatgga ccgacaagac 3960
atattctgct atccacggac tgttgcctgt gtcggtggct acaatacgtg agtcagaagg 4020
gctgacggtg gtggttccca aggaaaaggt cgacgagtat ctgtctgact cgtcattgcc 4080
gcctttggag tacgactcca actatgagtg tgcttggatc actttgacga tacattcttc 4140
gttggaggct gtgggtctga cagctgcgtt ttcggcgcgg ttggccgaca acaatatcag 4200
ctgcaacgtc attgctggct ttcatcatga tcacattttt gtcggcaaag gcgacgccca 4260
gagagccatt gacgttcttt ctaatttgga ccgatagccg tatagtccag tctatctata 4320
agttcaacta actcgtaact attaccataa catatacttc actgccccag ataaggttcc 4380
gataaaaagt tctgcagact aaatttattt cagtctcctc ttcaccacca aaatgccctc 4440
ctacgaagct cgagctaacg tccacaagtc cgcctttgcc gctcgagtgc tcaagctcgt 4500
ggcagccaag aaaaccaacc tgtgtgcttc tctggatgtt accaccacca aggggccgct 4560
cgagcatgca tctagagggc ccaattcgcc ctatagtgag tcgtattaca attcactggc 4620
cgtcgtttta caacgtcgtg actgggaaaa ccctggcgtt acccaactta atcgccttgc 4680
agcacatccc cctttcgcca gctggcgtaa tagcgaagag gcccgcaccg atcgcccttc 4740
ccaacagttg cgcagcctga atggcgaatg gacgcgccct gtagcggcgc attaagcgcg 4800
gcgggtgtgg tggttacgcg cagcgtgacc gctacacttg ccagcgccct agcgcccgct 4860
cctttcgctt tcttcccttc ctttctcgcc acgttcgccg gctttccccg tcaagctcta 4920
aatcgggggc tccctttagg gttccgattt agtgctttac ggcacctcga ccccaaaaaa 4980
cttgattagg gtgatggttc acgtagtggg ccatcgccct gatagacggt ttttcgccct 5040
ttgacgttgg agtccacgtt ctttaatagt ggactcttgt tccaaactgg aacaacactc 5100
aaccctatct cggtctattc ttttgattta taagggattt tgccgatttc ggcctattgg 5160
ttaaaaaatg agctgattta acaaaaattt aacgcgaatt ttaacaaaat tcagggcgca 5220
agggctgcta aaggaagcgg aacacgtaga aagccagtcc gcagaaacgg tgctgacccc 5280
ggatgaatgt cagctactgg gctatctgga caagggaaaa cgcaagcgca aagagaaagc 5340
aggtagcttg cagtgggctt acatggcgat agctagactg ggcggtttta tggacagcaa 5400
gcgaaccgga attgccagct ggggcgccct ctggtaaggt tgggaagccc tgcaaagtaa 5460
actggatggc tttcttgccg ccaaggatct gatggcgcag gggatcaaga tctgatcaag 5520
agacaggatg aggatcgttt cgcatgattg aacaagatgg attgcacgca ggttctccgg 5580
ccgcttgggt ggagaggcta ttcggctatg actgggcaca acagacaatc ggctgctctg 5640
atgccgccgt gttccggctg tcagcgcagg ggcgcccggt tctttttgtc aagaccgacc 5700
tgtccggtgc cctgaatgaa ctgcaggacg aggcagcgcg gctatcgtgg ctggccacga 5760
cgggcgttcc ttgcgcagct gtgctcgacg ttgtcactga agcgggaagg gactggctgc 5820
tattgggcga agtgccgggg caggatctcc tgtcatccca ccttgctcct gccgagaaag 5880
tatccatcat ggctgatgca atgcggcggc tgcatacgct tgatccggct acctgcccat 5940
tcgaccacca agcgaaacat cgcatcgagc gagcacgtac tcggatggaa gccggtcttg 6000
tcgatcagga tgatctggac gaagagcatc aggggctcgc gccagccgaa ctgttcgcca 6060
ggctcaaggc gcgcatgccc gacggcgagg atctcgtcgt gacccatggc gatgcctgct 6120
tgccgaatat catggtggaa aatggccgct tttctggatt catcgactgt ggccggctgg 6180
gtgtggcgga ccgctatcag gacatagcgt tggctacccg tgatattgct gaagagcttg 6240
gcggcgaatg ggctgaccgc ttcctcgtgc tttacggtat cgccgctccc gattcgcagc 6300
gcatcgcctt ctatcgcctt cttgacgagt tcttctgaat tgaaaaagga agagtatgag 6360
tattcaacat ttccgtgtcg cccttattcc cttttttgcg gcattttgcc ttcctgtttt 6420
tgctcaccca gaaacgctgg tgaaagtaaa agatgctgaa gatcagttgg gtgcacgagt 6480
gggttacatc gaactggatc tcaacagcgg taagatcctt gagagttttc gccccgaaga 6540

-continued

```
acgttttcca atgatgagca cttttaaagt tctgctatgt ggcgcggtat tatcccgtat  6600
tgacgccggg caagagcaac tcggtcgccg catacactat tctcagaatg acttggttga  6660
gtactcacca gtcacagaaa agcatcttac ggatggcatg acagtaagag aattatgcag  6720
tgctgccata accatgagtg ataacactgc ggccaactta cttctgacaa cgatcggagg  6780
accgaaggag ctaaccgctt ttttgcacaa catgggggat catgtaactc gccttgatcg  6840
ttgggaaccg gagctgaatg aagccatacc aaacgacgag cgtgacacca cgatgcctgt  6900
agcaatggca acaacgttgc gcaaactatt aactggcgaa ctacttactc tagcttcccg  6960
gcaacaatta atagactgga tggaggcgga taaagttgca ggaccacttc tgcgctcggc  7020
ccttccggct ggctggttta ttgctgataa atctggagcc ggtgagcgtg ggtctcgcgg  7080
tatcattgca gcactggggc cagatggtaa gccctcccgt atcgtagtta tctacacgac  7140
ggggagtcag gcaactatgg atgaacgaaa tagacagatc gctgagatag gtgcctcact  7200
gattaagcat tggtaactgt cagaccaagt ttactcatat atactttaga ttgatttaaa  7260
acttcatttt taatttaaaa ggatctaggt gaagatcctt tttgataatc tcatgaccaa  7320
aatcccttaa cgtgagtttt cgttccactg agcgtcagac cccgtagaaa agatcaaagg  7380
atcttcttga gatccttttt ttctgcgcgt aatctgctgc ttgcaaacaa aaaaaccacc  7440
gctaccagcg gtggtttgtt tgccggatca agagctacca actctttttc cgaaggtaac  7500
tggcttcagc agagcgcaga taccaaatac tgttcttcta gtgtagccgt agttaggcca  7560
ccacttcaag aactctgtag caccgcctac atacctcgct ctgctaatcc tgttaccagt  7620
ggctgctgcc agtggcgata agtcgtgtct taccgggttg gactcaagac gatagttacc  7680
ggataaggcg cagcggtcgg gctgaacggg gggttcgtgc acacagccca gcttggagcg  7740
aacgacctac accgaactga gatacctaca gcgtgagcta tgagaaagcg ccacgcttcc  7800
cgaagggaga aaggcggaca ggtatccggt aagcggcagg gtcggaacag gagagcgcac  7860
gagggagctt ccagggggaa acgcctggta tctttatagt cctgtcgggt ttcgccacct  7920
ctgacttgag cgtcgatttt tgtgatgctc gtcagggggg cggagcctat ggaaaaacgc  7980
cagcaacgcg gcctttttac ggttcctggc cttttgctgg ccttttgctc acatgttctt  8040
tcctgcgtta tcccctgatt ctgtggataa ccgtattacc gcctttgagt gagctgatac  8100
cgctcgccgc agccgaacga ccgagcgcag cgagtcagtg agcgagg                8147
```

RETINOID PRODUCTION

This application is the U.S. national phase of International Application No. PCT/EP2022/079143 filed Oct. 19, 2022, which designated the U.S. and claims priority to EP application Ser. No. 21/204,854.0 filed Oct. 26, 2021, and claims the benefit of U.S. Application No. 63/257,222 filed Oct. 19, 2021, the entire contents of each of which are hereby incorporated by reference.

The present invention is related to bio-production of retinoids with improved purity profile, particularly bio-retinoids with a high percentage of retinyl acetate, wherein the flux towards retinol is increased and wherein the percentage of unwanted by-products such as dihydroretinoids is minimized to a range of below 10%.

Retinol is an important intermediate/precursor in the process of retinoid production, particularly such as vitamin A production. Retinoids, including vitamin A, are one of very important and indispensable nutrient factors for human beings which have to be supplied via nutrition. Retinoids promote well-being of humans, inter alia in respect of vision, the immune system and growth.

Current chemical production methods for retinoids, including vitamin A and precursors thereof, have some undesirable characteristics such as e.g. high-energy consumption, complicated purification steps and/or undesirable by-products. Therefore, over the past decades, other approaches to manufacture retinoids, including vitamin A and precursors thereof, including microbial conversion steps, which would be more economical as well as ecological, have been investigated.

Unfortunately, the biological systems that produce retinoids are industrially intractable and/or produce the compounds at such low levels that commercial scale isolation is not practical. The most limiting factors include instability of intermediates including instability of retinol, inefficient enzymatic conversions and/or impurity due to accumulation of unwanted side-products.

Thus, it is an ongoing task to look for an improved process for fermentative production of retinoids, particularly with a high content of stable forms such as e.g. retinyl acetate, and at the same time to reduce the formation of unwanted by-products such as e.g. dihydroretinoids.

Surprisingly, we now identified a novel class of retinal reducing enzymes (RDHs) that are involved in formation of retinol, wherein the use of said enzymes in a fermentative production of retinoids leads to about 90% reduction of by-products such as dihydroretinoids and retinal that are generated during said fermentation process.

Thus, the present invention is related to a process for production of a retinoid-mix, such as a fermentation process using a suitable retinoid-producing host cell, said retinoid-mix comprising dihydroretinoids with a percentage of less than about 10% based on total retinoids within said mix.

As used herein, a "retinoid mix" is defined as all retinoids formed during a retinoid production process, such as e.g. fermentation process using a suitable host cell that is expressing suitable enzymes involved in formation of retinoids including but not limited to retinal, retinol, and retinyl acetate and optionally furthermore expressing enzymes involved in formation of beta-carotene. Said retinoid mix comprises retinal, retinol, retinyl acetate, and dihydroretinods.

Particularly, such retinoid-mix according to the present invention comprises dihydroretinoids, retinal, and retinyl acetate, wherein the percentage of dihydroretinoids is less than about 10% based on total retinoids, preferably wherein the percentage of retinal is less than about 8% based on total retinoids, further preferably wherein the percentage of retinyl acetate is at least about 80% based on total retinoids, even further preferably wherein the percentage of trans-isomers within said mix is at least about 80% based on the amount of all cis- and trans-retinoids.

In one embodiment, the percentage of dihydroretinoids based on total retinoids within said retinoid-mix is about less than 10, such as 9, 8, 7, 6, 5, 4, 3, 1% or less, preferably 2% or less, more preferably 1% or less, such as 0.9, 0.8, 0.7, 0.6, 0.5, 0.4, 0.3, 0.2, 0.1% or less, such as in the range of 1% to 0.1, 0.01, or 0.001%, as measurable at the end of the production or fermentation process.

In one embodiment, the percentage of retinal based on total retinoids within said retinoid-mix is about less than 8, such as 7, 6, 5, 4, 3, 1% or less, preferably 2% or less, more preferably 1% or less, such as 0.9, 0.8, 0.7, 0.6, 0.5, 0.4, 0.3, 0.2, 0.1% or less, such as in the range of 1% to 0.1, 0.01, or 0.001%, as measurable at the end of the production or fermentation process.

In a further embodiment, the percentage of retinyl acetate based on total retinoids within said retinoid-mix is at least about 80%, such as e.g. 85, 90, 92, 95, 98% or more retinyl acetate, as measurable at the end of the production or fermentation process using a suitable retinyl-acetate producing host cell.

In another embodiment, the percentage of trans-isoforms based on the total amount of cis and trans-isomers in said retinoid-mix is at least about 80, 85, 90, 92, 95, 98% or more, as measurable at the end of the production or fermentation process. Particularly, said mix comprises at least about 80% of trans-retinyl acetate, i.e. 80% of the retinyl acetate in the retinoid-mix is present in the trans-isomer.

The present invention is related to a biotechnological process for production of a retinoid-mix as defined herein comprising enzymatic conversion of retinal into retinol in the presence of an RDH22 homolog, particularly obtainable from fungi, as defined herein, particularly comprising cultivation of a suitable host cell, more particularly a retinal-producing host cell, expressing said RDH22 homolog under suitable conditions that allow formation of said retinoid-mix as defined herein.

The terms "RDH", "retinal reductase", "retinal reducing enzyme", "enzyme involved in formation of retinol" or "enzyme involved in conversion of retinal into retinol" are used interchangeably herein and refer to enzymes [EC 1.1.1.105] which are involved in the conversion/catalysis of retinal into retinol as well as the back-conversion from retinol to retinal. With regards to RDH22, the formation of dihydroretinoids is reduced to a percentage of less than about 10% detectable in a retinoid-mix formed during a fermentation process using a suitable retinoid-producing host cell and under suitable conditions and the flux towards retinol is increased such that the percentage of retinal present in said retinoid-mix as detectable at the end of the fermentation process is less than about 8% based on total retinoids.

Thus, the present invention is related to RDH22 homologs as defined herein capable of catalyzing retinal into retinol, wherein the conversion towards retinol is increased, leading to a retinoid-mix with a percentage of less than about 8% retinal based on total retinoids, which can be measured at the end of the fermentation process by known methods, particularly process for production of a retinoid-mix with at least about 80% retinyl acetate as described herein.

In one embodiment, the present invention is directed to RDH22 homologs obtainable from *Yarrowia*, preferably

*Yarrowia lipolytica*, comprising YlRDH22 according to SEQ ID NO:1 and enzymes originated from other source organisms or being artificially constructed (based on digital sequence information) but having activity corresponding to the respective *Yarrowia* RDH22 according to SEQ ID NO: 1. Using such YlRDH22 homolog as defined herein in a process comprising production of retinol and retinyl acetate, the percentage of retinal accumulated during such production process and present in the retinoid-mix measured at the end of the production process could be reduced to less than 1% based on total retinoids.

Preferably, the present invention is directed to polypeptides with at least about 30, 35, 40, 45, 50, 55, 60, 65, 70, 75, 80, 85, 90, 92, 95, 97, 98, 99% or up to 100% identity to SEQ ID NO:1 including polynucleotides encoding said polypeptides, such as e.g. polynucleotide according to SEQ ID NO:2 or 3 as well as enzymes having equivalent enzymatic activity, i.e. activity corresponding to YlRDH22 as defined above but are originated from another source organism or being based on digital sequence information, particularly being originated from another fungal organism.

In one embodiment, the present invention is directed to RDH22 homologs obtainable from *Wickerhamomyces*, preferably *Wickerhamomyces anomalus*, comprising WaRDH22 according to SEQ ID NO:4 and enzymes originated from other source organisms or being artificially constructed (based on digital sequence information) but having activity corresponding to the respective *Wickerhamomyces* RDH22 according to SEQ ID NO:4. Using such WaRDH22 homolog as defined herein in a process comprising production of retinol and retinyl acetate, the percentage of retinal accumulated during such production process and present in the retinoid-mix measured at the end of the production process could be reduced to about 2% or less based on total retinoids. with a conversion rate of more than 90% towards formation of retinol.

Preferably, the present invention is directed to polypeptides with at least about 30, 35, 40, 45, 50, 55, 60, 65, 70, 75, 80, 85, 90, 92, 95, 97, 98, 99% or up to 100% identity to SEQ ID NO:4 including polynucleotides encoding said polypeptides, such as e.g. polynucleotide according to SEQ ID NO:5 or 6 as well as enzymes having equivalent enzymatic activity, i.e. activity corresponding to WaRDH22 as defined above but are originated from another source organism or being based on digital sequence information, particularly being originated from another fungal organism.

The RDH22 enzymes as defined herein are catalyzing the conversion of retinal into retinol with a conversion being shifted towards production of retinol, wherein the substrate (i.e. retinal) can be either cis-, trans- or a mix of cis-/trans-retinal in any possible ratio, with a percentage of at least about 80% trans-isomers being preferred. Conversion of said retinal-mix with about 80% trans-retinal would lead to retinol and optionally retinyl acetate with about the same ratio of trans to cis-isomers in a respective retinoid-mix obtained by a process for fermentative production as defined herein, such as starting from beta-carotene using a host cell capable of retinal, retinol and/or retinyl-acetate production. The skilled person knows how to generate retinal from beta-carotene using beta-carotene oxygenases (BCOs), such as exemplified in WO2019057999 or WO2021009194. Enzymes, particularly acetyl transferases (ATFs), more preferably ATF1s, host cells and processes for conversion of retinol into retinyl acetate are known, such as e.g. from WO2019058000 or WO2020141168.

The terms "conversion" "enzymatic conversion or "cleavage" in connection with enzymatic catalysis of substrates such as e.g. beta-carotene, retinal or retinol are used interchangeably herein and refer to the action of the specific enzymes, including but not limited to BCOs, RDHs, particularly RDH22, or ATFs as defined herein involved in formation of retinal, retinol or retinyl acetate.

As used herein, the term "dihydroretinoids" and "13,14-dihydroretinoids" are used interchangeably herein and includes but not limited to dihydroretinol, dihydroretinal, dihydroretinyl acetate that can be detected in a retinoid-mix according to the present invention. The skilled person known how to measure this.

Particularly, the present invention is related to a process for reducing the percentage of by-products including e.g. retinal and dihydroretinoids present in a retinoid-mix as defined herein, particularly wherein a retinoid-producing host cell, such as a retinal/retinol-producing host cell is modified leading to (over) expression of enzymes having RDH22 activity, particularly YlRDH22 or WaRDH22 and homologs thereof as defined herein, wherein the reduction of retinal is in the range of 20 to more than 92%, particularly about 25, 30, 40, 50, 70, 75, 80, 85, 90, 92, 95% or more and/or the reduction of dihydroretinoids is in the range of 20 to more than 97%, particularly about 25, 30, 40, 50, 70, 75, 80, 85, 90, 92, 95, 97% or more as compared to a process using a non-modified host cell, i.e. a host cell that has not been transformed with such heterologous RDH22 polynucleotides as defined herein.

As used herein, a "modified host cell" refers to a host cell or a process wherein the host cell is (over) expressing a heterologous RDH22 homolog as defined herein, including but not limited to host cells modified such that the activity of an endogenous RDH22 homolog as defined herein is increased as compared to the wild-type or non-modified host cell, such as e.g. via expression of 2, 3, 4, or more gene copies of an endogenous gene, i.e. expression of more copies of the respective endogenous gene as occurring in the respective non-modified wild-type host cell. A modified host cell is also known as "recombinant host cell".

As used herein, a "non-modified host cell" or "wild-type host cell"-which is used interchangeably herein—refers to the respective host cell that is not transformed with a heterologous RDH22 homolog as defined herein and/or that is not over-expressing an endogenous RDH22 homolog, such as e.g. an enzyme having YlRDH22 or WaRDH22 activity as defined herein.

Modifications in order to generate a recombinant host cell having increased activity of an RDH22 homolog as defined herein, may include the use of strong promoters, suitable transcriptional- and/or translational enhancers, or the introduction of one or more gene copies into the respective wild-type host cell, leading to increased accumulation of the respective enzymes and the respective products (e.g. retinol, retinyl acetate) in a given time. The skilled person knows which techniques to use in dependence of the host cell. The increase (or reduction) of gene expression can be measured by various methods, such as e.g. Northern, Southern, or Western blot technology as known in the art.

Expression of the novel RDH22 homologs as defined herein can be achieved in any host system, including (micro) organisms, which is suitable for conversion of retinal into retinol (i.e. retinol-producing host cell) and further suitable for conversion of retinol into retinyl acetate (i.e. retinyl-acetate producing host cell) and furthermore suitable for conversion of carotenoid precursors into beta-carotene (i.e. carotenoid-producing host cell) and furthermore suitable for conversion of beta-carotene into retinal (i.e. retinal-producing host cell) and which allows the expression of the enzymes as disclosed herein and as used for such processes. Examples of suitable host cells to be used for the present invention might be selected from bacteria, algae, fungi including yeast, plant or animal cells, such as e.g. fungal host cells including oleaginous yeast cells, such as e.g. *Rhodosporidium, Lipomyces, Saccharomyces* or *Yarrowia*, preferably *Yarrowia*, more preferably *Yarrowia lipolytica* or bacterial host cells including but not limited to *Escherichia* or *Pantoea*. The skilled person knows which genes are suitable in order to express the necessary enzymes involved in carotenoid—and/or retinoid biosynthesis in a suitable host cell. Genes and methods to generate carotenoid-producing host cells are known in the art, see e.g. WO2006102342. Depending on the carotenoid to be produced, different genes might be involved.

As used herein, the term "fungal host cell" particularly includes yeast cells, such as e.g. retinal/retinol/retinyl-acetate-producing yeast cells, comprising *Yarrowia* or *Saccharomyces*. As used herein, the term retinyl-acetate producing host cells" includes host cells, capable of synthesizing retinol and expressing acetyl transferases (ATFs) as defined in e.g. WO2019058001 or WO2020141168 resulting in retinyl acetate with a percentage as defined herein based on total retinoids produced by said host cell. Optionally, such host cell is furthermore capable of producing carotenoids.

Preferably, the host cell expressing an enzyme having activity of YlRDH22 or WaRDH22 as defined herein, including enzymes with at least about 30% identity to YlRDH22 according to SEQ ID NO:1 or WaRDH22 according to SEQ ID NO:4 to be used for fermentative production of a retinoid-mix according to the present invention comprises further modifications enabling the conversion of retinol into retinyl acetate via action/expression of heterologous ATF [EC 2.3.1.84], 20) particularly fungal ATF, comprising a highly conserved partial amino acid sequence of at least 7 amino acid residues selected from [NDEHCS]-H-x(3)-D-[GA] (motifs are in Prosite syntax, as defined in https://prosite.expasy.org/scanprosite/scanprosite_doc.html), wherein "x" denotes an arbitrary amino acid and with the central histidine being part of the enzyme's binding pocket, preferably wherein the 7 amino acid motif is selected from [NDE]-H-x(3)-D-[GA], more preferably selected from [ND]-H-x (3)-D-[GA], most preferably selected from N—H-x (3)-D-[GA] corresponding to position N218 to G224 in the polypeptide according to SEQ ID NO:1 as disclosed in WO2020141168. Examples of such enzymes might be particularly selected from *L. mirantina, L. fermentati, S. bayanus*, or *W. anomalus*, such as disclosed in WO2020141168 or WO2019058001, more preferably said ATFs comprising one or more amino acid substitution(s) in a sequence with at least about 20%, such as e.g. 25, 30, 35, 40, 45, 50, 55, 60, 65, 70, 75, 80, 85, 90, 92, 95, 97, 98, 99% or up to 100% identity to LmATF1 (i.e. SEQ ID NO:1 as disclosed in WO2020141168), wherein the one or more amino acid substitution(s) are located at position(s) corresponding to amino acid residue(s) selected from the group consisting of position 68, 69, 72, 73, 171, 174, 176, 178, 291, 292, 294, 301, 307, 308, 311, 312, 320, 322, 334, 362, 405, 407, 409, 480, 483, 484, 490, 492, 520, 521, 522, 524, 525, 526 and combinations thereof and as particularly exemplified in Table 4 of WO2020141168, most preferably comprising one or more amino acid substitution(s) on positions corresponding to amino acid residue(s) 69, 407, 409, 480, 484, and combinations thereof in SEQ ID NO:1 as disclosed in WO2020141168, even more preferably comprising an amino acid substitution at a position corresponding to residue 69 in the polypeptide according to SEQ ID NO: 1 as disclosed in WO2020141168 leading to asparagine, serine or alanine at said residue, such as e.g. via substitution of histidine by asparagine (H69N), serine (H69S) or alanine (H69A), with preference for H69A, optionally being combined with amino acid substitution at a position corresponding to residue 407 in the polypeptide according to SEQ ID NO:1 as disclosed in WO2020141168 leading to isoleucine at said residue, such as e.g. via substitution of valine by isoleucine (V4071), optionally being combined with an amino acid substitution at a position corresponding to residue 409 in the polypeptide according to SEQ ID NO: 1 as disclosed in WO2020141168 leading to alanine at said residue, such as e.g. via substitution of glycine by alanine (G409A), optionally being combined with amino acid substitution at a position corresponding to residue 480 in the polypeptide according to SEQ ID NO:1 as disclosed in WO2020141168 leading to glutamic acid, lysine, methionine, phenylalanine or glutamine at said residue, such as e.g. via substitution of serine by glutamic acid (S480E), lysine (S480L), methionine (S480M), phenylalanine (S480F) or glutamine (S480Q), optionally being combined with amino acid substitution at a position corresponding to residue 484 in the polypeptide according to SEQ ID NO:1 as disclosed in WO2020141168 leading to leucine at said residue, such as e.g. via substitution of isoleucine by leucine (1484L). Said modified enzyme might be originated from yeast, such as e.g. *L. mirantina, L. fermentati, W. anomalus* or *S. bayanus*, preferably from *L. mirantina*. In a most preferred embodiment, the ATF to be used for the process according to the present invention is a modified ATF1 comprising amino acid substitutions S480Q_G409A_V4071_H69A_1484L and is obtainable from *Lachancea mirantina*, including an enzyme with an identity of at least about 20% to the LmATF1 according to SEQ ID NO:1 as disclosed in WO2020141168.

Suitable culture conditions of a fermentation process according to the present invention include cultivation of the host cell in an aqueous medium in the presence of suitable carbon sources as defined herein, optionally supplemented with appropriate nutrients under aerobic or anaerobic conditions and as known by the skilled person to enable production of a retinoid-mix as defined herein. The fermentation may be conducted in batch, fed-batch, semi-continuous or continuous mode. Particularly, fermentations are run in fed-batch stirred tank reactors. Fermentations can be run for 5 to 14 days, such as e.g. for around 118 h. Fermentation products including but not limited to retinol, retinyl acetate may be harvested from the cultivation at a suitable moment, e.g. when the tank fills due to addition of the feed. The retinoid-mix comprising retinol and acetylated retinoids might be further purified and/or further processed/formulated, to be used in the food, feed, pharma or cosmetic industry. Cultivation and isolation of host cells selected from *Yarrowia* or *Saccharomyces* to be used for production of carotenoids and/or retinoids is described in e.g. WO2008042338.

Carbon sources to be used for the present invention might be selected from linear alkanes, free fatty acids, including triglycerides, particularly vegetable oil, such as e.g. selected from the group consisting of oil originated from corn, soy, olive, sunflower, canola, cottonseed, rapeseed, sesame, safflower, grapeseed or mixtures thereof, including the respective free fatty acids, such as e.g. oleic acid, palmitic acid or linoleic acid. Suitable carbon sources might furthermore be selected from ethanol, glycerol or glucose and mixtures of one or more of the above-listed carbon sources.

Particularly, the present invention is directed to a process for the production of retinoids, in particular a retinoid-mix as defined herein, in a two-phase culture system including an in vitro extraction system, i.e. cultivation in the presence of a lipophilic solvent as defined herein, wherein a retinal-/retinol-/retinyl acetate-producing host cell, preferably oleaginous yeast cell such as e.g. *Yarrowia*, is cultivated under suitable culture conditions such that the retinoid-mix, including retinyl acetate, is accumulated in the lipophilic solvent and optionally extracted/isolated and/or purified from said lipophilic solvent.

Preferred lipophilic solvents to be used for this aspect of the present invention might be selected from isoparaffins including mixtures of alkanes, cycloparaffin, isoalkanes, cycloalkanes, or dodecanes. The solvents might be natural or synthetic ones. Examples of commercially available useful solvents might be selected from Total, e.g. Isane® solvents, Shell, e.g. ShellSolTD or ShellSolT, Exxon Mobile, e.g. Isopar™ fluids, particularly such as e.g. Isopar M, Isopar N, Isopar H, Isopar K, Isopar L, or mixtures with iso-dodecane isomers, as e.g. commercially available under the tradename AC365770010 (Acros Organics).

Preferably, the second phase solvent is selected from isoparaffins, such as e.g. Isopar M, Isopar N, Isopar H, Isopar K, Isopar L, more preferably selected from Isopar L, Isopar M or Isopar N, solvents with equivalent or identical properties but from other suppliers, wherein said solvents are preferably not being consumed or evaporated during the fermentation process, and/or wherein the color of the produced retinyl acetate is transparent.

In one particular embodiment, the host cell to be used for production of a retinoid-mix according to the present invention comprises further modifications, such as modification in endogenous enzyme activities leading to conversion of retinol into fatty acid retinyl esters (FAREs). Particularly, such modifications include reduction or deletion of endogenous lipase activities as dependent on the corresponding host cell, particularly reduction or deletion of activity of one or more endogenous gene(s) encoding enzymes with activity equivalent to *Yarrowia* LIP2 and/or LIP3 and/or LIP4 and/or LIP8, being reduced or abolished, such as polypeptides with at least about 50%, such as 60, 70, 80, 90, 95, 98, or 100% identity to SEQ ID NO:7, 9, 11, 13, or combinations thereof as disclosed in WO2021136689, wherein SEQ ID NO:7 of WO2021136689 corresponds to LIP2 obtainable from *Yarrowia lipolytica*, SEQ ID NO:9 of WO2021136689 corresponds to LIP3 obtainable from *Yarrowia lipolytica*, SEQ ID NO:11 of WO2021136689 corresponds to LIP4 obtainable from *Yarrowia lipolytica*, SEQ ID NO:13 of WO2021136689 corresponds to LIP8 obtainable from *Yarrowia lipolytica*. Preferably, the process as defined herein comprising an RDH22 homolog as described herein is modified in the activity of a lipase corresponding to activity of *Yarrowia* LIP8, such as particularly with reduced or abolished activity, more particularly abolished LIP8 activity, including reduced or abolished activity of a gene encoding a lipase with activity corresponding to LIP8 activity from *Yarrowia lipolytica*, more preferably wherein a polypeptide with at least about 50% identity to SEQ ID NO:13 of WO2021136689 is abolished. A process for reduction of FARE using a host cell with reduced lipase activity is known from e.g. WO2021136689.

The term "lipase" is used interchangeably herein with the term "enzyme having lipase activity". It refers to enzymes involved in pre-digestion of triglyceride oils such as e.g. vegetable oil into glycerol and fatty acids that are normally expressed in oleaginous host cells. Suitable enzymes to be modified in a host cell as defined herein might be selected from endogenous enzymes belonging to EC class 3.1.1.-, including, but not limited to one or more enzyme(s) with activities corresponding to *Yarrowia* LIP2, LIP3, LIP4, or LIP8 activities.

As used herein, an enzyme having "reduced or abolished" activity means a decrease in its specific activity, i.e. reduced/abolished ability to catalyze formation of a product from a given substrate. A reduction by 100% is referred herein as abolishment of enzyme activity, achievable e.g. via deletion, insertions, frameshift mutations, missense mutations or premature stop-codons in the endogenous gene encoding said enzyme or blocking of the expression and/or activity of said endogenous gene(s) with known methods.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent 20) sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity.

The enzymes as described herein to be expressed in a suitable host cell to be used in the present invention also encompass enzymes carrying (further) amino acid substitution(s) which do not alter enzyme activity, i.e. which show the same properties with respect to the enzymes defined herein. Such mutations are also called "silent mutations". Examples of silent mutations included in the present invention are host-optimized sequences, including but not limited to SEQ ID NO: 3 or 6.

Thus, in a preferred embodiment the present invention is related to production of a retinoid-mix as defined herein, comprising a percentage of dihydroretinoids of less than about 10% based on total retinoids, comprising a percentage of at least about 80% retinyl acetate based on total retinoids, comprising a percentage of less than about 8% retinal based on total retinoids, wherein the process is conducted in *Yarrowia lipolytica*, particularly wherein endogenous lipase activities are reduced or completely abolished, such as e.g. activity of LIP8, furthermore comprising reduction or complete abolishment of lipase activities including endogenous LIP2, and/or LIP3, and/or LIP4, said host cell furthermore expressing a heterologous ATF1 homolog, preferably fungal ATF1 with activity of LmATF1, LfATF1, LffATF1, SbATF1 as e.g. disclosed in WO2019058001 or a modified ATF1 comprising amino acid substitutions S480Q_G409A_V4071_H69A_1484L such as obtainable from *Lachancea mirantina*, including an enzyme with an identity of at least about 20% to the LmATF1 according to SEQ ID NO:1 as disclosed in WO2020141168, and wherein said host cell comprises and expresses an RDH22 homolog as defined herein, such as e.g. RDH22 with at least about 30% identity to SEQ ID NO:1 or 4.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain *Lachancea mirantina* is a synonym of strain *Zygosaccharomyces* sp. IFO 11066, originated from Japan.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in μmol substrate consumed or product formed per min per mg of protein. Typically, μmol/min is abbreviated by U (=unit). Therefore, the unit definitions for specific activity of μmol/min/(mg of protein) or U/(mg of protein) are used interchangeably throughout this document.

An enzyme is active, if it performs its catalytic activity in vivo, i.e. within the host cell as defined herein or within a suitable (cell-free) system in the presence of a suitable substrate. The skilled person knows how to measure enzyme activity. Analytical methods to evaluate the capability/enzymatic activity of a suitable enzyme involved in retinoid production are known in the art, such as e.g. described in Example 4 of WO2014096992. In brief, titers of products such as dihydroretinoids, retinyl acetate, retinol, retinal, beta-carotene, and the like can be measured by HPLC.

As used herein, an enzyme is "expressed and active in vivo" if mRNA encoding for the protein can be detected by Northern blotting and/or protein is detected by mass spectrometry. With regards to the lipase activity as defined herein it means ability of the host cell to utilize triglycerides according to the definition herein. With regards to ATFs as defined herein it means ability of a host cell for acetylation of retinol into retinyl acetate. With regards to RDH activity as defined herein it means ability of a host cell for conversion of retinal into retinol.

Retinoids as used herein include beta-carotene cleavage products also known as apocarotenoids, including but not limited to retinal, retinolic acid, retinol, retinoic methoxide, retinyl acetate, retinyl esters, 4-keto-retinoids, 3 hydroxy-retinoids, dihydroretinoids or combinations thereof. A mixture comprising one or more of said beta-carotene cleavage products, particularly retinal, retinol, retinyl acetate, and/or dihydroretinoid is defined herein as "retinoid-mix" or "total retinoids", wherein said retinoids are accumulated during the fermentation process with typical measurement at the end of fermentation process. Biosynthesis of retinoids is described in e.g. WO2008042338.

A host cell capable of production of retinoids/retinoid-mix as defined herein in e.g. a fermentation process is known as "retinoid-producing host cell" and includes a host cell producing e.g. retinal, retinol and/or retinyl acetate. As used herein, a "retinal-producing host cell" is a host cell wherein the respective polypeptides are expressed and active in vivo, leading to production of retinal, e.g. via enzymatic conversion of beta-carotene into retinal. As used herein, a "retinol-producing host cell" is a host cell, wherein the respective polypeptides are expressed and active in vivo, leading to production of retinol, e.g. via enzymatic conversion of retinal into retinol. A "retinyl acetate-producing host cell" is the respective host cell capable of acetylation of retinol into retinyl acetate via expression of the respective acetylating enzymes, e.g. ATFs, preferably ATF1 enzymes, as described herein.

"Retinal" as used herein is known under IUPAC name (2E,4E,6E,8E)-3,7-Dimethyl-9-(2,6,6-trimethylcyclohexen-1-yl) nona-2,4,6,8-tetraenal. It is herein interchangeably referred to as retinaldehyde or vitamin A aldehyde and includes both cis- and trans-isomers, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

"Vitamin A" as used herein may be any chemical form of vitamin A found in aqueous solutions, in solids and formulations, and includes retinol, retinyl acetate and retinyl esters. It also includes retinoic acid, such as for instance undissociated, in its free acid form or dissociated as an anion. A preferred form of vitamin A is retinyl acetate, wherein the terms "retinyl acetate", "retinol acetate" and "vitamin A acetate" might be used interchangeably (see https://www.cancer.gov/publications/dictionaries/cancer-drug/def/retinyl-acetate?redirect=true).

The terms "triglycerides" and "triglyceride oils" are used interchangeably herein. "FAREs" or "retinyl fatty esters" as used interchangeably herein includes long chain retinyl esters. These long chain retinyl esters define hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to linoleic acid, oleic acid, or palmitic acid.

Particularly, the present invention features the following embodiments 1 to 14:

Embodiment 1: Process for production of a retinoid mix comprising dihydroretinoids, retinal, retinol, and retinyl acetate, wherein the percentage of dihydroretinoids in said mix is less than about 10% or based on total retinoids.

Embodiment 2: Process of embodiment 1, wherein the percentage of retinyl acetate in said mix is at least about 80% based on total retinoids.

Embodiment 3: Process of embodiment 1 or 2, wherein the percentage of retinyl acetate in said mix is at least about 80% based on total retinoids.

Embodiment 4: Process of embodiment 1, 2, or 3, wherein said mix comprises trans and cis-isomers and wherein the percentage of trans-isomers is of at least 80% based on total cis and trans-isomers in said mix.

Embodiment 5: Process of embodiment 4, wherein the percentage of trans-retinyl acetate in said mix is at least about 80%.

Embodiment 6: Process of embodiment 1, 2, 3, 4, or 5, wherein said mix comprising dihydroretinal, dihydroretinol and dihydroretinyl acetate.

Embodiment 7: A retinol-producing host cell expressing a retinol dehydrogenase 22 (RDH22) homolog with at least about 30% identity to a polynucleotide according to SEQ ID NO:1 or 4, wherein the host cell has been transformed with a polynucleotide encoding said RDH22 homolog.

Embodiment 8: Retinol-producing host cell of embodiment 7, wherein the RDH22 homolog is obtained from *Yarrowia* or *Wickerhamomyces.*

Embodiment 9: Use of the retinol-producing host cell of embodiment 7 or 8 in a process according to embodiment 1, 2, 3, 4, 5, or 6.

Embodiment 10: Use of a RDH22 homolog with at least about 30% identity to a polynucleotide according to SEQ ID NO:1 or 4 in a process according to embodiment 1, 2, 3, 4, 5, or 6, wherein the RDH22 homolog is expressed in a suitable retinol-producing host cell.

Embodiment 11: Use of RDH22 homolog having activity of YlRDH22 according to SEQ ID NO:1 in a fermentative production of a retinoid-mix with at least about 80% retinyl acetate within said mix using a suitable retinyl acetate producing host cell, wherein the percentage of retinal within said mix and accumulated during said process is reduced to less than 1% based on total retinoids and measured at the end of the production process.

Embodiment 12: Use of RDH22 homolog having activity of WaRDH22 according to SEQ ID NO:4 in a fermentative production of a retinoid-mix with at least about 80% retinyl acetate within said mix using a suitable retinyl acetate producing host cell, wherein the percentage of retinal within said mix and accumulated during said process is reduced to about 2% or less based on total retinoids and measured at the end of the production process.

Embodiment 13: Process according to embodiment 1, 2, 3, 4, 5, or 6, wherein a host cell according to embodiment 7 or 8 is cultivated in the presence of a lipophilic solvent.

Embodiment 14: Process according to embodiment 13, wherein the retinoid mix is accumulated in the lipophilic solvent and optionally extracted from the lipophilic solvent.

The following examples are illustrative only and are not intended to limit the scope of the invention in any way. The contents of all references, patent applications, patents, and published patent applications, cited throughout this application are hereby incorporated by reference, particularly WO2019057999, WO2021009194, WO2020141168, WO2019058000, WO2019058001, WO2006102342, WO2008042338, WO2021136689, WO2014096992, WO2016172282.

EXAMPLES

Example 1: General Methods and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake plate assay. Typically, 200 µl of 0.075% Yeast extract, 0.25% peptone (0.25X YP) is inoculated with 10 µl of freshly grown *Yarrowia* and overlaid with 200 µl of Isopar M with 2% oleic acid as a carbon source. Clonal isolates of transformants were grown in 24 well plates (Multitron, 30° C., 800 RPM) in YPD media with Isopar M overlay indicated earlier for 4 days. The overlay fraction was removed from the shake plate wells and analyzed by HPLC on a normal phase column, with a photo-diode array detector.

DNA transformation. Strains were transformed by overnight growth on YPD plate media; 50 µl of cells were scraped from a plate and transformed by incubation in 500 µl with 1 µg transforming DNA, typically linear DNA for integrative transformation, 40% PEG 3550MW, 100 mM lithium acetate, 50 mM Dithiothreitol, 5 mM Tris-Cl pH 8.0, 0.5 mM EDTA for 60 minutes at 40° C. and plated directly to selective media or in the case of dominant antibiotic marker selection the cells were out grown on YPD liquid media for 4 hours at 30° C. before plating on the selective media. Nourseothricin (Nat) selection was performed on YPD media containing 100 µg/mL nourseothricin and hygromycin (Hyg) selection was performed on YPD containing 100 µg/mL hygromycin. URA3 marker recycling was performed using 5-fluoroorotic acid (FOA). Episomal hygromycin resistance marker (Hyg) plasmids were cured by passage on non-selective media, with identification of Hyg-sensitive colonies by replica plating colonies from non-selective media to hygromycin containing media (100 µg/mL).

DNA molecular biology. Plasmid MB9523 containing expression systems for DrBCO, LmATF-S480Q_G409A_V4071_H69A_1484L, and FfRDH (SEQ ID NO:8) was synthesized at Genscript (Piscataway, NJ, USA). Plasmid MB9523 contains the 'URA3' for marker selection in *Yarrowia lipolytica* transformations. Genes were synthesized with Nhel and Mlul ends in pUC57 vector. Typically, the genes were subcloned to the MB5082 'URA3', MB6157 HygR, and MB8327 NatR vectors for marker selection in *Yarrowia lipolytica* transformations, as in WO2016172282. For clean gene insertion by random nonhomologous end joining of the gene and marker Hindlll/Xbal (for MB5082-based vectors (all marked with URA3 in Table 1, except MB9523), Pvull (for MB6157—and MB8327-based vectors), or Sfil (for MB9523), respectively purified by gel electrophoresis and Qiagen gel purification column. Clones were verified by sequencing. Typically, genes are synthesized by a synthetic biology at GenScript (Piscataway, NJ). Plasmid MB8388-LIP8 (SEQ ID NO: 9), containing a Cas9, and guide RNA expression systems to target LIP8, was synthesized at Genscript (Piscataway, NJ, USA).

Plasmid list. Plasmid, strains, nucleotide and amino acid sequences that were used are listed in Table 1, 2, 6 and the sequence listing. In general, all non-modified sequences referred to herein are the same as the accession sequence in the database for reference strain CLIB122 (Dujon B, et al, Nature. 2004 Jul. 1;430 (6995): 35-44).

TABLE 1 list of plasmids used for construction of the strains for overexpression or deletion of the respective genes indicated as "insert". "LmATF1-mut" refers to Lachancea mirantina (LmATF1; SEQ ID NO: 13 in WO2019058001) carrying aa substitutions S480Q_G409A_V4071_H69A_1484L. "DrBCO" refers to BCO originated from Danio rerio (see SEQ ID NO: 16 in WO2020141168); "FfRDH" refers to RDH originated from Fusarium (see SEQ ID NO: 22 in WO2020141168). For more explanation, see text.

| Plasmid | Insert | Marker | SEQ ID NO: |
|---|---|---|---|
| MB7452 | Cas9 | Nat | 7 |
| MB9523 | DrBCO; LmATF1-mut; FfRDH | URA3 | 8 |
| MB8388-LIP8 | Cas9; LIP8 targeting guide RNAs | Hyg | 9 |
| MB8203 | Homo sapiens RDH12 (HsRDH12) | URA3 | 10 |
| MB9894 | YALIOF29821p (YlRDH22) | URA3 | 11 |
| MB9997 | Wickerhamomyces anomalus RDH22 (WaRDH22) | URA3 | 12 |

TABLE 2 list of Yarrowia lipolytica strains used. Construction of ML17544 is described in Table 2 of WO2020141168. For more details, see text.

| Strain | Description |
|---|---|
| ML18812 | ML17544 transformed with MB9523 |
| ML18812-lip8 | ML18812 with MB7542 and MB8388-LIP8, lip8 deletion |
| ML18812-lip8 + MB9894 | ML18812-lip8 cured on FOA with MB9894 |
| ML18812-lip8 + MB8203 + MB9894 | ML18812-lip8 + MB8203 cured on FOA, transformed with MB9894 |

Normal phase retinol method. A Waters 1525 binary pump attached to a Waters 717 auto sampler were used to inject samples. A Phenomenex Luna 3μ Silica (2), 150×4.6 mm with a security silica guard column kit was used to resolve retinoids. The mobile phase consists of either, 1000 mL hexane, 30 mL isopropanol, and 0.1 mL acetic acid for astaxanthin related compounds, or 1000 mL hexane, 60 mL isopropanol, and 0.1 mL acetic acid for zeaxanthin related compounds. The flow rate for each was 0.6 mL per minute. Column temperature was ambient. The injection volume was 20 μL. The detector was a photodiode array detector collecting from 210 to 600 nm. Analytes were detected according to Table 3.

TABLE 3 list of analytes using normal phase retinol method. "RT" means retention time. For more details, see text.

| Intermediates | RT [min] | Lambda max [nm] |
|---|---|---|
| 11-cis-dihydro-retinol | 7.1 | 293 |
| 11-cis-retinal | 4 | 364 |
| 11-cis-retinol | 8.6 | 318 |
| 13-cis-retinal | 4.1 | 364 |
| dihydro-retinol | 9.2 | 292 |
| retinyl-acetate | 3.5 | 326 |
| retinyl-ester | 3 | 325 |
| trans-retinal | 4.7 | 376 |
| trans-retinol | 10.5 | 325 |

Sample preparation. Samples were prepared by various methods depending on the conditions. For whole broth or washed broth samples the broth was placed in a Precellys® tube weighed and mobile phase was added, the samples were processed in a Precellys® homogenizer (Bertin Corp, Rockville, MD, USA) on the highest setting 3X according to the manufactures directions. In the washed broth the samples were spun in a 1.7 ml tube in a microfuge at 10000 rpm for 1 minute, the broth decanted, 1 ml water added mixed pelleted and decanted and brought up to the original volume the mixture was pelleted again and brought up in appropriate amount of mobile phase and processed by Precellys® bead beating. For analysis of mineral oil fraction, the sample was spun at 4000 RPM for 10 minutes and the oil was decanted off the top by positive displacement pipet (Eppendorf, Hauppauge, NY, USA) and diluted into mobile phase mixed by vortexing and measured for retinoid concentration by HPLC analysis.

Fermentation conditions. Fermentations were identical to the previously described conditions using Isopar M overlay and stirred tank that was ethanol fed in a bench top reactor with 0.5L to 5L total volume (see WO2016172282). Generally, the same results were observed with a fed batch stirred tank reactor with an increased productivity demonstrating the utility of the system for the production of retinoids.

Example 2: Production of Retinoids in *Yarrowia lipolytica*

Strains were grown in the shake plate assay described in Example 1. Addition of plasmids MB9894 (SEQ ID NO:11) or MB9997 (SEQ ID NO:12) to strain ML18812-lip8 improved total retinoid production, when compared to the parental strain which did not contain YlRDH22 or WaRDH22 expression cassettes. Addition of the HsRDH12 expression plasmid MB8203 (SEQ ID NO:10) into strain ML18812-lip8+MB9894 (which results in strain ML18812-lip8+MB8203+MB9894) resulted in a further increased retinoid output. In addition, introduction of MB9894 or MB9997 to ML18812-lip (to make ML18812-lip8+MB9894) reduced the retinal content. The strain ML18812-lip8+MB9894+MB8203 displayed a further reduction of the relative retinal content of the retinoids, and improved the purity of the retinyl acetate, when compared to the parental strain which did not have them. The results are shown in Table 4.

TABLE 4 retinoid production in strain ML18812-lip8 (see Table 2) as control compared to said strain carrying plasmids as indicated. "% total retinoids" is the percentage of retinoids produced compared to total retinoids in the control without addition of plasmids, wherein the total retinoids obtained with the control is set to 100%. "% retinal" means percentage of retinal in the retinoid mix based on total retinoids. For more explanation, see text.

| Strain | % total retinoids | % retinal |
|---|---|---|
| ML18812-lip8 | 100 | 8.2 |
| ML18812-lip8 + MB9894 | 114.6 | 0.95 |
| ML18812-lip8 + MB8203 + MB9894 | 136 | 0.6 |
| ML18812-lip8 + MB9997 | 110 | 2.0 |

Example 3: RDH Expression Diminishes Dihydroretinoid Production

Strains were fermented as described in Example 1, and broth samples were quantified for dihydroretinoid compounds, the results are shown in Table 5. Addition of either HsRDH12 (MB8203), WaRDH22 (MB9997), or YlRDH22 to ML18812-lip8 reduces both retinal and dihydroretinoid fraction, while adding both HsRDH12 and YlRDH22 (MB9894) reduces it further still. Also, addition of either HsRDH12, WaRDH22, YlRDH22, or both HsRDH12 and YlRDH22 increases retinyl acetate purity.

TABLE 5 retinoid production in strain ML18812-lip8 (see Table 2) as control compared to said strain carrying plasmids as indicated, including the purity with regards to retinyl acetate, retinal and dihydroretinoids. The percentages given are based on total retinoids in the mixture. For more explanation, see text.

| Strain | % retinyl acetate | % dihydro-retinoids |
|---|---|---|
| ML18812-lip8 | 73 | 10.2 |
| ML18812-lip8 + MB9894 | 83 | 0.3 |
| ML18812-lip8 + MB8203 + MB9894 | 92 | 0.6 |
| ML18812-lip8 + MB9997 | 91 | 1.98 |

TABLE 6 list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| YlRDH22 (aa) | MTRSKFTEYKQVLRNSCVGKPQYTEKDYPDLDGKNFLVTGATGGVGLEATKLL<br>LEKKSHVIMVGRSKTKSQSTLDELOKTYSHGTFDFVEADLSDLTTVERAGEYI<br>RSKYTTLDGAILNAGVMAPPYSLTPQGHESQWGINVVAHFLLSKYISPALISA<br>AQTAPKDTVRLVWVSSSVVAMSPYEGGIKFDDINHSKVKNPSPWTLYSQSKIG<br>DAYLAYLWSKHHPDSGVLSVSLDPGNLASDLSRHTSWLSSIKNYVLYPPKYGA<br>YTELSALLNPSVKNNEHLIPWGIEGHLRQDVDDGRRGKDGEELWQGLNKDVEG<br>FFKEE | 1 |
| YlRDH22 (nt) | ATGACTCGATCCAAGTTCACCGAATACAAACAAGTGCTGCGAAACAGCTGCGT<br>GGGCAAGCCCCAATACACCGAGAAGGATTACCCTGATCTCGACGGAAAGAACT<br>TTCTTGTCACTGGAGCCACTGGAGGAGTTGGTCTGGAGGCCACCAAGCTGCTG<br>CTAGAGAAGAAGAGCCATGTAATCATGGTTGGCCGATCCAAAACAAAGTCTCA<br>GTCTACCCTTGACGAGCTCCAGAAGACATACTCCCACGGTACCTTTGATTTCG<br>TCGAGGCTGATCTGTCTGACCTGACCACTGTGGAGCGAGCCGGAGAGTACATT<br>CGAAGTAAGTACACCACTTTGGACGGTGCCATTCTCAACGCTGGAGTCATGGC<br>TCCCCCCTATAGCCTCACTCCCCAGGGCCACGAGTCTCAATGGGGTATCAATG<br>TGGTTGCCCATTTTCTGCTGTCCAAGTATATCTCTCCTGCTCTGATCTCGGCC<br>GCCCAGACAGCCCCCAAGGACACCGTGCGACTTGTCTGGGTGTCTTCTTCTGT<br>CGTTGCCATGAGTCCTTATGAAGGAGGTATCAAGTTTGACGATATCAACCACT<br>CTAAGGTCAAGAACCCTTCTCCCTGGACCCTTTACTCCCAGTCCAAGATTGGA<br>GATGCTTACCTGGCTTACCTGTGGTCGAAACACCATCCCGATTCTGGCGTCCT<br>GTCCGTCTCTCTGGACCCCGGTAACCTGGCCTCTGATCTGTCCAGACATACTT<br>CTTGGCTCTCCAGCATTAAGAACTACGTGCTGTATCCTCCCAAGTATGGCGCC<br>TACACCGAGCTGTCTGCTCTGCTGAACCCCTCCGTCAAGAATAACGAGCATCT<br>CATTCCCTGGGGTATTGAGGGACACCTTAGACAGGATGTCGACGATGGACGAC<br>GTGGAAAGGACGGAGAAGAGCTCTGGCAGGGTCTCAACAAGGATGTCGAGGGC<br>TTCTTTAAGGAGGAGTAA | 2 |
| YlRDH22 (nt*) | ATGACCCGATCCAAGTTCACCGAGTACAAGCAGGTTCTCCGAAACTCT<br>TGTGTTGGCAAGCCCCAGTACACTGAGAAGGATTACCCCGATCTCGAC<br>GGAAAGAACTTTCTCGTCACTGGTGCTACTGGTGGAGTTGGTCTGGAG<br>GCCACTAAGCTGCTCCTTGAGAAGAAGTCTCACGTTATTATGGTTGGC<br>CGATCTAAGACTAAGTCTCAGTCTACCCTTGACGAGCTTCAGAAGACT<br>TACTCTCACGGTACTTTCGATTTCGTTGAGGCTGATCTCTCTGACCTT<br>ACCACTGTTGAGCGAGCCGGAGAGTACATTCGATCTAAGTACACTACC<br>CTTGACGGTGCCATTCTTAACGCTGGAGTCATGGCTCCCCCCTACTCT<br>CTCACTCCCCAGGGTCACGAGTCTCAGTGGGGTATTAACGTTGTTGCT | 3 |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CACTTTCTCCTGTCTAAGTACATCTCTCCTGCTCTGATTTCTGCTGCT<br>CAGACTGCCCCCAAGGACACCGTTCGACTTGTTTGGGTGTCTTCTTCT<br>GTCGTTGCCATGTCTCCTTACGAGGGAGGTATTAAGTTTGACGATATT<br>AACCACTCTAAGGTCAAGAACCCTTCTCCTTGGACCCTTTACTCTCAG<br>TCTAAGATTGGTGATGCTTACCTGGCTTACCTTTGGTCTAAGCACCAC<br>CCCGATTCTGGAGTCCTTTCTGTCTCTCTGGACCCCGGTAACCTGGCT<br>TCTGATCTCTCTCGACACACTTCTTGGCTTTCTTCTATTAAGAACTAC<br>GTTCTTTACCCTCCCAAGTACGGTGCCTACACTGAGCTGTCTGCTCTT<br>CTCAACCCTTCCGTTAAGAACAACGAGCACCTTATTCCCTGGGGTATT<br>GAGGGACACCTTCGACAGGATGTCGACGATGGTCGACGAGGAAAGGAC<br>GGAGAGGAGCTCTGGCAGGGTCTTAACAAGGATGTCGAGGGTTTCTTT<br>AAGGAGGAGTAA | |
| WaRDH22<br>(aa) | MVNVAYEWLRDCWPPKPEFLPKDYPDLTGKTILITGANTGIGFESAKA<br>LLKKNATVVFANRSEEKTKIAIAKIQAELGGDSSQRSIFVKTDLSDLS<br>SIKGTAEELKSKGITKLHYTILNAGVMQPPKGSKTKQGFELQIGTNVL<br>GHQLLQKFLTPLVLNAVSSDFTPRVVWLASAAHLSSPPNGGIDWDSER<br>NADWAGTVSAYGQSKTGNIYQAYIYAQQHKDVISVSAHPGYLASDLTR<br>AYKGYLQYLMKLLMSPPVYGSYTELFAALSPKVTLKESGRYIGPWGOF<br>RELRDDVQEGLTDGTAQKLWDWAEAEIRPYT | 4 |
| WaRDH22<br>(nt) | ATGGTTAACGTTGCTTATGAATGGCTAAGAGACTGCTGGCCTCCTAAACCTGA<br>ATTCTTACCAAAAGATTATCCAGATTTAACAGGAAAGACAATCTTAATCACTG<br>GTGCCAATACGGGTATTGGGTTTGAAAGTGCTAAAGCCTTGTTGAAGAAAAAC<br>GCAACAGTTGTATTTGCAAATAGAAGCGAAGAGAAGACAAAAATCGCTATTGC<br>CAAAATTCAAGCTGAATTAGGTGGTGATTCATCTCAAAGATCAATTTTCGTCA<br>AGACTGATTTAAGTGATTTATCATCGATCAAGGGCACAGCGGAAGAATTGAAA<br>TCAAAAGGTATCACAAAATTACATTACACCATATTGAATGCTGGTGTTATGCA<br>ACCTCCAAAAGGTTCCAAGACAAAACAAGGATTTGAATTACAAATTGGTACAA<br>ATGTTTTAGGTCATCAATTATTACAAAAATTTCTAACACCATTAGTTTTGAAT<br>GCAGTTTCATCAGATTTCACACCAAGAGTTGTTTGGTTAGCCTCAGCTGCACA<br>TCTTTCATCCCCACCAAATGGTGGTATTGATTGGGATTCCTTCCGTAATGCTG<br>ATTGGGCTGGAACTGTCAGTGCTTATGGTCAATCCAAGACTGGTAATATTTAT<br>CAAGCTTATATCTATGCTCAGCAACATAAAGATGTCATCAGTGTCTCTGCTCA<br>TCCAGGGTATTTGGCTTCTGATTTAACAAGAGCTTATAAAGGTTATCTTCAAT<br>ATTTGATGAAACTCTTGATGTCTCCTCCAGTTTATGGTTCTTATACTGAATTA<br>TTCGCTGCTCTCAGTCCAAAAGTTACATTGAAGGAAAGTGGTAGATATATTGG<br>TCCTTGGGGTCAATTCAGAGAATTGAGAGATGATGTTCAAGAAGGCTTAACTG<br>ATGGAACTGCTCAAAAATTATGGGATTGGGCTGAAGCTGAAATTAGACCATAC<br>ACTTAG | 5 |
| WaRDH22<br>(nt*) | ATGGTTAACGTTGCTTACGAGTGGCTTCGAGACTGCTGGCCCCCTAAGCCTGA<br>GTTCCTCCCTAAGGATTACCCTGACCTCACCGGAAAGACCATCCTTATCACTG<br>GTGCCAACACTGGTATTGGTTTTGAGTCCGCTAAGGCTCTCCTCAAGAAGAAC<br>GCTACCGTTGTTTTTGCCAACCGATCCGAGGAGAAGACTAAGATCGCTATTGC<br>CAAGATTCAGGCTGAGCTTGGTGGTGATTCTTCTCAGCGATCTATTTTCGTCA<br>AGACTGACCTTTCCGATCTCTCTTCCATTAAGGGCACTGCTGAGGAGCTTAAG<br>TCTAAGGGTATCACTAAGCTCCACTACACCATTCTTAACGCTGGTGTTATGCA<br>GCCTCCCAAGGGCTCCAAGACTAAGCAGGGTTTTGAGCTTCAGATTGGTACTA<br>ACGTTCTTGGCCACCAGCTCCTCCAGAAGTTTCTCACTCCCCTTGTTCTCAAC<br>GCTGTTTCTTCTGATTTCACCCCTCGAGTTGTTTGGCTCGCCTCTGCTGCTCA<br>CCTTTCTTCCCCTCCCAACGGTGGTATTGATTGGGATTCCTTCCGAAACGCTG<br>ATTGGGCTGGTACTGTCTCTGCTTACGGTCAGTCTAAGACTGGTAACATTTAC<br>CAGGCTTACATCTACGCTCAGCAGCACAAGGATGTCATCTCTGTCTCTGCTCA<br>CCCCGGATACCTTGCTTCTGATCTCACTCGAGCTTACAAGGGATACCTTCAGT<br>ACCTTATGAAGCTCCTTATGTCTCCTCCCGTTTACGGTTCTTACACTGAGCTT<br>TTCGCTGCTCTTTCTCCCAAGGTTACTCTCAAGGAGTCTGGTCGATACATTGG<br>TCCTTGGGGTCAGTTCCGAGAGCTTCGAGATGACGTTCAGGAGGGCCTTACCG<br>ATGGTACTGCTCAGAAGCTCTGGGATTGGGCTGAGGCTGAGATTCGACCTTAC<br>ACTTAA | 6 |
| MB7452 | CGCGTGGATCGCCGGTGCGTTGACGTTGGTGACCTCCAGCCAGAGGTGCCCGG<br>CGCCCCGCTCGCCGGCGAACTCCGTCGCGAGCCCCATCAACGCGCGCCCGACC<br>CCGTGCCCCCGGTGCTCCGGGGCGACCTCGATGTCCTCGACGGTCAGCCGGCG<br>GTTCCACGCCGAGTACGAGATGACCACGAAGCCCGCCAGGTCGCCGTCGTCCC<br>CGTACGCGACGAACGTCCGGGAGTCCGGGTCGCCGTCCTCCCCGTCGTCCGAT<br>TCGTCGTCCGATTCGTCGTCGGGGAACACCTTGGTCAGGGGCGGGTCCACCGG<br>CACCTCCCGCAGGGTGAAGCCGTCCCCGGTGGCGGTGACGCGGAAGACGGTGT<br>CGGTGGTGAAGGACCCATCCAGTGCCTCGATGGCCTCGGCGTCCCCCGGGACA<br>CTGGTGCGGTACCGGTAAGCCGTGTCGTCAAGAGTGGTCATTTTTGTGTCTAG<br>GTGTTTGTGTTTGGACTGCGATCAGTGAAGAAAAGAAGAGGAAAAATTGTGCA | 7 |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | AGAAATTTTGCTTTCAAGACTTGGCTGATGCAGCAGGGTAACTCTGGGACACA | |
| | GACCTATGTTTGTGGTTAAACTCAATGCACGTGGTACGTGCGTGGAGCGCTTA | |
| | CCCATCCAAGGGTGTGGACATGGAACCGACGGTCCGTGGAGTTGTGTAATGTC | |
| | ATTTTGGCGACTCTTGAAGCAAGGCTATAAAAAAATTGTGTGGCTTGAGTCTT | |
| | ATCGAGCTCGGTCACTACAAGAGTTAATCTTCCTGTCTCAGGCAGACAGGTCA | |
| | GGCAGGGTTACTTTTGGGTGTGCTGTAACTCACTGTATGGCCGTTAGTGCGCA | |
| | TAGACGTTGTACATACTGGACCGAATTGTAGCGTGCTCAATAGGGCCAATAAA | |
| | GCTATTGTAGGGATCCGAATTTTCAGAACCTAATTTATCTGTTACCCGGCCTG | |
| | TGGCTCGCACAGCTTAAAAATGGTCAAACTTTCCCCTTCTTGTCTTTTTTTCC | |
| | TCACATTCATCAGGTTCTTGTCTTGATCTTTCAAGTGAGTATTAATTACCGAC | |
| | CTTGGTTCTTCATTGGGAGAGCATTGGAAGCCGTGGTGCAGCAACCACAAAAC | |
| | GGTTCTTCCCCTTCGATACCTTCTTGCCTGCCTTTCAATACAAGTCGGCTCGA | |
| | TTAGCGGTGGTCGCCCCCGCCAGCGGAGAACATGGAACTAACCCAGAATGAGA | |
| | GCTAAGTGGAGAAAGAAGAGAGTCAGACGACTCAAGCGAAAGCGCCGCAAGGT | |
| | CCGAGCTCGATCCAAATAAGCGGTTTTTAACGGAGATTTAACACTAAATCGAA | |
| | GAACTTTTCCCGTTTCATTTGCGAATGAGCTCGTTAACAAAATCCCCCAGTTT | |
| | TTTTATCCAGCTGTAAGGATTGACATTAGTAATGAATTATTGTTTGGTATATT | |
| | TAAATCTGTAGTTCCTTTCTGTCCGTGTCGGCAACTGTCGTACTCGTGATTTA | |
| | CTTGTATTGACGAATACTTACTGTAGCGCACTCTGCTGCTACTGGTCGTAAGG | |
| | ATGTGCTATTTCGGTGTATGGTGGGTTTTTTGGGGGTCGGAACCGAAGACTGT | |
| | TACACGGGCACGGCTCGTTGTGTACACGCACAGAGCTCTTGCGAGTCATGTTG | |
| | TAGCTAGCTCGTCGTGTTCAGGAACTGTTCGATGGTTCGGAGAGAGTCGCCGC | |
| | CCAGAACATACGCGCACCGATGTCAGCAGACAGCCTTATTACAAGTATATTCA | |
| | AGCAAGTATATCCGTAGGGTGCGGGTGATTTGGATCTAAGGTTCGTACTCAAC | |
| | ACTCACGAGCAGCTTGCCTATGTTACATCCTTTTATCAGACATAACATAATTG | |
| | GAGTTTACTTACACACGGGGTGTACCTGTATGAGCACCACCTACAATTGTAGC | |
| | ACTGGTACTTGTACAAAGAATTTATTCGTACGAATCACAGGGACGGCCGCCCT | |
| | CACCGAACCAGCGAATACCTCAGCGGTCCCCTGCAGTGACTCAACAAAGCGAT | |
| | ATGAACATCTTGCGATGGTATCCTGCTGATAGTTTTTACTGTACAAACACCTG | |
| | TGTAGCTCCTTCTAGCATTTTTAAGTTATTCACACCTCAAGGGGAGGGATAAA | |
| | TTAAATAAATTCCAAAAGCGAAGATCGAGAAACTAAATTAAAATTCCAAAAAC | |
| | GAAGTTGGAACACAACCCCCCGAAAAAAAACAACAAACAAAAAACCCAACAAA | |
| | ATAAACAAAAACAAAATAAATATATAACTACCAGTATCTGACTAAAAGTTCAA | |
| | ATACTCGTACTTACAACAAATAGAAATGAGCCGGCCAAAATTCTGCAGAAAAA | |
| | AATTTCAAACAAGTACTGGTATAATTAAATTAAAAAACACATCAAAGTATCAT | |
| | AACGTTAGTTATTTTATTTTATTTAATAAAAGAAAACAACAAGATGGGCTCAA | |
| | AACTTTCAACTTATACGATACATACCAAATAACAATTTAGTATTTATCTAAGT | |
| | GCTTTTCGTAGATAATGGAATACAAATGGATATCCAGAGTATACACATGGATA | |
| | GTATACACTGACACGACAATTCTGTATCTCTTTATGTTAACTACTGTGAGGCA | |
| | TTAAATAGAGCTTGATATATAAAATGTTACATTTCACAGTCTGAACTTTTGCA | |
| | GATTACCTAATTTGGTAAGATATTAATTATGAACTGAAAGTTGATGGCATCCC | |
| | TAAATTTGATGAAAGATGAAATTGTAAATGAGGTGGTAAAAGAGCTACAGTCG | |
| | TTTTGTTTTGAGATACCATCATCTCTAACGAAATATCTATTAAAAATCTCAGT | |
| | GTGATCATGAGTCATTGCCATCCTGGAAAATGTCATCATGGCTGATATTTCTA | |
| | ACTGTTTACTTGAGATAAATATATATTTACAAGAACTTCCCTTGAAATTAATT | |
| | TAGATATAAAATGTTTGCGGGCAAGTTACTACGAGGAATAAATTATATCTAGA | |
| | GGTTCCGCTTCCTCGCTCACTGACTCGCTGCGCTCGGTCGTTCGGCTGCGGCG | |
| | AGCGGTATCAGCTCACTCAAAGGCGGTAATACGGTTATCCACAGAATCAGGGG | |
| | ATAACGCAGGAAAGAACATGTGAGCAAAAGGCCAGCAAAAGGCCAGGAACCGT | |
| | AAAAAGGCCGCGTTGCTGGCGTTTTTCCATAGGCTCCGCCCCCCTGACGAGCA | |
| | TCACAAAAATCGACGCTCAAGTCAGAGGTGGCGAAACCCGACAGGACTATAAA | |
| | GATACCAGGCGTTTCCCCCTGGAAGCTCCCTCGTGCGCTCTCCTGTTCCGACC | |
| | CTGCCGCTTACCGGATACCTGTCCGCCTTTCTCCCTTCGGGAAGCGTGGCGCT | |
| | TTCTCATAGCTCACGCTGTAGGTATCTCAGTTCGGTGTAGGTCGTTCGCTCCA | |
| | AGCTGGGCTGTGTGCACGAACCCCCCGTTCAGCCCGACCGCTGCGCCTTATCC | |
| | GGTAACTATCGTCTTGAGTCCAACCCGGTAAGACACGACTTATCGCCACTGGC | |
| | AGCAGCCACTGGTAACAGGATTAGCAGAGCGAGGTATGTAGGCGGTGCTACAG | |
| | AGTTCTTGAAGTGGTGGCCTAACTACGGCTACACTAGAAGGACAGTATTTGGT | |
| | ATCTGCGCTCTGCTGAAGCCAGTTACCTTCGGAAAAAGAGTTGGTAGCTCTTG | |
| | ATCCGGCAAACAAACCACCGCTGGTAGCGGTGGTTTTTTTGTTTGCAAGCAGC | |
| | AGATTACGCGCAGAAAAAAAGGATCTCAAGAAGATCCTTTGATCTTTTCTACG | |
| | GGGTCTGACGCTCAGTGGAACGAAAACTCACGTTAAGGGATTTTGGTCATGAG | |
| | ATTATCAAAAAGGATCTTCACCTAGATCCTTTTAAATTAAAAATGAAGTTTTA | |
| | AATCAATCTAAAGTATATATGAGTAAACTTGGTCTGACAGTTACCAATGCTTA | |
| | ATCAGTGAGGCACCTATCTCAGCGATCTGTCTATTTCGTTCATCCATAGTTGC | |
| | CTGACTCCCCGTCGTGTAGATAACTACGATACGGGAGGGCTTACCATCTGGCC | |
| | CCAGTGCTGCAATGATACCGCGAGACCCACGCTCACCGGCTCCAGATTTATCA | |
| | GCAATAAACCAGCCAGCCGGAAGGGCCGAGCGCAGAAGTGGTCCTGCAACTTT | |
| | ATCCGCCTCCATCCAGTCTATTAATTGTTGCCGGGAAGCTAGAGTAAGTAGTT | |
| | CGCCAGTTAATAGTTTGCGCAACGTTGTTGCCATTGCTGCAGGCATCGTGGTG | |
| | TCACGCTCGTCGTTTGGTATGGCTTCATTCAGCTCCGGTTCCCAACGATCAAG | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | GCGAGTTACATGATCCCCCATGTTGTGCAAAAAAGCGGTTAGCTCCTTCGGTC | |
| | CTCCGATCGTTGTCAGAAGTAAGTTGGCCGCAGTGTTATCACTCATGGTTATG | |
| | GCAGCACTGCATAATTCTCTTACTGTCATGCCATCCGTAAGATGCTTTTCTGT | |
| | GACTGGTGAGTACTCAACCAAGTCATTCTGAGAATAGTGTATGCGGCGACCGA | |
| | GTTGCTCTTGCCCGGCGTCAACACGGGATAATACCGCGCCACATAGCAGAACT | |
| | TTAAAAGTGCTCATCATTGGAAAACGTTCTTCGGGGCGAAAACTCTCAAGGAT | |
| | CTTACCGCTGTTGAGATCCAGTTCGATGTAACCCACTCGTGCACCCAACTGAT | |
| | CTTCAGCATCTTTTACTTTCACCAGCGTTTCTGGGTGAGCAAAAACAGGAAGG | |
| | CAAAATGCCGCAAAAAAGGGAATAAGGGCGACACGGAAATGTTGAATACTCAT | |
| | ACTCTTCCTTTTTCAATATTATTGAAGCATTTATCAGGGTTATTGTCTCATGA | |
| | GCGGATACATATTTGAATGTATTTAGAAAAATAAACAAATAGGGGTTCCGCGC | |
| | ACATTTCCCCGAAAAGTGCCACCTGACGTCTAAGAAACCATTATTATCATGAC | |
| | ATTAACCTATAAAAATAGGCGTATCACGAGGCCCTTTCGTCTGGCCTAGGAAG | |
| | CGACTTCCAATCGCTTTGCATATCCAGTACCACACCCACAGGCGTTTGTGCTA | |
| | CTCTACTGATAGCAATAGATGCGTCATAATTGGTTGGCCCGCTGAGCCTCCAC | |
| | AGGATACTATTGCACATACCCTGGTCATGTGCAGATCAGCTCATTTGTGGAGA | |
| | CTCTGGAGTAACTTAGACGACGCCTGGTTCAATTGCCGCAATGTGCGCCCACG | |
| | CAGATAATGTATTGAGGGGTGGAGCGCCTCTTGGGGACTTGCTGTACTTGTAC | |
| | GGGATATTAAACGCACTCAGCAAGACCATGACGTAAAACACACCTACTGTACG | |
| | ATACGTACTGTAGGTATTGTACTCGTACCCGGTACTACAAATAGTACGATACT | |
| | ATACGGAGTGTATTTGTACCTTGATATACGACTGGCGGAGTGAAGAGAAGGAG | |
| | TTGAACAAGACCAGATGGGGATATCAGCCCCAGTGCTTTGTATTACAAGTACG | |
| | AGTACTTAATAGATACTGTAAGGCTATTGATACGGATGGCAGTAAGTCATTGA | |
| | GTAAGCAATTGTGGCCCAGCATCTCCCCTACGTACTTGTACCATACCCCATGG | |
| | AGACACCAATGGTCTTTCACGCACACTGTCGTGTGCTGTATCGCAGAATCGGG | |
| | TGTCCAACCAAATGCCGTTACCCCCACGTCACAGCCGATAGACAGATACACCA | |
| | TCAATACCAGCAGGTTGTATCATGCGGTTGGCTGAAGGTAAGCTGATTGGTCT | |
| | AAAAACTGTAGCTGTCCTAATTCAACGAGCGCTATTTGGGGCCAACCACCTCG | |
| | GCCAAGCGGCCTTTAATCTGCGTGCCCCAGAGGCGTCTAATGAGGCTCTGGCC | |
| | GCCACTGTAGGAGTGTTTCTCTGTGCGCACACGCAGTTTTGAGTTTGGGCGAC | |
| | TTTCCCTTTTTCCCAATTGCGTACACACACAGCTCCGAGCTAAGCGCTGTCCT | |
| | TGAACCTTCTCCCTCTTTTCCCTCTTTTTCTCTTCCCCTTCCCCTCCTCCACA | |
| | TTAAGGCCAAATCCTGAATTGCACCAACTAGTACAACGACAACAATGGACAAG | |
| | AAGTACTCCATCGGTTTGGACATTGGTACTAACTCTGTCGGCTGGGCCGTCAT | |
| | CACCGACGAGTACAAGGTTCCCTCCAAGAAGTTCAAGGTCCTTGGCAACACCG | |
| | ACCGACACTCTATCAAGAAGAACCTGATCGGTGCTCTGCTGTTCGACTCTGGC | |
| | GAGACTGCCGAGGCCACCCGACTGAAGCGAACCGCTCGACGCCGATACACCCG | |
| | ACGAAAGAACCGAATCTGTTACCTCCAGGAGATCTTCAGCAACGAGATGGCTA | |
| | AGGTCGACGACTCCTTCTTCCACCGACTCGAGGAGTCTTTCCTGGTCGAAGAG | |
| | GATAAGAAGCACGAGCGACACCCCATCTTCGGCAACATTGTTGATGAGGTTGC | |
| | CTACCATGAGAAGTACCCCACCATCTACCACCTCCGAAAGAAGCTCGTCGACT | |
| | CCACTGACAAGGCTGACCTCCGACTCATCTACCTTGCTCTCGCCCACATGATC | |
| | AAGTTCCGAGGTCACTTCCTCATTGAGGGTGATCTCAACCCCGACAACTCCGA | |
| | CGTTGACAAGCTGTTCATCCAGCTCGTCCAGACCTACAACCAGCTCTTTGAGG | |
| | AGAACCCTATCAACGCTTCTGGTGTTGACGCCAAGGCCATTCTCTCCGCCCGA | |
| | CTCTCTAAGTCCCGACGACTCGAGAACCTCATTGCCCAGCTGCCCGGCGAGAA | |
| | GAAGAACGGCCTCTTCGGTAACCTGATTGCTCTCTCTCTTGGTCTGACCCCCA | |
| | ACTTCAAGTCCAACTTTGACCTCGCCGAGGACGCCAAGCTCCAGCTGTCCAAG | |
| | GACACCTACGATGACGATCTGGACAACCTCCTGGCCCAGATCGGTGACCAGTA | |
| | CGCCGATCTCTTCCTTGCCGCCAAGAACCTCTCCGACGCCATCCTGCTCTCCG | |
| | ACATCCTCCGAGTCAACACCGAGATTACCAAGGCTCCTCTGTCTGCCTCTATG | |
| | ATCAAGCGATACGACGAGCACCACCAGGATCTCACTCTTCTCAAGGCTCTCGT | |
| | CCGACAGCAGCTCCCCGAGAAGTACAAGGAGATTTTCTTTGACCAGTCCAAGA | |
| | ACGGTTACGCTGGCTACATTGACGGTGGTGCTTCCCAGGAAGAGTTTTACAAG | |
| | TTCATCAAGCCTATTCTGGAGAAGATGGACGGTACCGAGGAGCTGCTCGTCAA | |
| | GCTCAACCGAGAGGACCTCCTTCGAAAGCAGCGAACCTTCGATAACGGCTCCA | |
| | TCCCCCACCAGATCCACCTGGGTGAGCTCCACGCCATTCTCCGAAGACAAGAG | |
| | GACTTCTACCCCTTCCTAAAGGATAACCGAGAGAAGATCGAGAAGATTCTCAC | |
| | CTTCCGAATCCCCTACTACGTCGGTCCCCTCGCTCGAGGTAACTCCCGATTTG | |
| | CTTGGATGACCCGAAAGTCCGAGGAGACTATCACCCCCTGGAACTTTGAAGAG | |
| | GTAGTCGACAAGGGTGCCTCCGCCCAGTCTTTCATTGAGCGGATGACCAACTT | |
| | CGATAAGAACCTCCCCAACGAGAAGGTCCTTCCCAAGCACTCTCTCCTCTACG | |
| | AGTACTTCACCGTCTACAACGAGCTGACCAAGGTCAAGTACGTTACCGAGGGC | |
| | ATGCGAAAGCCCGCTTTCCTCTCTGGTGAGCAGAAGAAGGCCATTGTCGACCT | |
| | CCTGTTCAAGACTAACCGAAAAGTCACCGTCAAGCAGCTCAAGGAAGACTACT | |
| | TCAAGAAGATTGAGTGCTTCGACTCCGTCGAGATTTCCGGTGTCGAGGACCGA | |
| | TTCAACGCCTCCCTCGGCACCTACCACGATCTTCTGAAGATCATCAAGGACAA | |
| | GGACTTTCTTGATAACGAGGAGAACGAGGACATTCTCGAGGACATCGTCCTCA | |
| | CCCTCACCCTTTTCGAGGATCGAGAGATGATCGAGGAGCGACTCAAGACCTAC | |
| | GCCCATCTCTTCGACGACAAGGTCATGAAGCAACTCAAGCGACGACGATACAC | |
| | TGGCTGGGGCCGACTTTCCCGAAAGCTCATCAACGGCATCCGAGACAAGCAGT | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CTGGCAAGACCATCCTGGACTTCCTGAAGTCCGACGGTTTCGCCAACCGAAAC<br>TTCATGCAGCTCATCCACGACGACTCTCTTACCTTCAAAGAGGATATCCAGAA<br>GGCCCAGGTTTCTGGCCAGGGCGACTCCCTCCACGAGCACATTGCCAACCTCG<br>CCGGATCCCCCGCCATCAAAAAGGGTATCCTCCAGACCGTCAAGGTTGTCGAC<br>GAACTCGTGAAGGTCATGGGCCGACACAAGCCCGAGAACATCGTTATCGAGAT<br>GGCCCGAGAGAACCAGACCACCCAGAAGGGTCAGAAGAACTCCCGAGAGCGAA<br>TGAAGCGAATCGAAGAGGGTATCAAGGAGCTCGGTTCCCAGATTCTCAAGGAG<br>CACCCCGTCGAGAACACCCAGCTCCAGAACGAGAAACTCTACCTGTACTACCT<br>CCAGAATGGCCGAGACATGTACGTTGACCAGGAGCTCGACATCAACCGACTCT<br>CCGACTACGACGTCGACCACATTGTTCCTCAGTCCTTCCTCAAGGACGACTCC<br>ATCGACAACAAGGTTCTGACCCGATCTGACAAGAACCGAGGTAAGTCCGACAA<br>CGTTCCCTCCGAAGAGGTCGTTAAGAAGATGAAGAACTACTGGCGACAGCTTC<br>TCAACGCCAAACTGATCACCCAGCGAAAGTTTGACAACCTCACCAAGGCCGAG<br>CGAGGTGGTCTGTCCGAGCTGGACAAGGCCGGCTTCATTAAGCGACAGCTGGT<br>CGAGACTCGACAGATCACCAAGCACGTCGCCCAGATCCTCGACTCCCGAATGA<br>ACACCAAGTACGACGAGAACGACAAGCTCATCCGGGAGGTCAAGGTCATCACC<br>CTGAAGTCTAAGCTTGTCTCCGACTTCCGAAAGGACTTCCAGTTCTACAAGGT<br>CCGAGAGATCAACAACTACCACCACGCCCACGACGCCTACCTCAACGCCGTTG<br>TTGGTACCGCCCTCATCAAGAAGTATCCCAAGCTCGAGTCCGAGTTCGTTTAC<br>GGCGACTACAAGGTTTACGATGTCCGAAAGATGATTGCCAAGTCCGAGCAGGA<br>GATCGGTAAGGCCACCGCCAAGTACTTTTTCTACTCCAACATCATGAATTTCT<br>TCAAGACCGAGATCACTCTCGCCAACGGTGAGATTCGAAAGCGACCCCTGATT<br>GAGACTAATGGTGAGACTGGTGAGATCGTCTGGGATAAGGGCCGAGACTTCGC<br>CACCGTCCGAAAGGTCCTGTCCATGCCCCAGGTCAACATTGTCAAGAAGACCG<br>AGGTCCAGACCGGTGGCTTCTCCAAGGAGTCCATTCTCCCCAAGCGAAACTCC<br>GACAAACTCATCGCCCGTAAGAAGGACTGGGATCCGAAGAAGTACGGTGGTTT<br>CGATTCTCCCACCGTTGCCTACTCCGTCCTCGTTGTTGCTAAAGTCGAGAAGG<br>GTAAGTCTAAGAAACTCAAGTCCGTGAAGGAGCTACTCGGTATCACCATCATG<br>GAGCGATCTTCTTTTGAGAAGAACCCCATTGACTTCCTCGAGGCCAAGGGTTA<br>CAAAGAGGTCAAGAAGGACCTGATTATCAAGCTGCCCAAGTACTCCCTCTTTG<br>AGCTCGAGAACGGCCGAAAGCGAATGCTGGCTTCCGCTGGTGAGCTGCAGAAG<br>GGCAACGAGCTCGCTCTGCCCTCCAAGTACGTCAACTTCCTCTACCTGGCCTC<br>CCACTACGAGAAGCTCAAGGGCTCCCCCGAGGACAACGAGCAGAAGCAGCTGT<br>TCGTTGAGCAGCACAAGCACTACCTCGACGAGATCATCGAGCAGATCTCCGAG<br>TTCTCCAAGCGAGTCATCCTCGCTGACGCCAACCTTGATAAGGTTCTCTCTGC<br>TTACAACAAGCACCGGGACAAGCCCATCCGAGAGCAGGCCGAGAATATCATCC<br>ACCTCTTCACTCTCACCAACCTCGGCGCTCCTGCTGCCTTCAAGTACTTCGAC<br>ACCACCATTGACCGAAAGAGGTACACCTCCACCAAGGAAGTCCTCGACGCCAC<br>CCTGATCCACCAGTCCATCACCGGCCTCTACGAAACCCGAATCGACCTCTCCC<br>AGCTCGGCGGTGACTCTCGAGCCGACCCCAAGAAGAAGCGAAAAGTCTAAATA<br>TCCGAAGATCAAGAGCGAAGCAAGTTGTAAGTCCAGGACATGTTTCCCGCCCA<br>CGCGAGTGATTTATAACACCTCTCTTTTTTGACACCCGCTCGCCTTGAAATTC<br>ATGTCACATAAATTATAGTCAACGACGTTTGAATAACTTGTCTTGTAGTTCGA<br>TGATGATCATATGATTACATTAATAGTAATTACTGTATTTGATATATATACTA<br>ATTACAATAGTACATATTAGAACATACAATAGTTAGTGCCGTGAAGTGGCTTA<br>AAATACCGCGAGTCGATTACGTAATATTATTACCTCTTGCCCATCGAACGTAC<br>AAGTACTCCTCTGTTCTCTCCTTCCTTTGCTTTGTGCACGAAGAACTGCGGTC<br>AGGTGACACAACTTTTTCCATCTCAGGGTGTGTCGCGTGTGCTTCATCCAAAC<br>TTTAGTTGGGGTTCGGGTTCGCGCGAGATGATCACGTGCCCTGATTTGGTGTC<br>GTCCCCCGTCGCGCTGCGCACGTGATTTATTTATTTCCGGTGGCTGCTGTCTA<br>CGCGGGGCCTTCTCTGCCCTTCTGTTTCAACCTTCGGGCGGTTCTCGTAACCA<br>GCAGTAGCAATCCATTTCGAAACTCAAAGAGCTAAAAACGTTAAACCTCAGCA<br>GTCGCTCGACGAATGGGCTGCGGTTGGGAAGCCCACGAGGCCTATAGCCAGAG<br>CCTCGAGTTGACAGGAGCCCAGACGCCTTTTCCAACGGCAACTTTTATATAAA<br>ATGGCAATGTATTCATGCAATTGCGGCCGTGTCAGGTTGGAGACACTGGACCA<br>CACTCTCCATTGCTTCCTGAGGAGATGGATCATTGCTAGTGCATCTACGCGCA<br>GCAATCCCGCAAGCTCGACAACCGTAGATGGGCTTTGGTGGGCCAATCAATTA<br>CGCAACCCGCACGTTAAATTGTATGAGGAAGGAAGGCCACGGTACAAAGTGGG<br>TGGTCTTCACCCAGTGGTTGTTGGTGGCGTCATGCAGACCATGGCCGCCAGTG<br>TGCTGGAATTGAATATTTACCGTTCGTATAATGTATGCTATACGAAGTTATAC<br>CGGTCTCGTAGTGTTCACGTTCAGTTCACGGTGAGCTTAAAACTATCTTCAAG<br>AAGAGATTTGAGACCTGATTTATACTTGCAGCAATGTTTACTTCTTATCGCGA<br>TACACGAATGTGATACGGATCAAAGTAAGCAGGACTACGATAAGATAACGAAT<br>GCGGTGCAGTCCATGTCGATTAGGTATAGATACATTTATTTTGTGTTATGTTA<br>CATTTTGGGGGGATACTGTCCTACTTGTAGTACCTACTTGTAGTGGCGCGTTA<br>GGGGCAGGGCATGCTCATGTAGAGCGCCTGCCGCTCGCCGTCCGAGGCGGTGC<br>CGTCGTACAGGGCGGTGTCCAGGCCGCAGAGGGTGAACCCCATCCGCCGGTA | |
| MB9523 | GCGGAGCCTAGGCCGGCCAGCGTGGCGCGTGGCCATATTGGCCAGCAGCTTAC<br>TACAGCTCAGCCAAAGTGGATCATGATGGACGGAAATATCGGACTGGAGGCCA<br>AAAAGGAGGTGCTCAAATACGCACGGGACAAGTCTGCACAGGTGGCATTCGAA | 8 |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CCCACGTCTGTCCCCAAAGCCGCTGCTCTTTCCGAGCTCAATCTGCCCGTTTA<br>CCCCAACAACTCCATTGCCTTAGCCACCCCCAACACTGCAGAGCTCGAGGCCA<br>TGTTCGAGGCATTCCACGAGAAGGGCCGATTTGACGTTGACGACTGGTTTCCA<br>GTCATAGACGGTCTTGCTCTCGGAGCTGACTTTAGAAACGGAGCCACCATGTT<br>GTCGCACCAACATCGTGGACTCAAAGCTATTCTCGAACAAGGAACTCTGGCCC<br>AGGCAATCCACATGCTACCATACATCCCAACTTTGATCATCAAGGGCGGAGCC<br>AACGGCGTCGTCGTCTTCCAACTCATTGATGATATCGAGTCTGCCATTCATTC<br>ACAGCGTTCTGCTTCCAATAAAACGCCTGGCCTGTTCCAGAAGGGCAACGCTG<br>CGAGTGGAAACACCAAGGTCGGCGTCTACATGCAGTACTTTGAGCCCGAAGAA<br>GTGGGCAGTCAGTCGATTGTAAGCGTGACTGGAGCTGGAGACACTCTGTTTGG<br>AACCCTGGCCATGGAGATTGTCAAGGACGAGTCCTGGTTGAACGATATGGGAG<br>ACAAGAAGAGTGCAGTTGTTTCTCGAGCCATGAACAATGCTGTGAAGACTATT<br>CAGAGTAAGGACGCTGTCTGCAAGAGCATCCTTTAAGTGATTTGCCATGCTTT<br>CTCTTCTTCCACGATGTAAATACTTATTTTACACACTACTGTGCAGTAGCAAA<br>TACAGAACAAGAGTTGTCGCCTATTGACAGTACAGTACGAGTAGTGTATGTAC<br>AGTAGTTATACAATATCTATGTGAAATTCGTCGGCAGCTTTCGGCTGATGAAC<br>TACGAGTTCTTCGTAATAAATCATCAACGTAATAAGCTTGGTACCAGAGACGG<br>GTTGGCGGCGTATTTGTGTCCCAAAAAACAGCCCCAATTGCCCCAATTGACCC<br>CAAATTGACCCAGTAGCGGGCCCAACCCCGGCGAGAGCCCCCTTCACCCCACA<br>TATCAAACCTCCCCCGGTTCCCACACTTGCCGTTAAGGGCGTAGGGTACTGCA<br>GTCTGGAATCTACGCTTGTTCAGACTTTGTACTAGTTTCTTTGTCTGGCCATC<br>CGGGTAACCCATGCCGGACGCAAAATAGACTACTGAAAATTTTTTTGCTTTGT<br>GGTTGGGACTTTAGCCAAGGGTATAAAAGACCACCGTCCCCGAATTACCTTTC<br>CTCTTCTTTTCTCTCTCTCCTTGTCAACTCACACCCGAAATCGTTAAGCATTT<br>CCTTCTGAGTATAAGAATCATTCGCTAGCCACAAAAATGGGTGATCTCGATGC<br>CCGAGGAACCTCTGCTCACCCCGAGCTCTCTGAGCGACCTTCTATTATGCCTT<br>CTATGTCTGATATTCAGGACCCTTCTGGTGATGACAAGGCTACTCCCCGAGGA<br>TCTGCTGCTGGTCTGCCCCAGCTTGAGCTTGCTGGACACGCCCGACGACTTGG<br>CCACCTTGAGAACTTCTTTGCTGTCCAGGCTCGACAGCAGATTTACTCTTCTT<br>TTGCTGTTTTTTGTGAGTTTGACACTGCTTGTTCTCTCGCTCAGCTTGCTTCT<br>GCTGTGCGAAACGTTTGTCTTTCTAACCCCCTTCTCCTTCACACTGTTGAGCC<br>TAAGCACCCTGACATCGCTGGATTCTACCACTCTGACGAGTACCTTTCCCGAC<br>CTTGGCCTCAGCACGATTACATGCGAGTTCTTCGAGAGGTTCACGTCGCTGAC<br>GTTGTTATGAACGGACAGAAGGAGCACGCTCACGTTGTTCGAGATGCTGTTGA<br>CGTTTTTCAGGCTCACGGAAACCAGGTTACTTCTGAGCTCCTTGAGCTTATGA<br>CTCAGATTGAGATTCCTCACGCTTCTCAGACTCGACCCTCTTGGCGACTTCTC<br>TGTTTTCCCCACGGAGAGGCTAACCGATGGCGAACCTTTGCTTTTGTTTCTAA<br>CCACTGTTCTTCTGATGGTCTTTCTGGTCTTAACTTCTTTCGAGATCTCCAGA<br>AGGAGCTTGCTCACGGCCCCACCTCTGGTGCTCCTGGTGCCCCCGGAGCTTCC<br>GGAGTTATTTTCGATTACGCTCAGGACGCTGCTACCCTGCCCAAGCTGCCCCC<br>TCCCATTGATCAGAAGCTCGATTACCGACCTTCTAAGAAGGCTCTTCTCGGCC<br>TTCTCGCTGGCAAGTTCGTTCGAGAGAAGCTCGGTTACGTTTCTGCTGCTCCT<br>CCCACTACCCCTACCTCTGACCTTGCTCACCCTGAGGGTCACCAGTACTACTG<br>TTACCTTGTTAACGTTCCCACTTCTTCTGTTGCCCACATTAAGACTCAGGTGC<br>GAGAGAACGTTCCTCACAAGTGTACTCTCACTCCCTTTCTCCAGGCTTGTTGG<br>CTTGTTTCTCTGTTCAAGTACGGTCGAGTTTTTTCTGGTTCTTGGCTTGAGCG<br>ATACACCGATGTTCTTGTTGCTATGAACACTCGACAGCTTCTCCCCGAGGACC<br>TTGAGCTTCAGCGACAGTACCGATACGGTTCTAACATTGGAGCTGTTCGATAC<br>AACTACCCTATTGCTCCCCTTGACGTTCGAGATAACGATCAGAAGTTCTGGTC<br>CCTTGTTGAGTCTTACCGACTTGCCCTTTCTGATGCCCGAGATAAGAACGATT<br>ACCTTTACGCTCTTGGTGCTCTTATGCTCCCTGAGATTTACGAGAAGAAGAAC<br>GTTGATGCTGTTGTTAACGATACCATTCTTAACCAGCGACGACAGGGAACCCT<br>TCTTTCTAACGTTGGTTACGTTCGAGATGAGCAGCCCACTGCTTTTGCTATTA<br>AGAACCACGTTTTTTCTCAGGGAGTTGGAGCTAACCGAAACGCTTTTGTTCTT<br>AACATTTGTGCTACCGATCAGGGTGGTCTTAACATCGCTATTTCTATTGCTAA<br>GGGAACCCTTGCTTCTCGACAGGAGGGACAGGAGCTTTGTGATATTTTTAAGT<br>CTACTCTCCTTCGATTTTAAACGCGTCTATCCGAAGATCAAGAGCGAAGCAAG<br>TTGTAAGTCCAGGACATGTTTCCCGCCCACGCGAGTGATTTATAACACCTCTC<br>TTTTTTGACACCCGCTCGCCTTGAAATTCATGTCACATAAATTATAGTCAACG<br>ACGTTTGAATAACTTGTCTTGTAGTTCGATGATGATCATATGATTACATTAAT<br>AGTAATTACTGTATCTGTACCTGCTGTGGACCACGCACGGCGGAACGTACCGT<br>ACAAATATTTTCTTGCTCACATGACTCTCTCTCGGCCGCGCACGCCGGTGGCA<br>AATTGCTCTTGCATTGGCTCTGTCTCTAGACGTCCAAACCGTCCAAAGTGGCA<br>GGGTGACGTGATGCGACGCACGAAGGAGATGGCCCGGTGGCGAGGAACCGGAC<br>ACGGCGAGCCGGCGGGAAAAAAGGCGGAAAACGAAAAGCGAAGGGCACAATCT<br>GACGGTGCGGCTGCCACCAACCCAAGGAGGCTATTTTGGGTCGCTTTCCATTT<br>CACATTCGCCCTCAATGGCCACTTTGCGGTGGTGAACATGGTTTCTGAAACAA<br>CCCCCCAGAATTAGAGTATATTGATGTGTTTAAGATTGGGTTGCTATTTGGCC<br>ATTGTGGGGGAGGGTAGCGACGTGGAGGACATTCCAGGGCGAATTGAGCCTAG<br>AAAGTGGTACCATTCCAACCGTCTCAGTCGTCCGAATTGATCGCTATAACTAT<br>CACCTCTCTCACATGTCTACTTCCCCAACCAACATCCCCAACCTCCCCCACAC | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | TAAAGTTCACGCCAATAATGTAGGCACTCTTTCTGGGTGTGGGACAGCAGAGC<br>AATACGGAGGGGAGATTACACAACGAGCCACAATTGGGGAGATGGTAGCCATC<br>TCACTCGACCCGTCGACTTTTGGCAACGCTCAATTACCCACCAAATTTGGGCT<br>GGAGTTGAGGGGACCGTGTTCCAGCGCTGTAGGACCAGCAACACACACGGTAT<br>CAACAGCAACCAACGCCCCCGCTAATGCACCCAGTACTGCGCAGGTGTGGGCC<br>AGGTGCGTTCCAGATGCGAGTTGGCGAACCCTAAGCCGACAGTGTACTTTTTG<br>GGACGGGCAGTAGCAATCGTGGGCGTAGACCCCGGTGTATATAAAGGGGTGGA<br>GAGGACGGATTATTAGCACCAACACACACACTTATACTACATGCTAGCCACAA<br>AAATGCTCTCTTTCTTCTGGCGAAACGGTATCGAGACTCCCGAGCCCCTCAAG<br>GCTGACGTTTCCGGCTCTATCCCTCCCTGGCTTCAGGGAACCCTTCTCCGAAA<br>CGGTCCTGGTCTGTTCTCCGTTGGCAACACTTCCTACAAGCACTGGTTCGATG<br>GTATGGCTCTCATTCACTCCTTCACCTTTAAGGATGGTGAGGTTTTTTACCGA<br>TCTAAGTACCTGAAGTCTGAGACTTACAAGAAGAACATCGCTGCCGACCGAAT<br>CGTTGTGTCTGAGTTCGGAACCATGGTGTACCCCGATCCCTGCAAGAACATTT<br>TCTCCCGAGCCTTCTCTTACATGATGAACGCCATTCCTGACTTTACCGATAAC<br>AACCTCATTAACATCATTAAGTACGGTGAGGATTACTACGCCTCCTCTGAGGT<br>CAACTACATCAACCAGATTGACCCCCTGACCCTTGAGACTCTCGGACGAACTA<br>ACTACCGAAACCACATTGCCATCAACCTTGCCACTGCTCACCCTCACTACGAC<br>GAGGAGGGTAACACTTACAACATGGGCACTGCTATTATGAACCTCGGTCGACC<br>CAAGTACGTGATTTTCAAGGTGCCCGCCAACACCTCTGATAAGGAGAACAAGA<br>AGCCTGCCCTCTCTGAGGTGGAGCAGGTTTGCTCCATTCCCATCCGACCCTCC<br>CTTTACCCTTCTTACTTCCACTCTTTTGGCATGACTGAGAACTACATCATCTT<br>CGTTGAGCAGGCCTTCAAGCTGGACATCGTCAAGCTGGCTACTGCTTACTTCC<br>GAGATATTAACTGGGGATCTTGCCTTAAGTTCGACCAGGATGACATTAACGTG<br>TTCCACCTGGTCAACAAGAAGACTGGTAAGGCTGTGTCCGTGAAGTACTACAC<br>TGACCCCTTTGTTACCTTCCACCACATCAACGCTTACGAGGACGATGGCCACG<br>TCGTCTTCGATCTCATTACTTACAAGGACTCTAAGCTGTACGATATGTTCTAC<br>ATTCAGAACATGAAGCAGGACGTCAAGCGATTTATTGAGACTAACAAGGACTT<br>CGCTCAGCCCGTGTGCCAGCGATTTGTCCTTCCCGTCAACGTTGATAAGGAGA<br>CTCCTCAGGACATCAACCTTGTCAAGCTGCAGGACACCACTGCCACTGCTGTC<br>CTGAAGGAGGACGGCTCTGTCTACTGCACCCCTGACATCATTTTTAAGGGTCT<br>TGAGCTCCCTGCTATCAACTACAAGTTTAACTCTAAGAAGAACCGATACTTCT<br>ACGGCACCCGAGTGGAGTGGTCCCCTTACCCTAACAAGGTCGCTAAGGTGGAC<br>GTTGTTACTCGAACCCACAAGATTTGGACTGAGGAGGAGTGTTACCCTTCTGA<br>GCCTGTCTTTATTGCCTCCCCTGACGCCGTTGATGAGGATGACGGTGTGATTC<br>TTTCTTCTGTGGTTTCTTTCAACCCCCAGCGACCCCCTTTCCTGGTTGTCCTC<br>GATGCTAAGTCCTTCAAGGAGATTGCTCGAGCTACCATCGATGCCTCTATTCA<br>CATGGACCTTCACGGCCTTTTCATCCACGACAAGTCTACCTAAGTTTTTTGAT<br>CAATGATCCAATGGCTTTCACATACCCCCCCACGCCTATAATTAAAACACAGA<br>GAAATATAATCTAACTTAATAAATATTACGGAGAATCTTTCGAGTGTTCAGCA<br>GAAATATAGCCATTGTAACAAAAGCCGGCTATCGACCGCTTTATCGAAGAATA<br>TTTCCCGCCCCCCAGTGGCCAAACGATATCGGTCAGAAGGGGCAGCTCTAAAC<br>GAAGAACTGCGGTCAGGTGACACAACTTTTTCCATCTCAGGGTGTGTCGCGTG<br>TGCTTCATCCAAACTTTAGTTGGGGTTCGGGTTCGCGCGAGATGATCACGTGC<br>CCTGATTTGGTGTCGTCCCCCGTCGCGCTGCGCACGTGATTTATTTATTTCCG<br>GTGGCTGCTGTCTACGCGGGGCCTTCTCTGCCCTTCTGTTTCAACCTTCGGGC<br>GGTTCTCGTAACCAGCAGTAGCAATCCATTTCGAAACTCAAAGAGCTAAAAAC<br>GTTAAACCTCAGCAGTCGCTCGACGAATGGGCTGCGGTTGGGAAGCCCACGAG<br>GCCTATAGCCAGAGCCTCGAGTTGACAGGAGCCCAGACGCCTTTTCCAACGGC<br>AACTTTTATATAAAATGGCAATGTATTCATGCAATTGCGGCCGTGTCAGGTTG<br>GAGACACTGGACCACACTCTCCATTGCTTCCTGAGGAGATGGATCATTGCTAG<br>TGCATCTACGCGCAGCAATCCCGCAAGCTCGACAACCGTAGATGGGCTTTGGT<br>GGGCCAATCAATTACGCAACCCGCACGTTAAATTGTATGAGGAAGGAAGGCCA<br>CGGTACAAAGTGGGTGGTCTTCACCCAGTGGTTGTTGGTGGCGTCATGCAGAC<br>CATGCATTGGGGATAGCACAGGGTTGGGGTGTCTTGTGGACTCAATGGGTGAA<br>AGGAGATGGAAAAGGGCGGTGAAAAGTGGTAGAATCGAAATCCCTGACGTCAA<br>TTTATAAAGTAAAATGCGTTTCTGCCATTTTGCTCCCCTCCTTCTTTCGCAAT<br>CGCCTCCCCAAAAGTTGTCGTGGCAGTACACATGCTTGCATACAATGAAGCTA<br>ATCCGGCTTGCTCAGTAGTTGCTATATCCAGGCATGGTGTGAAACCCCTCAAA<br>GTATATATAGGAGCGGTGAGCCCCAGTCTGGGGTCTTTTCTCTCCATCTCAAA<br>ACTACTTTCTCACATGCTAGCCACAAAAATGACCACTAAGTACACTTCCGTTC<br>ACGAGTCTCCCAACGGCCCTGGTGACGCTCGACCCACCGCTTCCCAGATTATC<br>GACGATTACAACCTTGAGGGAGAGCTTTCTGGCAAGACTGTTCTCGTCACCGG<br>CTGTTCCTCTGGTATTGGTGTTGAGACTGCCCGAGCTATTTACCGAACTGGTG<br>CCACCCTTTACCTCACTGCCCGAGATGTCGATAAGGCCAAGACCGTTCTTCCC<br>GACCTTGTTGACACTTCCCGAGTCCACTTTCTCCACCTTGACCTTAACTCTCT<br>GGAGTCTGTTCGAGGTTTTGCTGAGAACTTCAAGTCTAAGTCCACTCAGCTTC<br>ACATTCTCATCGAGAACGCTGGCGTGATGGCCTGTCCCGAGGGCCGAACCGTC<br>GATGGTTTTGAGACTCAGTTTGGTATCAACCACCTTGCTCACTTTCTCCTCTT<br>TTACCTCCTCAAGGATACCCTTCTCAACTCTTCTACCCCCGCTTTCAACTCCC<br>GAGTTGTCATCCTCTCTTCTTGTGCTCACCAGGCTGGTTCCGTTCACCTTAAC | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | AACCTGTCTCTTGAGGGTGGATACGAGCCTTGGAAGTCTTACGGCCAGTCCAA<br>GACTGCCAACCTTTGGACTGCCCGAGAGATCGAGAAGCGATTTGGTGCTTCCG<br>GTATCCACTCTTGGGCTGTTCACCCCGGTTCCATCGCTACTGAGCTTCAGCGA<br>CACGTTTCCGACGAGCTTAAGCAGAAGTGGGCTGACGATAAGGAGGGTGCCAA<br>GCTGTGGAAGTCCACCGAGCAGGGTGCCGCCACCACTGTCCTTGCTGCTGTTT<br>CCCCTGAGCTTGAGGGTAAGGGCGGTCTTTACCTTGAGGATACCCAGGTTGCC<br>AAGCCCCCTGCCCGAGGAATGTTTGGTGTTGCTGACTGGGCTTACGATGAGGA<br>TGGCCCCTCTAAGCTCTGGGCCAAGTCTCTTGAGCTCCTTAAGCTCCAGTAAA<br>GGTTAGACTATGGATATGTAATTTAACTGTGTATATAGAGAGCGTGCAAGTAT<br>GGAGCGCTTGTTCAGCTTGTATGATGGTCAGACGACCTGTCTGATCGAGTATG<br>TATGATACTGCACAACCTGTGTATCCGCATGATCTGTCCAATGGGGCATGTTG<br>TTGTGTTTCTCGATACGGAGATGCTGGGTACAAGTAGCTAATACGATTGAACT<br>ACTTATACTTATATGAGGCTTGAAGAAAGCTGACTTGTGTATGACTTATTCTC<br>AACTACATCCCCAGTCACAATACCACCACTGCACTACCACTACACACTAGTGG<br>TGTGTTCTGTGGAGCATTCTCACTTTTGGTAAACGACATTGCTTCAAGTGCAG<br>CGGAATCAAAAAGTATAAAGTGGGCAGCGAGTATACCTGTACAGACTGTAGGC<br>GATAACTCAATCCAATTACCCCCCACAACATGACTGGCCAAACTGATCTCAAG<br>ACTTTATTGAAATCAGCAACACCGATTCTCAATGAAGGCACATACTTCTTCTG<br>CAACATTCACTTGACGCCTAAAGTTGGTGAGAAATGGACCGACAAGACATATT<br>CTGCTATCCACGGACTGTTGCCTGTGTCGGTGGCTACAATACGTGAGTCAGAA<br>GGGCTGACGGTGGTGGTTCCCAAGGAAAAGGTCGACGAGTATCTGTCTGACTC<br>GTCATTGCCGCCTTTGGAGTACGACTCCAACTATGAGTGTGCTTGGATCACTT<br>TGACGATACATTCTTCGTTGGAGGCTGTGGGTCTGACAGCTGCGTTTTCGGCG<br>CGGTTGGCCGACAACAATATCAGCTGCAACGTCATTGCTGGCTTTCATCATGA<br>TCACATTTTTGTCGGCAAAGGCGACGCCCAGAGAGCCATTGACGTTCTTTCTA<br>ATTTGGACCGATAGCCGTATAGTCCAGTCTATCTATAAGTTCAACTAACTCGT<br>AACTATTACCATAACATATACTTCACTGCCCCAGATAAGGTTCCGATAAAAAG<br>TTCTGCAGACTAAATTTATTTCAGTCTCCTCTTCACCACCAAAATGCCCTCCT<br>ACGAAGCTCGAGCTAACGTCCACAAGTCCGCCTTTGCCGCTCGAGTGCTCAAG<br>CTCGTGGCAGCCAAGAAAACCAACCTGTGTGCTTCTCTGGATGTTACCACCAC<br>CAAGGAGCTCATTGAGCTTGCCGATAAGGTCGGACCTTATGTGTGCATGATCA<br>AGACCCATATCGACATCATTGACGACTTCACCTACGCCGGCACTGTGCTCCCC<br>CTCAAGGAACTTGCTCTTAAGCACGGTTTCTTCCTGTTCGAGGACAGAAAGTT<br>CGCAGATATTGGCAACACTGTCAAGCACCAGTACAAGAACGGTGTCTACCGAA<br>TCGCCGAGTGGTCCGATATCACCAACGCCCACGGTGTACCCGGAACCGGAATC<br>ATTGCTGGCCTGCGAGCTGGTGCCGAGGAAACTGTCTCTGAACAGAAGAAGGA<br>GGACGTCTCTGACTACGAGAACTCCCAGTACAAGGAGTTCCTGGTCCCCTCTC<br>CCAACGAGAAGCTGGCCAGAGGTCTGCTCATGCTGGCCGAGCTGTCTTGCAAG<br>GGCTCTCTGGCCACTGGCGAGTACTCCAAGCAGACCATTGAGCTTGCCCGATC<br>CGACCCCGAGTTTGTGGTTGGCTTCATTGCCCAGAACCGACCTAAGGGCGACT<br>CTGAGGACTGGCTTATTCTGACCCCCGGGGTGGGTCTTGACGACAAGGGAGAC<br>GCTCTCGGACAGCAGTACCGAACTGTTGAGGATGTCATGTCTACCGGAACGGA<br>TATCATAATTGTCGGCCGAGGTCTGTACGGCCAGAACCGAGATCCTATTGAGG<br>AGGCCAAGCGATACCAGAAGGCTGGCTGGGAGGCTTACCAGAAGATTAACTGT<br>TAGAGGTTAGACTATGGATATGTAATTTAACTGTGTATATAGAGAGCGTGCAA<br>GTATGGAGCGCTTGTTCAGCTTGTATGATGGTCAGACGACCTGTCTGATCGAG<br>TATGTATGATACTGCACAACCTGTGTATCCGCATGATCTGTCCAATGGGGCAT<br>GTTGTTGTGTTTCTCGATACGGAGATGCTGGGTACAAGTAGCTAATACGATTG<br>AACTACTTATACTTATATGAGGCTTGAAGAAAGCTGACTTGTGTATGACTTAT<br>TCTCAACTACATCCCCAGTCACAATACCACCACTGCACTACCACTACACCTCG<br>AGCATGCACACTATTATCACATTACTACATCCAAACCCCTACAGGGGGAGGAG<br>CTCTCCAATCAAATATGTACATTAACTATCTCTCGTAAATCATTGTTATAAGA<br>CCGTCCGTGACTGTCTAAATCGGTTCATTCGTTGTAACAAATCAGTGTAACAA<br>CTCGTGGTACGCCCGGTTTGCTTCGCTCACGCTCCCCTAGATTTTCCGTCTAG<br>GACACAACAAGCCCTGGTGGATGACGTTCAACGCCTTCAGCGCGTCTTTTTCC<br>TCAATAACACACGAGATGTTAATTTCGTTGGCTCCCTGAGAAATCATCTCAAT<br>GTTAATACCTGCCTGGGCCAGAGTAGAGAAGAACATGCCTGCACATCCGACCA<br>TGGCCTTCATTCTCGTTCCGATCAGCGACACAATGGTCATGCCTCGCTTCACA<br>TCTACTGTGCCGTACTTTCGCAGCTCCTCCACAGCCTGCTTGAGGTTGGAGTC<br>GGGAGCATGGAAGGCCATCGACACATGGACCTCAGAAGTGGAGATGAGATCGA<br>CGACAAGTTTCTGCTGGTCGAGAGTAGCAAAGATCTTGTTCAAGAAGCCATGA<br>CTCTTGGTTCGCTTATTCGAATGAACGTTGAGAACGGTGATATTCGATTTGGT<br>AGTGACAGCTGTAGGCTTCTTCTCGTCATCTACAGGAGCAGACACCTGGGGAG<br>TGAATGAGCCAGAGGACAGAGAAGTTAGCGAGTCGGTGGAAGAAGCCAGATCC<br>TGGACATTGTTTTTCGTTTTCAGGTTGCCCGAGCCGTCAGCAGATGGGTAGAT<br>GATAGTTCCTCCTCCCAGGGGGTTTTCCACGTTTTTGATTCGGATAGGAATAT<br>GGGCCTTAATGACCTGCTCCATGGTGAAGGGGTGGATGACTTCAGATCCGTAG<br>TAGGTCAACTCAGCGGCCTCCTCGGGGGTAATGATGGGCAGCAGACGGGCAGT<br>GGACACCTTTCTGGGATCGGCAGTGAAGACACCATCGACTTCTTTCCAGATCT<br>GAAGCTCCTTGGCGTCCAGACCCACAGCCACCAGAGCAGCACACAGATCGGTG<br>TATCCTCGTCCGATCTGGCTTAGGAGGCCTCCCTTGACGGGGCCAAAGAAACC | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | GGTCAACACGGGCACCATGTTTCCCTTGACAGGAGCAGAGTCCGTGTTAGGAG<br>AGCCGGGAAGAGTGATGATCTCGCCCAGAACACGTCCGAGGTCCGAATAGAAC<br>TTGGGATCTTCGGCATTGGTGGTGGTAACTGCGTGAGACAGGTCAAAGTACCG<br>TGCGTTAACACCAGCGTCCCGCATAACTGCAGTCATGTACATGCAACTGAGCT<br>TCTCCCCAATGGCCATGATGGAGTCGAGTGTTCGGGGGGAGATCTCAGAAATG<br>ATTTCAGCAGCAGCCAGGATTCGCAACAGCTGGTCGCACTCGCCGTTGATGTC<br>GGCATTGAGGTTTTCGAGCAGTTCGGGGTTCTTGACGTCACGCTTAGCAGCTG<br>CAAGATGGTCTTCTCGGATAGACTCAATGATGGGGTTGTAGGCGTCTGATCCG<br>AGAAGAGCAGAGTCAGCAGCAGCAATAAGACGGGTGGTGGTTCCCTCGGCCTT<br>GGTGGCCTCTAGATGGCCTCCTTGGCCCCATTCCAGCTGCATTAATGAATCGG<br>CCAACGCGCGGGGAGAGGCGGTTTGCGTATTGGGCGCTCTTCCGCTTCCTCGC<br>TCACTGACTCGCTGCGCTCGGTCGTTCGGCTGCGGCGAGCGGTATCAGCTCAC<br>TCAAAGGCGGTAATACGGTTATCCACAGAATCAGGGGATAACGCAGGAAAGAA<br>CATGTGAGCAAAAGGCCAGCAAAAGGCCAGGAACCGTAAAAAGGCCGCGTTGC<br>TGGCGTTTTTCCATAGGCTCCGCCCCCCTGACGAGCATCACAAAAATCGACGC<br>TCAAGTCAGAGGTGGCGAAACCCGACAGGACTATAAAGATACCAGGCGTTTCC<br>CCCTGGAAGCTCCCTCGTGCGCTCTCCTGTTCCGACCCTGCCGCTTACCGGAT<br>ACCTGTCCGCCTTTCTCCCTTCGGGAAGCGTGGCGCTTTCTCATAGCTCACGC<br>TGTAGGTATCTCAGTTCGGTGTAGGTCGTTCGCTCCAAGCTGGGCTGTGTGCA<br>CGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAAC<br>AGGATTAGCAGAGCGAGGTATGTAGGCGGTGCTACAGAGTTCTTGAAGTGGTG<br>GCCTAACTACGGCTACACTAGAAGAACAGTATTTGGTATCTGCGCTCTGCTGA<br>AGCCAGTTACCTTCGGAAAAAGAGTTGGTAGCTCTTGATCCGGCAAACAAACC<br>ACCGCTGGTAGCGGTGGTTTTTTTGTTTGCAAGCAGCAGATTACGCGCAGAAA<br>AAAAGGATCTCAAGAAGATCCTTTGATCTTTTCTACGGGGTCTGACGCTCAGT<br>GGAACGAAAACTCACGTTAAGGGATTTTGGTCATGAGATTATCAAAAAGGATC<br>TTCACCTAGATCCTTTTAAATTAAAAATGAAGTTTTAAATCAATCTAAAGTAT<br>ATATGAGTAAACTTGGTCTGACAGTTACCAATGCTTAATCAGTGAGGCACCTA<br>TCTCAGCGATCTGTCTATTTCGTTCATCCATAGTTGCCTGACTCCCCGTCGTG<br>TAGATAACTACGATACGGGAGGGCTTACCATCTGGCCCCAGTGCTGCAATGAT<br>ACCGCGAGAGCCACGCTCACCGGCTCCAGATTTATCAGCAATAAACCAGCCAG<br>CCGGAAGGGCCGAGCGCAGAAGTGGTCCTGCAACTTTATCCGCCTCCATCCAG<br>TCTATTAATTGTTGCCGGGAAGCTAGAGTAAGTAGTTCGCCAGTTAATAGTTT<br>GCGCAACGTTGTTGCCATTGCTACAGGCATCGTGGTGTCACGCTCGTCGTTTG<br>GTATGGCTTCATTCAGCTCCGGTTCCCAACGATCAAGGCGAGTTACATGATCC<br>CCCATGTTGTGCAAAAAAGCGGTTAGCTCCTTCGGTCCTCCGATCGTTGTCAG<br>AAGTAAGTTGGCCGCAGTGTTATCACTCATGGTTATGGCAGCACTGCATAATT<br>CTCTTACTGTCATGCCATCCGTAAGATGCTTTTCTGTGACTGGTGAGTACTCA<br>ACCAAGTCATTCTGAGAATAGTGTATGCGGCGACCGAGTTGCTCTTGCCCGGC<br>GTCAATACGGGATAATACCGCGCCACATAGCAGAACTTTAAAAGTGCTCATCA<br>TTGGAAAACGTTCTTCGGGGCGAAAACTCTCAAGGATCTTACCGCTGTTGAGA<br>TCCAGTTCGATGTAACCCACTCGTGCACCCAACTGATCTTCAGCATCTTTTAC<br>TTTCACCAGCGTTTCTGGGTGAGCAAAAACAGGAAGGCAAAATGCCGCAAAAA<br>AGGGAATAAGGGCGACACGGAAATGTTGAATACTCATACTCTTCCTTTTTCAA<br>TATTATTGAAGCATTTATCAGGGTTATTGTCTCATGAGCGGATACATATTTGA<br>ATGTATTTAGAAAAATAAACAAATAGGGGTTCCGCGCACATTTCCCCGAAAAG<br>TGCCACCTGACGTCTAAGAAACCATTATTATCATGACATTAACCTATAAAAAT<br>AGGCGTATCACGAG | |
| MB8388-<br>LIP8 | GGTTCCGCTTCCTCGCTCACTGACTCGCTGCGCTCGGTCGTTCGGCTGCGGCG<br>AGCGGTATCAGCTCACTCAAAGGCGGTAATACGGTTATCCACAGAATCAGGGG<br>ATAACGCAGGAAAGAACATGTGAGCAAAAGGCCAGCAAAAGGCCAGGAACCGT<br>AAAAAGGCCGCGTTGCTGGCGTTTTTCCATAGGCTCCGCCCCCCTGACGAGCA<br>TCACAAAAATCGACGCTCAAGTCAGAGGTGGCGAAACCCGACAGGACTATAAA<br>GATACCAGGCGTTTCCCCCTGGAAGCTCCCTCGTGCGCTCTCCTGTTCCGACC<br>CTGCCGCTTACCGGATACCTGTCCGCCTTTCTCCCTTCGGGAAGCGTGGCGCT<br>TTCTCATAGCTCACGCTGTAGGTATCTCAGTTCGGTGTAGGTCGTTCGCTCCA<br>AGCTGGGCTGTGTGCACGAACCCCCCGTTCAGCCCGACCGCTGCGCCTTATCC<br>GGTAACTATCGTCTTGAGTCCAACCCGGTAAGACACGACTTATCGCCACTGGC<br>AGCAGCCACTGGTAACAGGATTAGCAGAGCGAGGTATGTAGGCGGTGCTACAG<br>AGTTCTTGAAGTGGTGGCCTAACTACGGCTACACTAGAAGGACAGTATTTGGT<br>ATCTGCGCTCTGCTGAAGCCAGTTACCTTCGGAAAAAGAGTTGGTAGCTCTTG<br>ATCCGGCAAACAAACCACCGCTGGTAGCGGTGGTTTTTTTGTTTGCAAGCAGC<br>AGATTACGCGCAGAAAAAAAGGATCTCAAGAAGATCCTTTGATCTTTTCTACG<br>GGGTCTGACGCTCAGTGGAACGAAAACTCACGTTAAGGGATTTTGGTCATGAG<br>ATTATCAAAAAGGATCTTCACCTAGATCCTTTTAAATTAAAAATGAAGTTTTA<br>AATCAATCTAAAGTATATATGAGTAAACTTGGTCTGACAGTTACCAATGCTTA<br>ATCAGTGAGGCACCTATCTCAGCGATCTGTCTATTTCGTTCATCCATAGTTGC<br>CTGACTCCCCGTCGTGTAGATAACTACGATACGGGAGGGCTTACCATCTGGCC<br>CCAGTGCTGCAATGATACCGCGAGACCCACGCTCACCGGCTCCAGATTTATCA | 9 |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | GCAATAAACCAGCCAGCCGGAAGGGCCGAGCGCAGAAGTGGTCCTGCAACTTT<br>ATCCGCCTCCATCCAGTCTATTAATTGTTGCCGGGAAGCTAGAGTAAGTAGTT<br>CGCCAGTTAATAGTTTGCGCAACGTTGTTGCCATTGCTGCAGGCATCGTGGTG<br>TCACGCTCGTCGTTTGGTATGGCTTCATTCAGCTCCGGTTCCCAACGATCAAG<br>GCGAGTTACATGATCCCCCATGTTGTGCAAAAAAGCGGTTAGCTCCTTCGGTC<br>CTCCGATCGTTGTCAGAAGTAAGTTGGCCGCAGTGTTATCACTCATGGTTATG<br>GCAGCACTGCATAATTCTCTTACTGTCATGCCATCCGTAAGATGCTTTTCTGT<br>GACTGGTGAGTACTCAACCAAGTCATTCTGAGAATAGTGTATGCGGCGACCGA<br>GTTGCTCTTGCCCGGCGTCAACACGGGATAATACCGCGCCACATAGCAGAACT<br>TTAAAAGTGCTCATCATTGGAAAACGTTCTTCGGGGCGAAAACTCTCAAGGAT<br>CTTACCGCTGTTGAGATCCAGTTCGATGTAACCCACTCGTGCACCCAACTGAT<br>CTTCAGCATCTTTTACTTTCACCAGCGTTTCTGGGTGAGCAAAAACAGGAAGG<br>CAAAATGCCGCAAAAAAGGGAATAAGGGCGACACGGAAATGTTGAATACTCAT<br>ACTCTTCCTTTTTCAATATTATTGAAGCATTTATCAGGGTTATTGTCTCATGA<br>GCGGATACATATTTGAATGTATTTAGAAAAATAAACAAATAGGGGTTCCGCGC<br>ACATTTCCCCGAAAAGTGCCACCTGACGTCTAAGAAACCATTATTATCATGAC<br>ATTAACCTATAAAAATAGGCGTATCACGAGGCCCTTTCGTCTGGCCTAGGAAG<br>CGACTTCCAATCGCTTTGCATATCCAGTACCACACCCACAGGCGTTTGTGCTA<br>CTCTACTGATAGCAATAGATGCGTCATAATTGGTTGGCCCGCTGAGCCTCCAC<br>AGGATACTATTGCACATACCCTGGTCATGTGCAGATCAGCTCATTTGTGGAGA<br>CTCTGGAGTAACTTAGACGACGCCTGGTTCAATTGCCGCAATGTGCGCCCACG<br>CAGATAATGTATTGAGGGGTGGAGCGCCTCTTGGGGACTTGCTGTACTTGTAC<br>GGGATATTAAACGCACTCAGCAAGACCATGACGTAAAACACACCTACTGTACG<br>ATACGTACTGTAGGTATTGTACTCGTACCCGGTACTACAAATAGTACGATACT<br>ATACGGAGTGTATTTGTACCTTGATATACGACTGGCGGAGTGAAGAGAAGGAG<br>TTGAACAAGACCAGATGGGGATATCAGCCCCAGTGCTTTGTATTACAAGTACG<br>AGTACTTAATAGATACTGTAAGGCTATTGATACGGATGGCAGTAAGTCATTGA<br>GTAAGCAATTGTGGCCCAGCATCTCCCCTACGTACTTGTACCATACCCCATGG<br>AGACACCAATGGTCTTTCACGCACACTGTCGTGTGCTGTATCGCAGAATCGGG<br>TGTCCAACCAAATGCCGTTACCCCCACGTCACAGCCGATAGACAGATACACCA<br>TCAATACCAGCAGGTTGTATCATGCGGTTGGCTGAAGGTAAGCTGATTGGTCT<br>AAAAACTGTAGCTGTCCTAATTCAACGAGCGCTATTTGGGGCCAACCACCTCG<br>GCCAAGCGGCCTTTAATCTGCGTGCCCCAGAGGCGTCTAATGAGGCTCTGGCC<br>GCCACTGTAGGAGTGTTTCTCTGTGCGCACACGCAGTTTTGAGTTTGGGCGAC<br>TTTCCCTTTTTCCCAATTGCGTACACACACAGCTCCGAGCTAAGCGCTGTCCT<br>TGAACCTTCTCCCTCTTTTCCCTCTTTTTCTCTTCCCCTTCCCCTCCTCCACA<br>TTAAGGCCAAATCCTGAATTGCACCAACTAGTACAACGACAACAATGGACAAG<br>AAGTACTCCATCGGTTTGGACATTGGTACTAACTCTGTCGGCTGGGCCGTCAT<br>CACCGACGAGTACAAGGTTCCCTCCAAGAAGTTCAAGGTCCTTGGCAACACCG<br>ACCGACACTCTATCAAGAAGAACCTGATCGGTGCTCTGCTGTTCGACTCTGGC<br>GAGACTGCCGAGGCCACCCGACTGAAGCGAACCGCTCGACGCCGATACACCCG<br>ACGAAAGAACCGAATCTGTTACCTCCAGGAGATCTTCAGCAACGAGATGGCTA<br>AGGTCGACGACTCCTTCTTCCACCGACTCGAGGAGTCTTTCCTGGTCGAAGAG<br>GATAAGAAGCACGAGCGACACCCCATCTTCGGCAACATTGTTGATGAGGTTGC<br>CTACCATGAGAAGTACCCCACCATCTACCACCTCCGAAAGAAGCTCGTCGACT<br>CCACTGACAAGGCTGACCTCCGACTCATCTACCTTGCTCTCGCCCACATGATC<br>AAGTTCCGAGGTCACTTCCTCATTGAGGGTGATCTCAACCCCGACAACTCCGA<br>CGTTGACAAGCTGTTCATCCAGCTCGTCCAGACCTACAACCAGCTCTTTGAGG<br>AGAACCCTATCAACGCTTCTGGTGTTGACGCCAAGGCCATTCTCTCCGCCCGA<br>CTCTCTAAGTCCCGACGACTCGAGAACCTCATTGCCCAGCTGCCCGGCGAGAA<br>GAAGAACGGCCTCTTCGGTAACCTGATTGCTCTCTCTCTTGGTCTGACCCCCA<br>ACTTCAAGTCCAACTTTGACCTCGCCGAGGACGCCAAGCTCCAGCTGTCCAAG<br>GACACCTACGATGACGATCTGGACAACCTCCTGGCCCAGATCGGTGACCAGTA<br>CGCCGATCTCTTCCTTGCCGCCAAGAACCTCTCCGACGCCATCCTGCTCTCCG<br>ACATCCTCCGAGTCAACACCGAGATTACCAAGGCTCCTCTGTCTGCCTCTATG<br>ATCAAGCGATACGACGAGCACCACCAGGATCTCACTCTTCTCAAGGCTCTCGT<br>CCGACAGCAGCTCCCCGAGAAGTACAAGGAGATTTTCTTTGACCAGTCCAAGA<br>ACGGTTACGCTGGCTACATTGACGGTGGTGCTTCCCAGGAAGAGTTTTACAAG<br>TTCATCAAGCCTATTCTGGAGAAGATGGACGGTACCGAGGAGCTGCTCGTCAA<br>GCTCAACCGAGAGGACCTCCTTCGAAAGCAGCGAACCTTCGATAACGGCTCCA<br>TCCCCCACCAGATCCACCTGGGTGAGCTCCACGCCATTCTCCGAAGACAAGAG<br>GACTTCTACCCCTTCCTAAAGGATAACCGAGAGAAGATCGAGAAGATTCTCAC<br>CTTCCGAATCCCCTACTACGTCGGTCCCCTCGCTCGAGGTAACTCCCGATTTG<br>CTTGGATGACCCGAAAGTCCGAGGAGACTATCACCCCCTGGAACTTTGAAGAG<br>GTAGTCGACAAGGGTGCCTCCGCCCAGTCTTTCATTGAGCGGATGACCAACTT<br>CGATAAGAACCTCCCCAACGAGAAGGTCCTTCCCAAGCACTCTCTCCTCTACG<br>AGTACTTCACCGTCTACAACGAGCTGACCAAGGTCAAGTACGTTACCGAGGGC<br>ATGCGAAAGCCCGCTTTCCTCTCTGGTGAGCAGAAGAAGGCCATTGTCGACCT<br>CCTGTTCAAGACTAACCGAAAAGTCACCGTCAAGCAGCTCAAGGAAGACTACT<br>TCAAGAAGATTGAGTGCTTCGACTCCGTCGAGATTTCCGGTGTCGAGGACCGA<br>TTCAACGCCTCCCTCGGCACCTACCACGATCTTCTGAAGATCATCAAGGACAA | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | GGACTTTCTTGATAACGAGGAGAACGAGGACATTCTCGAGGACATCGTCCTCA<br>CCCTCACCCTTTTCGAGGATCGAGAGATGATCGAGGAGCGACTCAAGACCTAC<br>GCCCATCTCTTCGACGACAAGGTCATGAAGCAACTCAAGCGACGACGATACAC<br>TGGCTGGGGCCGACTTTCCCGAAAGCTCATCAACGGCATCCGAGACAAGCAGT<br>CTGGCAAGACCATCCTGGACTTCCTGAAGTCCGACGGTTTCGCCAACCGAAAC<br>TTCATGCAGCTCATCCACGACGACTCTCTTACCTTCAAAGAGGATATCCAGAA<br>GGCCCAGGTTTCTGGCCAGGGCGACTCCCTCCACGAGCACATTGCCAACCTCG<br>CCGGATCCCCCGCCATCAAAAAGGGTATCCTCCAGACCGTCAAGGTTGTCGAC<br>GAACTCGTGAAGGTCATGGGCCGACACAAGCCCGAGAACATCGTTATCGAGAT<br>GGCCCGAGAGAACCAGACCACCCAGAAGGGTCAGAAGAACTCCCGAGAGCGAA<br>TGAAGCGAATCGAAGAGGGTATCAAGGAGCTCGGTTCCCAGATTCTCAAGGAG<br>CACCCCGTCGAGAACACCCAGCTCCAGAACGAGAAACTCTACCTGTACTACCT<br>CCAGAATGGCCGAGACATGTACGTTGACCAGGAGCTCGACATCAACCGACTCT<br>CCGACTACGACGTCGACCACATTGTTCCTCAGTCCTTCCTCAAGGACGACTCC<br>ATCGACAACAAGGTTCTGACCCGATCTGACAAGAACCGAGGTAAGTCCGACAA<br>CGTTCCCTCCGAAGAGGTCGTTAAGAAGATGAAGAACTACTGGCGACAGCTTC<br>TCAACGCCAAACTGATCACCCAGCGAAAGTTTGACAACCTCACCAAGGCCGAG<br>CGAGGTGGTCTGTCCGAGCTGGACAAGGCCGGCTTCATTAAGCGACAGCTGGT<br>CGAGACTCGACAGATCACCAAGCACGTCGCCCAGATCCTCGACTCCCGAATGA<br>ACACCAAGTACGACGAGAACGACAAGCTCATCCGGGAGGTCAAGGTCATCACC<br>CTGAAGTCTAAGCTTGTCTCCGACTTCCGAAAGGACTTCCAGTTCTACAAGGT<br>CCGAGAGATCAACAACTACCACCACGCCCACGACGCCTACCTCAACGCCGTTG<br>TTGGTACCGCCCTCATCAAGAAGTATCCCAAGCTCGAGTCCGAGTTCGTTTAC<br>GGCGACTACAAGGTTTACGATGTCCGAAAGATGATTGCCAAGTCCGAGCAGGA<br>GATCGGTAAGGCCACCGCCAAGTACTTTTTCTACTCCAACATCATGAATTTCT<br>TCAAGACCGAGATCACTCTCGCCAACGGTGAGATTCGAAAGCGACCCCTGATT<br>GAGACTAATGGTGAGACTGGTGAGATCGTCTGGGATAAGGGCCGAGACTTCGC<br>CACCGTCCGAAAGGTCCTGTCCATGCCCCAGGTCAACATTGTCAAGAAGACCG<br>AGGTCCAGACCGGTGGCTTCTCCAAGGAGTCCATTCTCCCCAAGCGAAACTCC<br>GACAAACTCATCGCCCGTAAGAAGGACTGGGATCCGAAGAAGTACGGTGGTTT<br>CGATTCTCCCACCGTTGCCTACTCCGTCCTCGTTGTTGCTAAAGTCGAGAAGG<br>GTAAGTCTAAGAAACTCAAGTCCGTGAAGGAGCTACTCGGTATCACCATCATG<br>GAGCGATCTTCTTTTGAGAAGAACCCCATTGACTTCCTCGAGGCCAAGGGTTA<br>CAAAGAGGTCAAGAAGGACCTGATTATCAAGCTGCCCAAGTACTCCCTCTTTG<br>AGCTCGAGAACGGCCGAAAGCGAATGCTGGCTTCCGCTGGTGAGCTGCAGAAG<br>GGCAACGAGCTCGCTCTGCCCTCCAAGTACGTCAACTTCCTCTACCTGGCCTC<br>CCACTACGAGAAGCTCAAGGGCTCCCCCGAGGACAACGAGCAGAAGCAGCTGT<br>TCGTTGAGCAGCACAAGCACTACCTCGACGAGATCATCGAGCAGATCTCCGAG<br>TTCTCCAAGCGAGTCATCCTCGCTGACGCCAACCTTGATAAGGTTCTCTCTGC<br>TTACAACAAGCACCGGGACAAGCCCATCCGAGAGCAGGCCGAGAATATCATCC<br>ACCTCTTCACTCTCACCAACCTCGGCGCTCCTGCTGCCTTCAAGTACTTCGAC<br>ACCACCATTGACCGAAAGAGGTACACCTCCACCAAGGAAGTCCTCGACGCCAC<br>CCTGATCCACCAGTCCATCACCGGCCTCTACGAAACCCGAATCGACCTCTCCC<br>AGCTCGGCGGTGACTCTCGAGCCGACCCCAAGAAGAAGCGAAAAGTCTAAATA<br>TCCGAAGATCAAGAGCGAAGCAAGTTGTAAGTCCAGGACATGTTTCCCGCCCA<br>CGCGAGTGATTTATAACACCTCTCTTTTTTGACACCCGCTCGCCTTGAAATTC<br>ATGTCACATAAATTATAGTCAACGACGTTTGAATAACTTGTCTTGTAGTTCGA<br>TGATGATCATATGATTACATTAATAGTAATTACTGTATTTGATATATATACTA<br>ATTACAATAGTACATATTAGAACATACAATAGTTAGTGCCGTGAAGTGGCTTA<br>AAATACCGCGAGTCGATTACGTAATATTATTACCTCTTGCCCATCGAACGTAC<br>AAGTACTCCTCTGTTCTCTCCTTCCTTTGCTTTGTGCACGAAGAACTGCGGTC<br>AGGTGACACAACTTTTTCCATCTCAGGGTGTGTCGCGTGTGCTTCATCCAAAC<br>TTTAGTTGGGGTTCGGGTTCGCGCGAGATGATCACGTGCCCTGATTTGGTGTC<br>GTCCCCCGTCGCGCTGCGCACGTGATTTATTTATTTCCGGTGGCTGCTGTCTA<br>CGCGGGGCCTTCTCTGCCCTTCTGTTTCAACCTTCGGGCGGTTCTCGTAACCA<br>GCAGTAGCAATCCATTTCGAAACTCAAAGAGCTAAAAACGTTAAACCTCAGCA<br>GTCGCTCGACGAATGGGCTGCGGTTGGGAAGCCCACGAGGCCTATAGCCAGAG<br>CCTCGAGTTGACAGGAGCCCAGACGCCTTTTCCAACGGCAACTTTTATATAAA<br>ATGGCAATGTATTCATGCAATTGCGGCCGTGTCAGGTTGGAGACACTGGACCA<br>CACTCTCCATTGCTTCCTGAGGAGATGGATCATTGCTAGTGCATCTACGCGCA<br>GCAATCCCGCAAGCTCGACAACCGTAGATGGGCTTTGGTGGGCCAATCAATTA<br>CGCAACCCGCACGTTAAATTGTATGAGGAAGGAAGGCCACGGTACAAAGTGGG<br>TGGTCTTCACCCAGTGGTTGTTGGTGGCGTCATGCAGACCATGCATTGGGGAT<br>AGCACAGGGTTGGGGTGTCTTGTGGACTCAATGGGTGAAAGGAGATGGAAAAG<br>GGCGGTGAAAAGTGGTAGAATCGAAATCCCTGACGTCAATTTATAAAGTAAAA<br>TGCGTTTCTGCCATTTTGCTCCCCTCCTTCTTTCGCAATCGCCTCCCCAAAAG<br>TTGTCGTGGCAGTACACATGCTTGCATACAATGAAGCTAATCCGGCTTGCTCA<br>GTAGTTGCTATATCCAGGCATGGTGTGAAACCCCTCAAAGTATATATAGGAGC<br>GGTGAGCCCCAGTCTGGGGTCTTTTCTCTCCATCTCAAAACTACTTTCTCACA<br>ATGACGAGACTGATGAGTCCGTGAGGACGAAACGAGTAAGCTCGTCGAGGGCT<br>GCAAAATTCACGAGTTTTAGAGCTAGAAATAGCAAGTTAAAATAAGGCTAGTC | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CGTTATCAACTTGAAAAAGTGGCACCGAGTCGGTGCTTTTGGCCGGCATGGTC<br>CCAGCCTCCTCGCTGGCGCCGGCTGGGCAACATGCTTCGGCATGGCGAATGGG<br>ACTAAACTTCGAGCTAATCCAGTAGCTTACGTTACCCAGGGGCAGGTCAACTG<br>GCTAGCCACGAGTCTGTCCCAGGTCGCAATTTAGTGTAATAAACAATATATAT<br>ATTGAGTCTAAAGGGAATTGTAGCTATTGTGATTGTGTGATTTTCGTCTTGCT<br>GGTTCTTATTGTGTCCCATTCGTTTCATCCTGATGAGGACCCCTGGAACCGGT<br>GTTTTCTTAGTCTCTGCAATCGCTAGTCTTGTTGCTATGACAGTTGCGTCGAC<br>ACTATTCAGGTCATCTATCGGTTATTCTGATATTATAATACCTCCGGATCGAT<br>GTACCTGATTTATACTTGCAGCAATGTTTACTTCTTATCGTTGGACCCCGTCT<br>TCAATTACACTTCCCAACTGGGAACACCCCTCTTTATCGACCCATTTTAGGTA<br>ATTTACCCTAGCCCATTGTCTCCATAAGGAATATTACCCTAACCCACAGTCCA<br>GGGTGCCCAGGTCCTTCTTTGGCCAAATTTTAACTTCGGTCCTATGGCACAGC<br>GGTAGCGCGTGAGATTGCAAATCTTAAGGTCCCGAGTTCGAATCTCGGTGGGA<br>CCTAGTTGAAAAATACCTCTAATGCGCCGATGGTTTAGTGGTAAAATCCATCG<br>TTGCCATCGATGGGCCCCCGGTTCGATTCCGGGTCGGCGCAGGTTGACGTACA<br>GCAGGCTGAACGAGGATGTTTTAGAGCTAGAAATAGCAAGTTAAAATAAGGCT<br>AGTCCGTTATCAACTTGAAAAAGTGGCACCGAGTCGGTGCTTTTTTTTTTCGC<br>GATACACGAATGTGATACGGATCAAAGTAAGCAGGACTACGATAAGATAACGA<br>ATGCGGTGCAGTCCATGTCGATTAGGTATAGATACATTTATTTTGTGTTATGT<br>TACATTTTGGGGGGATACTGTCCTACTTGTAGTACCTACTTGTAGTGGCGCGT<br>CTATTCCTTTGCCCTCGGACGAGTGCTGGGGCGTCGGTTTCCACTATCGGCGA<br>GTACTTCTACACAGCCATCGGTCCAGACGGCCGCGCTTCTGCGGGCGATTTGT<br>GTACGCCCGACAGTCCCGGCTCCGGATCGGACGATTGCGTCGCATCGACCCTG<br>CGCCCAAGCTGCATCATCGAAATTGCCGTCAACCAAGCTCTGATAGAGTTGGT<br>CAAGACCAATGCGGAGCATATACGCCCGGAGCCGCGGCGATCCTGCAAGCTCC<br>GGATGCCTCCGCTCGAAGTAGCGCGTCTGCTGCTCCATACAAGCCAACCACGG<br>CCTCCAGAAGAAGATGTTGGCGACCTCGTATTGGGAATCCCCGAACATCGCCT<br>CGCTCCAGTCAATGACCGCTGTTATGCGGCCATTGTCCGTCAGGACATTGTTG<br>GAGCCGAAATCCGCGTGCACGAGGTGCCGGACTTCGGGGCAGTCCTCGGCCCA<br>AAGCATCAGCTCATCGAGAGCCTGCGCGACGGACGCACTGACGGTGTCGTCCA<br>TCACAGTTTGCCAGTGATACACATGGGGATCAGCAATCGCGCATATGAAATCA<br>CGCCATGTAGTGTATTGACCGATTCCTTGCGGTCCGAATGGGCCGAACCCGCT<br>CGTCTGGCTAAGATCGGCCGCAGCGATCGCATCCATGGCCTCCGCGACCGGCT<br>GCAGAACAGCGGGCAGTTCGGTTTCAGGCAGGTCTTGCAACGTGACACCCTGT<br>GCACGGCGGGAGATGCAATAGGTCAGGCTCTCGCTGAATTCCCCAATGTCAAG<br>CACTTCCGGAATCGGGAGCGCGGCCGATGCAAAGTGCCGATAAACATAACGAT<br>CTTTGTAGAAACCATCGGCGCAGCTATTTACCCGCAGGACATATCCACGCCCT<br>CCTACATCGAAGCTGAAAGCACGAGATTCTTCGCCCTCCGAGAGCTGCATCAG<br>GTCGGAGACGCTGTCGAACTTTTCGATCAGAAACTTCTCGACAGACGTCGCGG<br>TGAGTTCAGGCTTTTTCATATGGGTACCTGAGAACATTTTTGTGTCTAGGTGT<br>TTGTGTTTGGACTGCGATCAGTGAAGAAAAGAAGAGGAAAAATTGTGCAAGAA<br>ATTTTGCTTTCAAGACTTGGCTGATGCAGCAGGGTAACTCTGGGACACAGACC<br>TATGTTTGTGGTTAAACTCAATGCACGTGGTACGTGCGTGGAGCGCTTACCCA<br>TCCAAGGGTGTGGACATGGAACCGACGGTCCGTGGAGTTGTGTAATGTCATTT<br>TGGCGACTCTTGAAGCAAGGCTATAAAAAAATTGTGTGGCTTGAGTCTTATCG<br>AGCTCGGTCACTACAAGAGTTAATCTTCCTGTCTCAGGCAGACAGGTCAGGCA<br>GGGTTACTTTTGGGTGTGCTGTAACTCACTGTATGGCCGTTAGTGCGCATAGA<br>CGTTGTACATACTGGACCGAATTGTAGCGTGCTCAATAGGGCCAATAAAGCTA<br>TTGTAGGGATCCGAATTTTCAGAACCTAATTTATCTGTTACCCGGCCTGTGGC<br>TCGCACAGCTTAAAAATGGTCAAACTTTCCCCTTCTTGTCTTTTTTTCCTCAC<br>ATTCATCAGGTTCTTGTCTTGATCTTTCAAGTGAGTATTAATTACCGACCTTG<br>GTTCTTCATTGGGAGAGCATTGGAAGCCGTGGTGCAGCAACCACAAAACGGTT<br>CTTCCCCTTCGATACCTTCTTGCCTGCCTTTCAATACAAGTCGGCTCGATTAG<br>CGGTGGTCGCCCCCGCCAGCGGAGAACATGGAACTAACCCAGAATGAGAGCTA<br>AGTGGAGAAAGAAGAGAGTCAGACGACTCAAGCGAAAGCGCCGCAAGGTCCGA<br>GCTCGATCCAAATAAGCGGTTTTTAACGGAGATTTAACACTAAATCGAAGAAC<br>TTTTCCCGTTTCATTTGCGAATGAGCTCGTTAACAAAATCCCCCAGTTTTTTT<br>ATCCAGCTGTAAGGATTGACATTAGTAATGAATTATTGTTTGGTATATTTAAA<br>TCTGTAGTTCCTTTCTGTCCGTGTCGGCAACTGTCGTACTCGTGATTTACTTG<br>TATTGACGAATACTTACTGTAGCGCACTCTGCTGCTACTGGTCGTAAGGATGT<br>GCTATTTCGGTGTATGGTGGGTTTTTTGGGGGTCGGAACCGAAGACTGTTACA<br>CGGGCACGGCTCGTTGTGTACACGCACAGAGCTCTTGCGAGTCATGTTGTAGC<br>TAGCTCGTCGTGTTCAGGAACTGTTCGATGGTTCGGAGAGAGTCGCCGCCCAG<br>AACATACGCGCACCGATGTCAGCAGACAGCCTTATTACAAGTATATTCAAGCA<br>AGTATATCCGTAGGGTGCGGGTGATTTGGATCTAAGGTTCGTACTCAACACTC<br>ACGAGCAGCTTGCCTATGTTACATCCTTTTATCAGACATAACATAATTGGAGT<br>TTACTTACACACGGGGTGTACCTGTATGAGCACCACCTACAATTGTAGCACTG<br>GTACTTGTACAAAGAATTTATTCGTACGAATCACAGGGACGGCCGCCCTCACC<br>GAACCAGCGAATACCTCAGCGGTCCCCTGCAGTGACTCAACAAAGCGATATGA<br>ACATCTTGCGATGGTATCCTGCTGATAGTTTTTACTGTACAAACACCTGTGTA<br>GCTCCTTCTAGCATTTTTAAGTTATTCACACCTCAAGGGGAGGGATAAATTAA | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | ATAAATTCCAAAAGCGAAGATCGAGAAACTAAATTAAAATTCCAAAAACGAAG | |
| | TTGGAACACAACCCCCCGAAAAAAAACAACAAACAAAAAACCCAACAAAATAA | |
| | ACAAAAACAAAATAAATATATAACTACCAGTATCTGACTAAAAGTTCAAATAC | |
| | TCGTACTTACAACAAATAGAAATGAGCCGGCCAAAATTCTGCAGAAAAAAATT | |
| | TCAAACAAGTACTGGTATAATTAAATTAAAAAACACATCAAAGTATCATAACG | |
| | TTAGTTATTTTATTTTATTTAATAAAAGAAAACAACAAGATGGGCTCAAAACT | |
| | TTCAACTTATACGATACATACCAAATAACAATTTAGTATTTATCTAAGTGCTT | |
| | TTCGTAGATAATGGAATACAAATGGATATCCAGAGTATACACATGGATAGTAT | |
| | ACACTGACACGACAATTCTGTATCTCTTTATGTTAACTACTGTGAGGCATTAA | |
| | ATAGAGCTTGATATATAAAATGTTACATTTCACAGTCTGAACTTTTGCAGATT | |
| | ACCTAATTTGGTAAGATATTAATTATGAACTGAAAGTTGATGGCATCCCTAAA | |
| | TTTGATGAAAGATGAAATTGTAAATGAGGTGGTAAAAGAGCTACAGTCGTTTT | |
| | GTTTTGAGATACCATCATCTCTAACGAAATATCTATTAAAAATCTCAGTGTGA | |
| | TCATGAGTCATTGCCATCCTGGAAAATGTCATCATGGCTGATATTTCTAACTG | |
| | TTTACTTGAGATAAATATATATTTACAAGAACTTCCCTTGAAATTAATTTAGA | |
| | TATAAAATGTTTGCGGGCAAGTTACTACGAGGAATAAATTATATCTAGAAAGC | |
| | GGAAGAGCGCCCAATACGCAAACCGCCTCTCCCCGCGCGTTGGCCGATTCATT | |
| | AATGCAGCTGGCACGACAGGTTTCCCGACTGGAAAGCGGGCAGTGAGCGCAAC | |
| | GCAATTAATGTGAGTTAGCTCACTCATTAGGCACCCCAGGCTTTACACTTTAT | |
| | GCTTCCGGCTCGTATGTTGTGTGGAATTGTGAGCGGATAACAATTTCACACAG | |
| | GAAACAGCTATGACCATGATTACGCCAAGCTTGGTACCAGAGACGGGTTGGCG | |
| | GCGTATTTGTGTCCCAAAAAACAGCCCCAATTGCCCCAATTGACCCCAAATTG | |
| | ACCCAGTAGCGGGCCCAACCCCGGCGAGAGCCCCCTTCACCCCACATATCAAA | |
| | CCTCCCCCGGTTCCCACACTTGCCGTTAAGGGCGTAGGGTACTGCAGTCTGGA | |
| | ATCTACGCTTGTTCAGACTTTGTACTAGTTTCTTTGTCTGGCCATCCGGGTAA | |
| | CCCATGCCGGACGCAAAATAGACTACTGAAAATTTTTTTGCTTTGTGGTTGGG | |
| | ACTTTAGCCAAGGGTATAAAAGACCACCGTCCCCGAATTACCTTTCCTCTTCT | |
| | TTTCTCTCTCTCCTTGTCAACTCACACCCGAAATCGTTAAGCATTTCCTTCTG | |
| | AGTATAAGAATCATTCGCTAGCCACAAAAATGATGGCTCCCTCCATTCGAAAG | |
| | TTCTTTGCTGGTGGTGTGTGTCGAACTAACGTTCAGCTTCCCGGTAAGGTGGT | |
| | TGTCATCACTGGTGCCAACACCGGCATTGGCAAGGAGACTGCCCGAGAGCTCG | |
| | CTTCCCGAGGAGCCCGAGTTTACATTGCTTGCCGAGATGTTCTGAAGGGCGAG | |
| | TCTGCTGCCTCTGAGATTCGAGTTGACACTAAGAACTCCCAGGTGCTCGTGCG | |
| | AAAGCTCGACCTTTCCGACACTAAGTCTATCCGAGCCTTTGCTGAGGGCTTTC | |
| | TCGCTGAGGAGAAGCAGCTTCACATTCTGATTAACAACGCTGGAGTTATGATG | |
| | TGTCCTTACTCTAAGACTGCTGATGGTTTCGAGACTCACCTCGGAGTCAACCA | |
| | CCTGGGCCACTTCCTCCTCACCTACCTGCTCCTGGAGCGACTCAAGGTGTCTG | |
| | CCCCTGCCCGAGTGGTTAACGTTTCCTCCGTGGCTCACCACATTGGCAAGATT | |
| | CCCTTCCACGACCTCCAGTCCGAGAAGCGATACTCCCGAGGTTTTGCTTACTG | |
| | CCACTCCAAGCTGGCCAACGTTCTCTTTACCCGAGAGCTGGCCAAGCGACTCC | |
| | AGGGAACCGGCGTCACCACCTACGCCGTTCACCCCGGTGTCGTCCGATCCGAG | |
| | CTGGTCCGACACTCCTCCCTGCTCTGCCTGCTCTGGCGACTCTTCTCCCCCTT | |
| | CGTTAAGACCGCCCGAGAGGGTGCCCAGACCTCCCTGCACTGCGCCCTGGCTG | |
| | AGGGCCTGGAGCCCCTGTCTGGCAAGTACTTCTCTGACTGCAAGCGAACCTGG | |
| | GTGTCTCCCCGAGCTCGAAACAACAAGACTGCCGAGCGACTCTGGAACGTTTC | |
| | CTGTGAGCTTCTCGGTATTCGATGGGAGTAGACGCGTGCAATTAACAGATAGT | |
| | TTGCCGGTGATAATTCTCTTAACCTCCCACACTCCTTTGACATAACGATTTAT | |
| | GTAACGAAACTGAAATTTGACCAGATATTGTTGTAAATAGAAAATCTGGCTTG | |
| | TAGGTGGCAAACTAGTGGTGTGTTCTGTGGAGCATTCTCACTTTTGGTAAACG | |
| | ACATTGCTTCAAGTGCAGCGGAATCAAAAAGTATAAAGTGGGCAGCGAGTATA | |
| | CCTGTACAGACTGTAGGCGATAACTCAATCCAATTACCCCCCACAACATGACT | |
| | GGCCAAACTGATCTCAAGACTTTATTGAAATCAGCAACACCGATTCTCAATGA | |
| | AGGCACATACTTCTTCTGCAACATTCACTTGACGCCTAAAGTTGGTGAGAAAT | |
| | GGACCGACAAGACATATTCTGCTATCCACGGACTGTTGCCTGTGTCGGTGGCT | |
| | ACAATACGTGAGTCAGAAGGGCTGACGGTGGTGGTTCCCAAGGAAAAGGTCGA | |
| | CGAGTATCTGTCTGACTCGTCATTGCCGCCTTTGGAGTACGACTCCAACTATG | |
| | AGTGTGCTTGGATCACTTTGACGATACATTCTTCGTTGGAGGCTGTGGGTCTG | |
| | ACAGCTGCGTTTTCGGCGCGGTTGGCCGACAACAATATCAGCTGCAACGTCAT | |
| | TGCTGGCTTTCATCATGATCACATTTTTGTCGGCAAAGGCGACGCCCAGAGAG | |
| | CCATTGACGTTCTTTCTAATTTGGACCGATAGCCGTATAGTCCAGTCTATCTA | |
| | TAAGTTCAACTAACTCGTAACTATTACCATAACATATACTTCACTGCCCCAGA | |
| | TAAGGTTCCGATAAAAAGTTCTGCAGACTAAATTTATTTCAGTCTCCTCTTCA | |
| | CCACCAAAATGCCCTCCTACGAAGCTCGAGCTAACGTCCACAAGTCCGCCTTT | |
| | GCCGCTCGAGTGCTCAAGCTCGTGGCAGCCAAGAAAACCAACCTGTGTGCTTC | |
| | TCTGGATGTTACCACCACCAAGGAGCTCATTGAGCTTGCCGATAAGGTCGGAC | |
| | CTTATGTGTGCATGATCAAGACCCATATCGACATCATTGACGACTTCACCTAC | |
| | GCCGGCACTGTGCTCCCCCTCAAGGAACTTGCTCTTAAGCACGGTTTCTTCCT | |
| | GTTCGAGGACAGAAAGTTCGCAGATATTGGCAACACTGTCAAGCACCAGTACA | |
| | AGAACGGTGTCTACCGAATCGCCGAGTGGTCCGATATCACCAACGCCCACGGT | |
| | GTACCCGGAACCGGAATCATTGCTGGCCTGCGAGCTGGTGCCGAGGAAACTGT | |
| | CTCTGAACAGAAGAAGGAGGACGTCTCTGACTACGAGAACTCCCAGTACAAGG | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | AGTTCCTGGTCCCCTCTCCCAACGAGAAGCTGGCCAGAGGTCTGCTCATGCTG | |
| | GCCGAGCTGTCTTGCAAGGGCTCTCTGGCCACTGGCGAGTACTCCAAGCAGAC | |
| | CATTGAGCTTGCCCGATCCGACCCCGAGTTTGTGGTTGGCTTCATTGCCCAGA | |
| | ACCGACCTAAGGGCGACTCTGAGGACTGGCTTATTCTGACCCCCGGGGTGGGT | |
| | CTTGACGACAAGGGAGACGCTCTCGGACAGCAGTACCGAACTGTTGAGGATGT | |
| | CATGTCTACCGGAACGGATATCATAATTGTCGGCCGAGGTCTGTACGGCCAGA | |
| | ACCGAGATCCTATTGAGGAGGCCAAGCGATACCAGAAGGCTGGCTGGGAGGCT | |
| | TACCAGAAGATTAACTGTTAGAGGTTAGACTATGGATATGTAATTTAACTGTG | |
| | TATATAGAGAGCGTGCAAGTATGGAGCGCTTGTTCAGCTTGTATGATGGTCAG | |
| | ACGACCTGTCTGATCGAGTATGTATGATACTGCACAACCTGTGTATCCGCATG | |
| | ATCTGTCCAATGGGGCATGTTGTTGTGTTTCTCGATACGGAGATGCTGGGTAC | |
| | AAGTAGCTAATACGATTGAACTACTTATACTTATATGAGGCTTGAAGAAAGCT | |
| | GACTTGTGTATGACTTATTCTCAACTACATCCCCAGTCACAATACCACCACTG | |
| | CACTACCACTACACCTCGAGCATGCATCTAGTGGTGTGTTCTGTGGAGCATTC | |
| | TCACTTTTGGTAAACGACATTGCTTCAAGTGCAGCGGAATCAAAAAGTATAAA | |
| | GTGGGCAGCGAGTATACCTGTACAGACTGTAGGCGATAACTCAATCCAATTAC | |
| | CCCCCACAACATGACTGGCCAAACTGATCTCAAGACTTTATTGAAATCAGCAA | |
| | CACCGATTCTCAATGAAGGCACATACTTCTTCTGCAACATTCACTTGACGCCT | |
| | AAAGTTGGTGAGAAATGGACCGACAAGACATATTCTGCTATCCACGGACTGTT | |
| | GCCTGTGTCGGTGGCTACAATACGTGAGTCAGAAGGGCTGACGGTGGTGGTTC | |
| | CCAAGGAAAAGGTCGACGAGTATCTGTCTGACTCGTCATTGCCGCCTTTGGAG | |
| | TACGACTCCAACTATGAGTGTGCTTGGATCACTTTGACGATACATTCTTCGTT | |
| | GGAGGCTGTGGGTCTGACAGCTGCGTTTTCGGCGCGGTTGGCCGACAACAATA | |
| | TCAGCTGCAACGTCATTGCTGGCTTTCATCATGATCACATTTTTGTCGGCAAA | |
| | GGCGACGCCCAGAGAGCCATTGACGTTCTTTCTAATTTGGACCGATAGCCGTA | |
| | TAGTCCAGTCTATCTATAAGTTCAACTAACTCGTAACTATTACCATAACATAT | |
| | ACTTCACTGCCCCAGATAAGGTTCCGATAAAAAGTTCTGCAGACTAAATTTAT | |
| | TTCAGTCTCCTCTTCACCACCAAAATGCCCTCCTACGAAGCTCGAGCTAACGT | |
| | CCACAAGTCCGCCTTTGCCGCTCGAGTGCTCAAGCTCGTGGCAGCCAAGAAAA | |
| | CCAACCTGTGTGCTTCTCTGGATGTTACCACCACCAAGGGGCCGCTCGAGCAT | |
| | GCATCTAGAGGGCCCAATTCGCCCTATAGTGAGTCGTATTACAATTCACTGGC | |
| | CGTCGTTTTACAACGTCGTGACTGGGAAAACCCTGGCGTTACCCAACTTAATC | |
| | GCCTTGCAGCACATCCCCCTTTCGCCAGCTGGCGTAATAGCGAAGAGGCCCGC | |
| | ACCGATCGCCCTTCCCAACAGTTGCGCAGCCTGAATGGCGAATGGACGCGCCC | |
| | TGTAGCGGCGCATTAAGCGCGGCGGGTGTGGTGGTTACGCGCAGCGTGACCGC | |
| | TACACTTGCCAGCGCCCTAGCGCCCGCTCCTTTCGCTTTCTTCCCTTCCTTTC | |
| | TCGCCACGTTCGCCGGCTTTCCCCGTCAAGCTCTAAATCGGGGGCTCCCTTTA | |
| | GGGTTCCGATTTAGTGCTTTACGGCACCTCGACCCCAAAAAACTTGATTAGGG | |
| | TGATGGTTCACGTAGTGGGCCATCGCCCTGATAGACGGTTTTTCGCCCTTTGA | |
| | CGTTGGAGTCCACGTTCTTTAATAGTGGACTCTTGTTCCAAACTGGAACAACA | |
| | CTCAACCCTATCTCGGTCTATTCTTTTGATTTATAAGGGATTTTGCCGATTTC | |
| | GGCCTATTGGTTAAAAAATGAGCTGATTTAACAAAAATTTAACGCGAATTTTA | |
| | ACAAAATTCAGGGCGCAAGGGCTGCTAAAGGAAGCGGAACACGTAGAAAGCCA | |
| | GTCCGCAGAAACGGTGCTGACCCCGGATGAATGTCAGCTACTGGGCTATCTGG | |
| | ACAAGGGAAAACGCAAGCGCAAAGAGAAAGCAGGTAGCTTGCAGTGGGCTTAC | |
| | ATGGCGATAGCTAGACTGGGCGGTTTTATGGACAGCAAGCGAACCGGAATTGC | |
| | CAGCTGGGGCGCCCTCTGGTAAGGTTGGGAAGCCCTGCAAAGTAAACTGGATG | |
| | GCTTTCTTGCCGCCAAGGATCTGATGGCGCAGGGGATCAAGATCTGATCAAGA | |
| | GACAGGATGAGGATCGTTTCGCATGATTGAACAAGATGGATTGCACGCAGGTT | |
| | CTCCGGCCGCTTGGGTGGAGAGGCTATTCGGCTATGACTGGGCACAACAGACA | |
| | ATCGGCTGCTCTGATGCCGCCGTGTTCCGGCTGTCAGCGCAGGGGCGCCCGGT | |
| | TCTTTTTGTCAAGACCGACCTGTCCGGTGCCCTGAATGAACTGCAGGACGAGG | |
| | CAGCGCGGCTATCGTGGCTGGCCACGACGGGCGTTCCTTGCGCAGCTGTGCTC | |
| | GACGTTGTCACTGAAGCGGGAAGGGACTGGCTGCTATTGGGCGAAGTGCCGGG | |
| | GCAGGATCTCCTGTCATCCCACCTTGCTCCTGCCGAGAAAGTATCCATCATGG | |
| | CTGATGCAATGCGGCGGCTGCATACGCTTGATCCGGCTACCTGCCCATTCGAC | |
| | CACCAAGCGAAACATCGCATCGAGCGAGCACGTACTCGGATGGAAGCCGGTCT | |
| | TGTCGATCAGGATGATCTGGACGAAGAGCATCAGGGGCTCGCGCCAGCCGAAC | |
| | TGTTCGCCAGGCTCAAGGCGCGCATGCCCGACGGCGAGGATCTCGTCGTGACC | |
| | CATGGCGATGCCTGCTTGCCGAATATCATGGTGGAAAATGGCCGCTTTTCTGG | |
| | ATTCATCGACTGTGGCCGGCTGGGTGTGGCGGACCGCTATCAGGACATAGCGT | |
| | TGGCTACCCGTGATATTGCTGAAGAGCTTGGCGGCGAATGGGCTGACCGCTTC | |
| | CTCGTGCTTTACGGTATCGCCGCTCCCGATTCGCAGCGCATCGCCTTCTATCG | |
| | CCTTCTTGACGAGTTCTTCTGAATTGAAAAAGGAAGAGTATGAGTATTCAACA | |
| | TTTCCGTGTCGCCCTTATTCCCTTTTTTGCGGCATTTTGCCTTCCTGTTTTTG | |
| | CTCACCCAGAAACGCTGGTGAAAGTAAAAGATGCTGAAGATCAGTTGGGTGCA | |
| | CGAGTGGGTTACATCGAACTGGATCTCAACAGCGGTAAGATCCTTGAGAGTTT | |
| | TCGCCCCGAAGAACGTTTTCCAATGATGAGCACTTTTAAAGTTCTGCTATGTG | |
| | GCGCGGTATTATCCCGTATTGACGCCGGGCAAGAGCAACTCGGTCGCCGCATA | |
| | CACTATTCTCAGAATGACTTGGTTGAGTACTCACCAGTCACAGAAAAGCATCT | |
| | TACGGATGGCATGACAGTAAGAGAATTATGCAGTGCTGCCATAACCATGAGTG | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | ATAACACTGCGGCCAACTTACTTCTGACAACGATCGGAGGACCGAAGGAGCTA | |
| | ACCGCTTTTTTGCACAACATGGGGGATCATGTAACTCGCCTTGATCGTTGGGA | |
| | ACCGGAGCTGAATGAAGCCATACCAAACGACGAGCGTGACACCACGATGCCTG | |
| | TAGCAATGGCAACAACGTTGCGCAAACTATTAACTGGCGAACTACTTACTCTA | |
| | GCTTCCCGGCAACAATTAATAGACTGGATGGAGGCGGATAAAGTTGCAGGACC | |
| | ACTTCTGCGCTCGGCCCTTCCGGCTGGCTGGTTTATTGCTGATAAATCTGGAG | |
| | CCGGTGAGCGTGGGTCTCGCGGTATCATTGCAGCACTGGGGCCAGATGGTAAG | |
| | CCCTCCCGTATCGTAGTTATCTACACGACGGGGAGTCAGGCAACTATGGATGA | |
| | ACGAAATAGACAGATCGCTGAGATAGGTGCCTCACTGATTAAGCATTGGTAAC | |
| | TGTCAGACCAAGTTTACTCATATATACTTTAGATTGATTTAAAACTTCATTTT | |
| | TAATTTAAAAGGATCTAGGTGAAGATCCTTTTTGATAATCTCATGACCAAAAT | |
| | CCCTTAACGTGAGTTTTCGTTCCACTGAGCGTCAGACCCCGTAGAAAAGATCA | |
| | AAGGATCTTCTTGAGATCCTTTTTTTCTGCGCGTAATCTGCTGCTTGCAAACA | |
| | AAAAAACCACCGCTACCAGCGGTGGTTTGTTTGCCGGATCAAGAGCTACCAAC | |
| | TCTTTTTCCGAAGGTAACTGGCTTCAGCAGAGCGCAGATACCAAATACTGTTC | |
| | TTCTAGTGTAGCCGTAGTTAGGCCACCACTTCAAGAACTCTGTAGCACCGCCT | |
| | ACATACCTCGCTCTGCTAATCCTGTTACCAGTGGCTGCTGCCAGTGGCGATAA | |
| | GTCGTGTCTTACCGGGTTGGACTCAAGACGATAGTTACCGGATAAGGCGCAGC | |
| | GGTCGGGCTGAACGGGGGGTTCGTGCACACAGCCCAGCTTGGAGCGAACGACC | |
| | TACACCGAACTGAGATACCTACAGCGTGAGCTATGAGAAAGCGCCACGCTTCC | |
| | CGAAGGGAGAAAGGCGGACAGGTATCCGGTAAGCGGCAGGGTCGGAACAGGAG | |
| | AGCGCACGAGGGAGCTTCCAGGGGGAAACGCCTGGTATCTTTATAGTCCTGTC | |
| | GGGTTTCGCCACCTCTGACTTGAGCGTCGATTTTTGTGATGCTCGTCAGGGGG | |
| | GCGGAGCCTATGGAAAAACGCCAGCAACGCGGCCTTTTTACGGTTCCTGGCCT | |
| | TTTGCTGGCCTTTTGCTCACATGTTCTTTCCTGCGTTATCCCCTGATTCTGTG | |
| | GATAACCGTATTACCGCCTTTGAGTGAGCTGATACCGCTCGCCGCAGCCGAAC | |
| | GACCGAGCGCAGCGAGTCAGTGAGCGAGG | |
| MB8203 | AAGCGGAAGAGCGCCCAATACGCAAACCGCCTCTCCCCGCGCGTTGGCCGATT | 10 |
| | CATTAATGCAGCTGGCACGACAGGTTTCCCGACTGGAAAGCGGGCAGTGAGCG | |
| | CAACGCAATTAATGTGAGTTAGCTCACTCATTAGGCACCCCAGGCTTTACACT | |
| | TTATGCTTCCGGCTCGTATGTTGTGTGGAATTGTGAGCGGATAACAATTTCAC | |
| | ACAGGAAACAGCTATGACCATGATTACGCCAAGCTTGGTACCAGAGACGGGTT | |
| | GGCGGCGTATTTGTGTCCCAAAAAACAGCCCCAATTGCCCCAATTGACCCCAA | |
| | ATTGACCCAGTAGCGGGCCCAACCCCGGCGAGAGCCCCCTTCACCCCACATAT | |
| | CAAACCTCCCCCGGTTCCCACACTTGCCGTTAAGGGCGTAGGGTACTGCAGTC | |
| | TGGAATCTACGCTTGTTCAGACTTTGTACTAGTTTCTTTGTCTGGCCATCCGG | |
| | GTAACCCATGCCGGACGCAAAATAGACTACTGAAAATTTTTTTGCTTTGTGGT | |
| | TGGGACTTTAGCCAAGGGTATAAAAGACCACCGTCCCCGAATTACCTTTCCTC | |
| | TTCTTTTCTCTCTCTCCTTGTCAACTCACACCCGAAATCGTTAAGCATTTCCT | |
| | TCTGAGTATAAGAATCATTCGCTAGCCACAAAAATGATGGCTCCCTCCATTCG | |
| | AAAGTTCTTTGCTGGTGGTGTGTGTCGAACTAACGTTCAGCTTCCCGGTAAGG | |
| | TGGTTGTCATCACTGGTGCCAACACCGGCATTGGCAAGGAGACTGCCCGAGAG | |
| | CTCGCTTCCCGAGGAGCCCGAGTTTACATTGCTTGCCGAGATGTTCTGAAGGG | |
| | CGAGTCTGCTGCCTCTGAGATTCGAGTTGACACTAAGAACTCCCAGGTGCTCG | |
| | TGCGAAAGCTCGACCTTTCCGACACTAAGTCTATCCGAGCCTTTGCTGAGGGC | |
| | TTTCTCGCTGAGGAGAAGCAGCTTCACATTCTGATTAACAACGCTGGAGTTAT | |
| | GATGTGTCCTTACTCTAAGACTGCTGATGGTTTCGAGACTCACCTCGGAGTCA | |
| | ACCACCTGGGCCACTTCCTCCTCACCTACCTGCTCCTGGAGCGACTCAAGGTG | |
| | TCTGCCCCTGCCCGAGTGGTTAACGTTTCCTCCGTGGCTCACCACATTGGCAA | |
| | GATTCCCTTCCACGACCTCCAGTCCGAGAAGCGATACTCCCGAGGTTTTGCTT | |
| | ACTGCCACTCCAAGCTGGCCAACGTTCTCTTTACCCGAGAGCTGGCCAAGCGA | |
| | CTCCAGGGAACCGGCGTCACCACCTACGCCGTTCACCCCGGTGTCGTCCGATC | |
| | CGAGCTGGTCCGACACTCCTCCCTGCTCTGCCTGCTCTGGCGACTCTTCTCCC | |
| | CCTTCGTTAAGACCGCCCGAGAGGGTGCCCAGACCTCCCTGCACTGCGCCCTG | |
| | GCTGAGGGCCTGGAGCCCCTGTCTGGCAAGTACTTCTCTGACTGCAAGCGAAC | |
| | CTGGGTGTCTCCCCGAGCTCGAAACAACAAGACTGCCGAGCGACTCTGGAACG | |
| | TTTCCTGTGAGCTTCTCGGTATTCGATGGGAGTAGACGCGTGCAATTAACAGA | |
| | TAGTTTGCCGGTGATAATTCTCTTAACCTCCCACACTCCTTTGACATAACGAT | |
| | TTATGTAACGAAACTGAAATTTGACCAGATATTGTTGTAAATAGAAAATCTGG | |
| | CTTGTAGGTGGCAAACTAGTGGTGTGTTCTGTGGAGCATTCTCACTTTTGGTA | |
| | AACGACATTGCTTCAAGTGCAGCGGAATCAAAAAGTATAAAGTGGGCAGCGAG | |
| | TATACCTGTACAGACTGTAGGCGATAACTCAATCCAATTACCCCCCACAACAT | |
| | GACTGGCCAAACTGATCTCAAGACTTTATTGAAATCAGCAACACCGATTCTCA | |
| | ATGAAGGCACATACTTCTTCTGCAACATTCACTTGACGCCTAAAGTTGGTGAG | |
| | AAATGGACCGACAAGACATATTCTGCTATCCACGGACTGTTGCCTGTGTCGGT | |
| | GGCTACAATACGTGAGTCAGAAGGGCTGACGGTGGTGGTTCCCAAGGAAAAGG | |
| | TCGACGAGTATCTGTCTGACTCGTCATTGCCGCCTTTGGAGTACGACTCCAAC | |
| | TATGAGTGTGCTTGGATCACTTTGACGATACATTCTTCGTTGGAGGCTGTGGG | |
| | TCTGACAGCTGCGTTTTCGGCGCGGTTGGCCGACAACAATATCAGCTGCAACG | |
| | TCATTGCTGGCTTTCATCATGATCACATTTTTGTCGGCAAAGGCGACGCCCAG | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | AGAGCCATTGACGTTCTTTCTAATTTGGACCGATAGCCGTATAGTCCAGTCTA<br>TCTATAAGTTCAACTAACTCGTAACTATTACCATAACATATACTTCACTGCCC<br>CAGATAAGGTTCCGATAAAAAGTTCTGCAGACTAAATTTATTTCAGTCTCCTC<br>TTCACCACCAAAATGCCCTCCTACGAAGCTCGAGCTAACGTCCACAAGTCCGC<br>CTTTGCCGCTCGAGTGCTCAAGCTCGTGGCAGCCAAGAAAACCAACCTGTGTG<br>CTTCTCTGGATGTTACCACCACCAAGGAGCTCATTGAGCTTGCCGATAAGGTC<br>GGACCTTATGTGTGCATGATCAAGACCCATATCGACATCATTGACGACTTCAC<br>CTACGCCGGCACTGTGCTCCCCCTCAAGGAACTTGCTCTTAAGCACGGTTTCT<br>TCCTGTTCGAGGACAGAAAGTTCGCAGATATTGGCAACACTGTCAAGCACCAG<br>TACAAGAACGGTGTCTACCGAATCGCCGAGTGGTCCGATATCACCAACGCCCA<br>CGGTGTACCCGGAACCGGAATCATTGCTGGCCTGCGAGCTGGTGCCGAGGAAA<br>CTGTCTCTGAACAGAAGAAGGAGGACGTCTCTGACTACGAGAACTCCCAGTAC<br>AAGGAGTTCCTGGTCCCCTCTCCCAACGAGAAGCTGGCCAGAGGTCTGCTCAT<br>GCTGGCCGAGCTGTCTTGCAAGGGCTCTCTGGCCACTGGCGAGTACTCCAAGC<br>AGACCATTGAGCTTGCCCGATCCGACCCCGAGTTTGTGGTTGGCTTCATTGCC<br>CAGAACCGACCTAAGGGCGACTCTGAGGACTGGCTTATTCTGACCCCCGGGGT<br>GGGTCTTGACGACAAGGGAGACGCTCTCGGACAGCAGTACCGAACTGTTGAGG<br>ATGTCATGTCTACCGGAACGGATATCATAATTGTCGGCCGAGGTCTGTACGGC<br>CAGAACCGAGATCCTATTGAGGAGGCCAAGCGATACCAGAAGGCTGGCTGGGA<br>GGCTTACCAGAAGATTAACTGTTAGAGGTTAGACTATGGATATGTAATTTAAC<br>TGTGTATATAGAGAGCGTGCAAGTATGGAGCGCTTGTTCAGCTTGTATGATGG<br>TCAGACGACCTGTCTGATCGAGTATGTATGATACTGCACAACCTGTGTATCCG<br>CATGATCTGTCCAATGGGGCATGTTGTTGTGTTTCTCGATACGGAGATGCTGG<br>GTACAAGTAGCTAATACGATTGAACTACTTATACTTATATGAGGCTTGAAGAA<br>AGCTGACTTGTGTATGACTTATTCTCAACTACATCCCCAGTCACAATACCACC<br>ACTGCACTACCACTACACCTCGAGCATGCATCTAGTGGTGTGTTCTGTGGAGC<br>ATTCTCACTTTTGGTAAACGACATTGCTTCAAGTGCAGCGGAATCAAAAAGTA<br>TAAAGTGGGCAGCGAGTATACCTGTACAGACTGTAGGCGATAACTCAATCCAA<br>TTACCCCCCACAACATGACTGGCCAAACTGATCTCAAGACTTTATTGAAATCA<br>GCAACACCGATTCTCAATGAAGGCACATACTTCTTCTGCAACATTCACTTGAC<br>GCCTAAAGTTGGTGAGAAATGGACCGACAAGACATATTCTGCTATCCACGGAC<br>TGTTGCCTGTGTCGGTGGCTACAATACGTGAGTCAGAAGGGCTGACGGTGGTG<br>GTTCCCAAGGAAAAGGTCGACGAGTATCTGTCTGACTCGTCATTGCCGCCTTT<br>GGAGTACGACTCCAACTATGAGTGTGCTTGGATCACTTTGACGATACATTCTT<br>CGTTGGAGGCTGTGGGTCTGACAGCTGCGTTTTCGGCGCGGTTGGCCGACAAC<br>AATATCAGCTGCAACGTCATTGCTGGCTTTCATCATGATCACATTTTTGTCGG<br>CAAAGGCGACGCCCAGAGAGCCATTGACGTTCTTTCTAATTTGGACCGATAGC<br>CGTATAGTCCAGTCTATCTATAAGTTCAACTAACTCGTAACTATTACCATAAC<br>ATATACTTCACTGCCCCAGATAAGGTTCCGATAAAAAGTTCTGCAGACTAAAT<br>TTATTTCAGTCTCCTCTTCACCACCAAAATGCCCTCCTACGAAGCTCGAGCTA<br>ACGTCCACAAGTCCGCCTTTGCCGCTCGAGTGCTCAAGCTCGTGGCAGCCAAG<br>AAAACCAACCTGTGTGCTTCTCTGGATGTTACCACCACCAAGGGGCCGCTCGA<br>GCATGCATCTAGAGGGCCCAATTCGCCCTATAGTGAGTCGTATTACAATTCAC<br>TGGCCGTCGTTTTACAACGTCGTGACTGGGAAAACCCTGGCGTTACCCAACTT<br>AATCGCCTTGCAGCACATCCCCCTTTCGCCAGCTGGCGTAATAGCGAAGAGGC<br>CCGCACCGATCGCCCTTCCCAACAGTTGCGCAGCCTGAATGGCGAATGGACGC<br>GCCCTGTAGCGGCGCATTAAGCGCGGCGGGTGTGGTGGTTACGCGCAGCGTGA<br>CCGCTACACTTGCCAGCGCCCTAGCGCCCGCTCCTTTCGCTTTCTTCCCTTCC<br>TTTCTCGCCACGTTCGCCGGCTTTCCCCGTCAAGCTCTAAATCGGGGGCTCCC<br>TTTAGGGTTCCGATTTAGTGCTTTACGGCACCTCGACCCCAAAAAACTTGATT<br>AGGGTGATGGTTCACGTAGTGGGCCATCGCCCTGATAGACGGTTTTTCGCCCT<br>TTGACGTTGGAGTCCACGTTCTTTAATAGTGGACTCTTGTTCCAAACTGGAAC<br>AACACTCAACCCTATCTCGGTCTATTCTTTTGATTTATAAGGGATTTTGCCGA<br>TTTCGGCCTATTGGTTAAAAAATGAGCTGATTTAACAAAAATTTAACGCGAAT<br>TTTAACAAAATTCAGGGCGCAAGGGCTGCTAAAGGAAGCGGAACACGTAGAAA<br>GCCAGTCCGCAGAAACGGTGCTGACCCCGGATGAATGTCAGCTACTGGGCTAT<br>CTGGACAAGGGAAAACGCAAGCGCAAAGAGAAAGCAGGTAGCTTGCAGTGGGC<br>TTACATGGCGATAGCTAGACTGGGCGGTTTTATGGACAGCAAGCGAACCGGAA<br>TTGCCAGCTGGGGCGCCCTCTGGTAAGGTTGGGAAGCCCTGCAAAGTAAACTG<br>GATGGCTTTCTTGCCGCCAAGGATCTGATGGCGCAGGGGATCAAGATCTGATC<br>AAGAGACAGGATGAGGATCGTTTCGCATGATTGAACAAGATGGATTGCACGCA<br>GGTTCTCCGGCCGCTTGGGTGGAGAGGCTATTCGGCTATGACTGGGCACAACA<br>GACAATCGGCTGCTCTGATGCCGCCGTGTTCCGGCTGTCAGCGCAGGGGCGCC<br>CGGTTCTTTTTGTCAAGACCGACCTGTCCGGTGCCCTGAATGAACTGCAGGAC<br>GAGGCAGCGCGGCTATCGTGGCTGGCCACGACGGGCGTTCCTTGCGCAGCTGT<br>GCTCGACGTTGTCACTGAAGCGGGAAGGGACTGGCTGCTATTGGGCGAAGTGC<br>CGGGGCAGGATCTCCTGTCATCCCACCTTGCTCCTGCCGAGAAAGTATCCATC<br>ATGGCTGATGCAATGCGGCGGCTGCATACGCTTGATCCGGCTACCTGCCCATT<br>CGACCACCAAGCGAAACATCGCATCGAGCGAGCACGTACTCGGATGGAAGCCG<br>GTCTTGTCGATCAGGATGATCTGGACGAAGAGCATCAGGGGCTCGCGCCAGCC<br>GAACTGTTCGCCAGGCTCAAGGCGCGCATGCCCGACGGCGAGGATCTCGTCGT | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | GACCCATGGCGATGCCTGCTTGCCGAATATCATGGTGGAAAATGGCCGCTTTT<br>CTGGATTCATCGACTGTGGCCGGCTGGGTGTGGCGGACCGCTATCAGGACATA<br>GCGTTGGCTACCCGTGATATTGCTGAAGAGCTTGGCGGCGAATGGGCTGACCG<br>CTTCCTCGTGCTTTACGGTATCGCCGCTCCCGATTCGCAGCGCATCGCCTTCT<br>ATCGCCTTCTTGACGAGTTCTTCTGAATTGAAAAAGGAAGAGTATGAGTATTC<br>AACATTTCCGTGTCGCCCTTATTCCCTTTTTTGCGGCATTTTGCCTTCCTGTT<br>TTTGCTCACCCAGAAACGCTGGTGAAAGTAAAAGATGCTGAAGATCAGTTGGG<br>TGCACGAGTGGGTTACATCGAACTGGATCTCAACAGCGGTAAGATCCTTGAGA<br>GTTTTCGCCCCGAAGAACGTTTTCCAATGATGAGCACTTTTAAAGTTCTGCTA<br>TGTGGCGCGGTATTATCCCGTATTGACGCCGGGCAAGAGCAACTCGGTCGCCG<br>CATACACTATTCTCAGAATGACTTGGTTGAGTACTCACCAGTCACAGAAAAGC<br>ATCTTACGGATGGCATGACAGTAAGAGAATTATGCAGTGCTGCCATAACCATG<br>AGTGATAACACTGCGGCCAACTTACTTCTGACAACGATCGGAGGACCGAAGGA<br>GCTAACCGCTTTTTTGCACAACATGGGGGATCATGTAACTCGCCTTGATCGTT<br>GGGAACCGGAGCTGAATGAAGCCATACCAAACGACGAGCGTGACACCACGATG<br>CCTGTAGCAATGGCAACAACGTTGCGCAAACTATTAACTGGCGAACTACTTAC<br>TCTAGCTTCCCGGCAACAATTAATAGACTGGATGGAGGCGGATAAAGTTGCAG<br>GACCACTTCTGCGCTCGGCCCTTCCGGCTGGCTGGTTTATTGCTGATAAATCT<br>GGAGCCGGTGAGCGTGGGTCTCGCGGTATCATTGCAGCACTGGGGCCAGATGG<br>TAAGCCCTCCCGTATCGTAGTTATCTACACGACGGGGAGTCAGGCAACTATGG<br>ATGAACGAAATAGACAGATCGCTGAGATAGGTGCCTCACTGATTAAGCATTGG<br>TAACTGTCAGACCAAGTTTACTCATATATACTTTAGATTGATTTAAAACTTCA<br>TTTTTAATTTAAAAGGATCTAGGTGAAGATCCTTTTTGATAATCTCATGACCA<br>AAATCCCTTAACGTGAGTTTTCGTTCCACTGAGCGTCAGACCCCGTAGAAAAG<br>ATCAAAGGATCTTCTTGAGATCCTTTTTTTCTGCGCGTAATCTGCTGCTTGCA<br>AACAAAAAAACCACCGCTACCAGCGGTGGTTTGTTTGCCGGATCAAGAGCTAC<br>CAACTCTTTTTCCGAAGGTAACTGGCTTCAGCAGAGCGCAGATACCAAATACT<br>GTTCTTCTAGTGTAGCCGTAGTTAGGCCACCACTTCAAGAACTCTGTAGCACC<br>GCCTACATACCTCGCTCTGCTAATCCTGTTACCAGTGGCTGCTGCCAGTGGCG<br>ATAAGTCGTGTCTTACCGGGTTGGACTCAAGACGATAGTTACCGGATAAGGCG<br>CAGCGGTCGGGCTGAACGGGGGGTTCGTGCACACAGCCCAGCTTGGAGCGAAC<br>GACCTACACCGAACTGAGATACCTACAGCGTGAGCTATGAGAAAGCGCCACGC<br>TTCCCGAAGGGAGAAAGGCGGACAGGTATCCGGTAAGCGGCAGGGTCGGAACA<br>GGAGAGCGCACGAGGGAGCTTCCAGGGGGAAACGCCTGGTATCTTTATAGTCC<br>TGTCGGGTTTCGCCACCTCTGACTTGAGCGTCGATTTTTGTGATGCTCGTCAG<br>GGGGGCGGAGCCTATGGAAAAACGCCAGCAACGCGGCCTTTTTACGGTTCCTG<br>GCCTTTTGCTGGCCTTTTGCTCACATGTTCTTTCCTGCGTTATCCCCTGATTC<br>TGTGGATAACCGTATTACCGCCTTTGAGTGAGCTGATACCGCTCGCCGCAGCC<br>GAACGACCGAGCGCAGCGAGTCAGTGAGCGAGG | |
| MB9894 | AAGCGGAAGAGCGCCCAATACGCAAACCGCCTCTCCCCGCGCGTTGGCCGATT<br>CATTAATGCAGCTGGCACGACAGGTTTCCCGACTGGAAAGCGGGCAGTGAGCG<br>CAACGCAATTAATGTGAGTTAGCTCACTCATTAGGCACCCCAGGCTTTACACT<br>TTATGCTTCCGGCTCGTATGTTGTGTGGAATTGTGAGCGGATAACAATTTCAC<br>ACAGGAAACAGCTATGACCATGATTACGCCAAGCTTGGTACCAGAGACGGGTT<br>GGCGGCGTATTTGTGTCCCAAAAAACAGCCCCAATTGCCCCAATTGACCCCAA<br>ATTGACCCAGTAGCGGGCCCAACCCCGGCGAGAGCCCCCTTCACCCCACATAT<br>CAAACCTCCCCCGGTTCCCACACTTGCCGTTAAGGGCGTAGGGTACTGCAGTC<br>TGGAATCTACGCTTGTTCAGACTTTGTACTAGTTTCTTTGTCTGGCCATCCGG<br>GTAACCCATGCCGGACGCAAAATAGACTACTGAAAATTTTTTTGCTTTGTGGT<br>TGGGACTTTAGCCAAGGGTATAAAAGACCACCGTCCCCGAATTACCTTTCCTC<br>TTCTTTTCTCTCTCTCCTTGTCAACTCACACCCGAAATCGTTAAGCATTTCCT<br>TCTGAGTATAAGAATCATTCGCTAGCCCACAAAAATGACCCGATCCAAGTTCA<br>CCGAGTACAAGCAGGTTCTCCGAAACTCTTGTGTTGGCAAGCCCCAGTACACT<br>GAGAAGGATTACCCCGATCTCGACGGAAAGAACTTTCTCGTCACTGGTGCTAC<br>TGGTGGAGTTGGTCTGGAGGCCACTAAGCTGCTCCTTGAGAAGAAGTCTCACG<br>TTATTATGGTTGGCCGATCTAAGACTAAGTCTCAGTCTACCCTTGACGAGCTT<br>CAGAAGACTTACTCTCACGGTACTTTCGATTTCGTTGAGGCTGATCTCTCTGA<br>CCTTACCACTGTTGAGCGAGCCGGAGAGTACATTCGATCTAAGTACACTACCC<br>TTGACGGTGCCATTCTTAACGCTGGAGTCATGGCTCCCCCCTACTCTCTCACT<br>CCCCAGGGTCACGAGTCTCAGTGGGGTATTAACGTTGTTGCTCACTTTCTCCT<br>GTCTAAGTACATCTCTCCTGCTCTGATTTCTGCTGCTCAGACTGCCCCCAAGG<br>ACACCGTTCGACTTGTTTGGGTGTCTTCTTCTGTCGTTGCCATGTCTCCTTAC<br>GAGGGAGGTATTAAGTTTGACGATATTAACCACTCTAAGGTCAAGAACCCTTC<br>TCCTTGGACCCTTTACTCTCAGTCTAAGATTGGTGATGCTTACCTGGCTTACC<br>TTTGGTCTAAGCACCACCCCGATTCTGGAGTCCTTTCTGTCTCTCTGGACCCC<br>GGTAACCTGGCTTCTGATCTCTCTCGACACACTTCTTGGCTTTCTTCTATTAA<br>GAACTACGTTCTTTACCCTCCCAAGTACGGTGCCTACACTGAGCTGTCTGCTC<br>TTCTCAACCCTTCCGTTAAGAACAACGAGCACCTTATTCCCTGGGGTATTGAG<br>GGACACCTTCGACAGGATGTCGACGATGGTCGACGAGGAAAGGACGGAGAGGA<br>GCTCTGGCAGGGTCTTAACAAGGATGTCGAGGGTTTCTTTAAGGAGGAGTAAA | 11 |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CGCGTGCAATTAACAGATAGTTTGCCGGTGATAATTCTCTTAACCTCCCACAC<br>TCCTTTGACATAACGATTTATGTAACGAAACTGAAATTTGACCAGATATTGTT<br>GTAAATAGAAAATCTGGCTTGTAGGTGGCAAACTAGTGGTGTGTTCTGTGGAG<br>CATTCTCACTTTTGGTAAACGACATTGCTTCAAGTGCAGCGGAATCAAAAAGT<br>ATAAAGTGGGCAGCGAGTATACCTGTACAGACTGTAGGCGATAACTCAATCCA<br>ATTACCCCCCACAACATGACTGGCCAAACTGATCTCAAGACTTTATTGAAATC<br>AGCAACACCGATTCTCAATGAAGGCACATACTTCTTCTGCAACATTCACTTGA<br>CGCCTAAAGTTGGTGAGAAATGGACCGACAAGACATATTCTGCTATCCACGGA<br>CTGTTGCCTGTGTCGGTGGCTACAATACGTGAGTCAGAAGGGCTGACGGTGGT<br>GGTTCCCAAGGAAAAGGTCGACGAGTATCTGTCTGACTCGTCATTGCCGCCTT<br>TGGAGTACGACTCCAACTATGAGTGTGCTTGGATCACTTTGACGATACATTCT<br>TCGTTGGAGGCTGTGGGTCTGACAGCTGCGTTTTCGGCGCGGTTGGCCGACAA<br>CAATATCAGCTGCAACGTCATTGCTGGCTTTCATCATGATCACATTTTTGTCG<br>GCAAAGGCGACGCCCAGAGAGCCATTGACGTTCTTTCTAATTTGGACCGATAG<br>CCGTATAGTCCAGTCTATCTATAAGTTCAACTAACTCGTAACTATTACCATAA<br>CATATACTTCACTGCCCCAGATAAGGTTCCGATAAAAAGTTCTGCAGACTAAA<br>TTTATTTCAGTCTCCTCTTCACCACCAAAATGCCCTCCTACGAAGCTCGAGCT<br>AACGTCCACAAGTCCGCCTTTGCCGCTCGAGTGCTCAAGCTCGTGGCAGCCAA<br>GAAAACCAACCTGTGTGCTTCTCTGGATGTTACCACCACCAAGGAGCTCATTG<br>AGCTTGCCGATAAGGTCGGACCTTATGTGTGCATGATCAAGACCCATATCGAC<br>ATCATTGACGACTTCACCTACGCCGGCACTGTGCTCCCCCTCAAGGAACTTGC<br>TCTTAAGCACGGTTTCTTCCTGTTCGAGGACAGAAAGTTCGCAGATATTGGCA<br>ACACTGTCAAGCACCAGTACAAGAACGGTGTCTACCGAATCGCCGAGTGGTCC<br>GATATCACCAACGCCCACGGTGTACCCGGAACCGGAATCATTGCTGGCCTGCG<br>AGCTGGTGCCGAGGAAACTGTCTCTGAACAGAAGAAGGAGGACGTCTCTGACT<br>ACGAGAACTCCCAGTACAAGGAGTTCCTGGTCCCCTCTCCCAACGAGAAGCTG<br>GCCAGAGGTCTGCTCATGCTGGCCGAGCTGTCTTGCAAGGGCTCTCTGGCCAC<br>TGGCGAGTACTCCAAGCAGACCATTGAGCTTGCCCGATCCGACCCCGAGTTTG<br>TGGTTGGCTTCATTGCCCAGAACCGACCTAAGGGCGACTCTGAGGACTGGCTT<br>ATTCTGACCCCCGGGGTGGGTCTTGACGACAAGGGAGACGCTCTCGGACAGCA<br>GTACCGAACTGTTGAGGATGTCATGTCTACCGGAACGGATATCATAATTGTCG<br>GCCGAGGTCTGTACGGCCAGAACCGAGATCCTATTGAGGAGGCCAAGCGATAC<br>CAGAAGGCTGGCTGGGAGGCTTACCAGAAGATTAACTGTTAGAGGTTAGACTA<br>TGGATATGTAATTTAACTGTGTATATAGAGAGCGTGCAAGTATGGAGCGCTTG<br>TTCAGCTTGTATGATGGTCAGACGACCTGTCTGATCGAGTATGTATGATACTG<br>CACAACCTGTGTATCCGCATGATCTGTCCAATGGGGCATGTTGTTGTGTTTCT<br>CGATACGGAGATGCTGGGTACAAGTAGCTAATACGATTGAACTACTTATACTT<br>ATATGAGGCTTGAAGAAAGCTGACTTGTGTATGACTTATTCTCAACTACATCC<br>CCAGTCACAATACCACCACTGCACTACCACTACACCTCGAGCATGCATCTAGT<br>GGTGTGTTCTGTGGAGCATTCTCACTTTTGGTAAACGACATTGCTTCAAGTGC<br>AGCGGAATCAAAAAGTATAAAGTGGGCAGCGAGTATACCTGTACAGACTGTAG<br>GCGATAACTCAATCCAATTACCCCCCACAACATGACTGGCCAAACTGATCTCA<br>AGACTTTATTGAAATCAGCAACACCGATTCTCAATGAAGGCACATACTTCTTC<br>TGCAACATTCACTTGACGCCTAAAGTTGGTGAGAAATGGACCGACAAGACATA<br>TTCTGCTATCCACGGACTGTTGCCTGTGTCGGTGGCTACAATACGTGAGTCAG<br>AAGGGCTGACGGTGGTGGTTCCCAAGGAAAAGGTCGACGAGTATCTGTCTGAC<br>TCGTCATTGCCGCCTTTGGAGTACGACTCCAACTATGAGTGTGCTTGGATCAC<br>TTTGACGATACATTCTTCGTTGGAGGCTGTGGGTCTGACAGCTGCGTTTTCGG<br>CGCGGTTGGCCGACAACAATATCAGCTGCAACGTCATTGCTGGCTTTCATCAT<br>GATCACATTTTTGTCGGCAAAGGCGACGCCCAGAGAGCCATTGACGTTCTTTC<br>TAATTTGGACCGATAGCCGTATAGTCCAGTCTATCTATAAGTTCAACTAACTC<br>GTAACTATTACCATAACATATACTTCACTGCCCCAGATAAGGTTCCGATAAAA<br>AGTTCTGCAGACTAAATTTATTTCAGTCTCCTCTTCACCACCAAAATGCCCTC<br>CTACGAAGCTCGAGCTAACGTCCACAAGTCCGCCTTTGCCGCTCGAGTGCTCA<br>AGCTCGTGGCAGCCAAGAAAACCAACCTGTGTGCTTCTCTGGATGTTACCACC<br>ACCAAGGGGCCGCTCGAGCATGCATCTAGAGGGCCCAATTCGCCCTATAGTGA<br>GTCGTATTACAATTCACTGGCCGTCGTTTTACAACGTCGTGACTGGGAAAACC<br>CTGGCGTTACCCAACTTAATCGCCTTGCAGCACATCCCCCTTTCGCCAGCTGG<br>CGTAATAGCGAAGAGGCCCGCACCGATCGCCCTTCCCAACAGTTGCGCAGCCT<br>GAATGGCGAATGGACGCGCCCTGTAGCGGCGCATTAAGCGCGGCGGGTGTGGT<br>GGTTACGCGCAGCGTGACCGCTACACTTGCCAGCGCCCTAGCGCCCGCTCCTT<br>TCGCTTTCTTCCCTTCCTTTCTCGCCACGTTCGCCGGCTTTCCCCGTCAAGCT<br>CTAAATCGGGGGCTCCCTTTAGGGTTCCGATTTAGTGCTTTACGGCACCTCGA<br>CCCCAAAAAACTTGATTAGGGTGATGGTTCACGTAGTGGGCCATCGCCCTGAT<br>AGACGGTTTTTCGCCCTTTGACGTTGGAGTCCACGTTCTTTAATAGTGGACTC<br>TTGTTCCAAACTGGAACAACACTCAACCCTATCTCGGTCTATTCTTTTGATTT<br>ATAAGGGATTTTGCCGATTTCGGCCTATTGGTTAAAAAATGAGCTGATTTAAC<br>AAAAATTTAACGCGAATTTTAACAAAATTCAGGGCGCAAGGGCTGCTAAAGGA<br>AGCGGAACACGTAGAAAGCCAGTCCGCAGAAACGGTGCTGACCCCGGATGAAT<br>GTCAGCTACTGGGCTATCTGGACAAGGGAAAACGCAAGCGCAAAGAGAAAGCA<br>GGTAGCTTGCAGTGGGCTTACATGGCGATAGCTAGACTGGGCGGTTTTATGGA | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CAGCAAGCGAACCGGAATTGCCAGCTGGGGCGCCCTCTGGTAAGGTTGGGAAG<br>CCCTGCAAAGTAAACTGGATGGCTTTCTTGCCGCCAAGGATCTGATGGCGCAG<br>GGGATCAAGATCTGATCAAGAGACAGGATGAGGATCGTTTCGCATGATTGAAC<br>AAGATGGATTGCACGCAGGTTCTCCGGCCGCTTGGGTGGAGAGGCTATTCGGC<br>TATGACTGGGCACAACAGACAATCGGCTGCTCTGATGCCGCCGTGTTCCGGCT<br>GTCAGCGCAGGGGCGCCCGGTTCTTTTTGTCAAGACCGACCTGTCCGGTGCCC<br>TGAATGAACTGCAGGACGAGGCAGCGCGGCTATCGTGGCTGGCCACGACGGGC<br>GTTCCTTGCGCAGCTGTGCTCGACGTTGTCACTGAAGCGGGAAGGGACTGGCT<br>GCTATTGGGCGAAGTGCCGGGGCAGGATCTCCTGTCATCCCACCTTGCTCCTG<br>CCGAGAAAGTATCCATCATGGCTGATGCAATGCGGCGGCTGCATACGCTTGAT<br>CCGGCTACCTGCCCATTCGACCACCAAGCGAAACATCGCATCGAGCGAGCACG<br>TACTCGGATGGAAGCCGGTCTTGTCGATCAGGATGATCTGGACGAAGAGCATC<br>AGGGGCTCGCGCCAGCCGAACTGTTCGCCAGGCTCAAGGCGCGCATGCCCGAC<br>GGCGAGGATCTCGTCGTGACCCATGGCGATGCCTGCTTGCCGAATATCATGGT<br>GGAAAATGGCCGCTTTTCTGGATTCATCGACTGTGGCCGGCTGGGTGTGGCGG<br>ACCGCTATCAGGACATAGCGTTGGCTACCCGTGATATTGCTGAAGAGCTTGGC<br>GGCGAATGGGCTGACCGCTTCCTCGTGCTTTACGGTATCGCCGCTCCCGATTC<br>GCAGCGCATCGCCTTCTATCGCCTTCTTGACGAGTTCTTCTGAATTGAAAAAG<br>GAAGAGTATGAGTATTCAACATTTCCGTGTCGCCCTTATTCCCTTTTTTGCGG<br>CATTTTGCCTTCCTGTTTTTGCTCACCCAGAAACGCTGGTGAAAGTAAAAGAT<br>GCTGAAGATCAGTTGGGTGCACGAGTGGGTTACATCGAACTGGATCTCAACAG<br>CGGTAAGATCCTTGAGAGTTTTCGCCCCGAAGAACGTTTTCCAATGATGAGCA<br>CTTTTAAAGTTCTGCTATGTGGCGCGGTATTATCCCGTATTGACGCCGGGCAA<br>GAGCAACTCGGTCGCCGCATACACTATTCTCAGAATGACTTGGTTGAGTACTC<br>ACCAGTCACAGAAAAGCATCTTACGGATGGCATGACAGTAAGAGAATTATGCA<br>GTGCTGCCATAACCATGAGTGATAACACTGCGGCCAACTTACTTCTGACAACG<br>ATCGGAGGACCGAAGGAGCTAACCGCTTTTTTGCACAACATGGGGGATCATGT<br>AACTCGCCTTGATCGTTGGGAACCGGAGCTGAATGAAGCCATACCAAACGACG<br>AGCGTGACACCACGATGCCTGTAGCAATGGCAACAACGTTGCGCAAACTATTA<br>ACTGGCGAACTACTTACTCTAGCTTCCCGGCAACAATTAATAGACTGGATGGA<br>GGCGGATAAAGTTGCAGGACCACTTCTGCGCTCGGCCCTTCCGGCTGGCTGGT<br>TTATTGCTGATAAATCTGGAGCCGGTGAGCGTGGGTCTCGCGGTATCATTGCA<br>GCACTGGGGCCAGATGGTAAGCCCTCCCGTATCGTAGTTATCTACACGACGGG<br>GAGTCAGGCAACTATGGATGAACGAAATAGACAGATCGCTGAGATAGGTGCCT<br>CACTGATTAAGCATTGGTAACTGTCAGACCAAGTTTACTCATATATACTTTAG<br>ATTGATTTAAAACTTCATTTTTAATTTAAAAGGATCTAGGTGAAGATCCTTTT<br>TGATAATCTCATGACCAAAATCCCTTAACGTGAGTTTTCGTTCCACTGAGCGT<br>CAGACCCCGTAGAAAAGATCAAAGGATCTTCTTGAGATCCTTTTTTTCTGCGC<br>GTAATCTGCTGCTTGCAAACAAAAAAACCACCGCTACCAGCGGTGGTTTGTTT<br>GCCGGATCAAGAGCTACCAACTCTTTTTCCGAAGGTAACTGGCTTCAGCAGAG<br>CGCAGATACCAAATACTGTTCTTCTAGTGTAGCCGTAGTTAGGCCACCACTTC<br>AAGAACTCTGTAGCACCGCCTACATACCTCGCTCTGCTAATCCTGTTACCAGT<br>GGCTGCTGCCAGTGGCGATAAGTCGTGTCTTACCGGGTTGGACTCAAGACGAT<br>AGTTACCGGATAAGGCGCAGCGGTCGGGCTGAACGGGGGGTTCGTGCACACAG<br>CCCAGCTTGGAGCGAACGACCTACACCGAACTGAGATACCTACAGCGTGAGCT<br>ATGAGAAAGCGCCACGCTTCCCGAAGGGAGAAAGGCGGACAGGTATCCGGTAA<br>GCGGCAGGGTCGGAACAGGAGAGCGCACGAGGGAGCTTCCAGGGGGAAACGCC<br>TGGTATCTTTATAGTCCTGTCGGGTTTCGCCACCTCTGACTTGAGCGTCGATT<br>TTTGTGATGCTCGTCAGGGGGGCGGAGCCTATGGAAAAACGCCAGCAACGCGG<br>CCTTTTTACGGTTCCTGGCCTTTTGCTGGCCTTTTGCTCACATGTTCTTTCCT<br>GCGTTATCCCCTGATTCTGTGGATAACCGTATTACCGCCTTTGAGTGAGCTGA<br>TACCGCTCGCCGCAGCCGAACGACCGAGCGCAGCGAGTCAGTGAGCGAGG | |
| MB9997 | AAGCGGAAGAGCGCCCAATACGCAAACCGCCTCTCCCCGCGCGTTGGCCGATT<br>CATTAATGCAGCTGGCACGACAGGTTTCCCGACTGGAAAGCGGGCAGTGAGCG<br>CAACGCAATTAATGTGAGTTAGCTCACTCATTAGGCACCCCAGGCTTTACACT<br>TTATGCTTCCGGCTCGTATGTTGTGTGGAATTGTGAGCGGATAACAATTTCAC<br>ACAGGAAACAGCTATGACCATGATTACGCCAAGCTTGGTACCAGAGACGGGTT<br>GGCGGCGTATTTGTGTCCCAAAAAACAGCCCCAATTGCCCCAATTGACCCCAA<br>ATTGACCCAGTAGCGGGCCCAACCCCGGCGAGAGCCCCCTTCACCCCACATAT<br>CAAACCTCCCCCGGTTCCCACACTTGCCGTTAAGGGCGTAGGGTACTGCAGTC<br>TGGAATCTACGCTTGTTCAGACTTTGTACTAGTTTCTTTGTCTGGCCATCCGG<br>GTAACCCATGCCGGACGCAAAATAGACTACTGAAAATTTTTTTGCTTTGTGGT<br>TGGGACTTTAGCCAAGGGTATAAAAGACCACCGTCCCCGAATTACCTTTCCTC<br>TTCTTTTCTCTCTCTCCTTGTCAACTCACACCCGAAATCGTTAAGCATTTCCT<br>TCTGAGTATAAGAATCATTCGCTAGCCCACAAAAATGGTTAACGTTGCTTACG<br>AGTGGCTTCGAGACTGCTGGCCCCCTAAGCCTGAGTTCCTCCCTAAGGATTAC<br>CCTGACCTCACCGGAAAGACCATCCTTATCACTGGTGCCAACACTGGTATTGG<br>TTTTGAGTCCGCTAAGGCTCTCCTCAAGAAGAACGCTACCGTTGTTTTTGCCA<br>ACCGATCCGAGGAGAAGACTAAGATCGCTATTGCCAAGATTCAGGCTGAGCTT<br>GGTGGTGATTCTTCTCAGCGATCTATTTTCGTCAAGACTGACCTTTCCGATCT | 12 |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | CTCTTCCATTAAGGGCACTGCTGAGGAGCTTAAGTCTAAGGGTATCACTAAGC<br>TCCACTACACCATTCTTAACGCTGGTGTTATGCAGCCTCCCAAGGGCTCCAAG<br>ACTAAGCAGGGTTTTGAGCTTCAGATTGGTACTAACGTTCTTGGCCACCAGCT<br>CCTCCAGAAGTTTCTCACTCCCCTTGTTCTCAACGCTGTTTCTTCTGATTTCA<br>CCCCTCGAGTTGTTTGGCTCGCCTCTGCTGCTCACCTTTCTTCCCCTCCCAAC<br>GGTGGTATTGATTGGGATTCCTTCCGAAACGCTGATTGGGCTGGTACTGTCTC<br>TGCTTACGGTCAGTCTAAGACTGGTAACATTTACCAGGCTTACATCTACGCTC<br>AGCAGCACAAGGATGTCATCTCTGTCTCTGCTCACCCCGGATACCTTGCTTCT<br>GATCTCACTCGAGCTTACAAGGGATACCTTCAGTACCTTATGAAGCTCCTTAT<br>GTCTCCTCCCGTTTACGGTTCTTACACTGAGCTTTTCGCTGCTCTTTCTCCCA<br>AGGTTACTCTCAAGGAGTCTGGTCGATACATTGGTCCTTGGGGTCAGTTCCGA<br>GAGCTTCGAGATGACGTTCAGGAGGGCCTTACCGATGGTACTGCTCAGAAGCT<br>CTGGGATTGGGCTGAGGCTGAGATTCGACCTTACACTTAAACGCGTGCAATTA<br>ACAGATAGTTTGCCGGTGATAATTCTCTTAACCTCCCACACTCCTTTGACATA<br>ACGATTTATGTAACGAAACTGAAATTTGACCAGATATTGTTGTAAATAGAAAA<br>TCTGGCTTGTAGGTGGCAAACTAGTGGTGTGTTCTGTGGAGCATTCTCACTTT<br>TGGTAAACGACATTGCTTCAAGTGCAGCGGAATCAAAAAGTATAAAGTGGGCA<br>GCGAGTATACCTGTACAGACTGTAGGCGATAACTCAATCCAATTACCCCCCAC<br>AACATGACTGGCCAAACTGATCTCAAGACTTTATTGAAATCAGCAACACCGAT<br>TCTCAATGAAGGCACATACTTCTTCTGCAACATTCACTTGACGCCTAAAGTTG<br>GTGAGAAATGGACCGACAAGACATATTCTGCTATCCACGGACTGTTGCCTGTG<br>TCGGTGGCTACAATACGTGAGTCAGAAGGGCTGACGGTGGTGGTTCCCAAGGA<br>AAAGGTCGACGAGTATCTGTCTGACTCGTCATTGCCGCCTTTGGAGTACGACT<br>CCAACTATGAGTGTGCTTGGATCACTTTGACGATACATTCTTCGTTGGAGGCT<br>GTGGGTCTGACAGCTGCGTTTTCGGCGCGGTTGGCCGACAACAATATCAGCTG<br>CAACGTCATTGCTGGCTTTCATCATGATCACATTTTTGTCGGCAAAGGCGACG<br>CCCAGAGAGCCATTGACGTTCTTTCTAATTTGGACCGATAGCCGTATAGTCCA<br>GTCTATCTATAAGTTCAACTAACTCGTAACTATTACCATAACATATACTTCAC<br>TGCCCCAGATAAGGTTCCGATAAAAAGTTCTGCAGACTAAATTTATTTCAGTC<br>TCCTCTTCACCACCAAAATGCCCTCCTACGAAGCTCGAGCTAACGTCCACAAG<br>TCCGCCTTTGCCGCTCGAGTGCTCAAGCTCGTGGCAGCCAAGAAAACCAACCT<br>GTGTGCTTCTCTGGATGTTACCACCACCAAGGAGCTCATTGAGCTTGCCGATA<br>AGGTCGGACCTTATGTGTGCATGATCAAGACCCATATCGACATCATTGACGAC<br>TTCACCTACGCCGGCACTGTGCTCCCCCTCAAGGAACTTGCTCTTAAGCACGG<br>TTTCTTCCTGTTCGAGGACAGAAAGTTCGCAGATATTGGCAACACTGTCAAGC<br>ACCAGTACAAGAACGGTGTCTACCGAATCGCCGAGTGGTCCGATATCACCAAC<br>GCCCACGGTGTACCCGGAACCGGAATCATTGCTGGCCTGCGAGCTGGTGCCGA<br>GGAAACTGTCTCTGAACAGAAGAAGGAGGACGTCTCTGACTACGAGAACTCCC<br>AGTACAAGGAGTTCCTGGTCCCCTCTCCCAACGAGAAGCTGGCCAGAGGTCTG<br>CTCATGCTGGCCGAGCTGTCTTGCAAGGGCTCTCTGGCCACTGGCGAGTACTC<br>CAAGCAGACCATTGAGCTTGCCCGATCCGACCCCGAGTTTGTGGTTGGCTTCA<br>TTGCCCAGAACCGACCTAAGGGCGACTCTGAGGACTGGCTTATTCTGACCCCC<br>GGGGTGGGTCTTGACGACAAGGGAGACGCTCTCGGACAGCAGTACCGAACTGT<br>TGAGGATGTCATGTCTACCGGAACGGATATCATAATTGTCGGCCGAGGTCTGT<br>ACGGCCAGAACCGAGATCCTATTGAGGAGGCCAAGCGATACCAGAAGGCTGGC<br>TGGGAGGCTTACCAGAAGATTAACTGTTAGAGGTTAGACTATGGATATGTAAT<br>TTAACTGTGTATATAGAGAGCGTGCAAGTATGGAGCGCTTGTTCAGCTTGTAT<br>GATGGTCAGACGACCTGTCTGATCGAGTATGTATGATACTGCACAACCTGTGT<br>ATCCGCATGATCTGTCCAATGGGGCATGTTGTTGTGTTTCTCGATACGGAGAT<br>GCTGGGTACAAGTAGCTAATACGATTGAACTACTTATACTTATATGAGGCTTG<br>AAGAAAGCTGACTTGTGTATGACTTATTCTCAACTACATCCCCAGTCACAATA<br>CCACCACTGCACTACCACTACACCTCGAGCATGCATCTAGTGGTGTGTTCTGT<br>GGAGCATTCTCACTTTTGGTAAACGACATTGCTTCAAGTGCAGCGGAATCAAA<br>AAGTATAAAGTGGGCAGCGAGTATACCTGTACAGACTGTAGGCGATAACTCAA<br>TCCAATTACCCCCCACAACATGACTGGCCAAACTGATCTCAAGACTTTATTGA<br>AATCAGCAACACCGATTCTCAATGAAGGCACATACTTCTTCTGCAACATTCAC<br>TTGACGCCTAAAGTTGGTGAGAAATGGACCGACAAGACATATTCTGCTATCCA<br>CGGACTGTTGCCTGTGTCGGTGGCTACAATACGTGAGTCAGAAGGGCTGACGG<br>TGGTGGTTCCCAAGGAAAAGGTCGACGAGTATCTGTCTGACTCGTCATTGCCG<br>CCTTTGGAGTACGACTCCAACTATGAGTGTGCTTGGATCACTTTGACGATACA<br>TTCTTCGTTGGAGGCTGTGGGTCTGACAGCTGCGTTTTCGGCGCGGTTGGCCG<br>ACAACAATATCAGCTGCAACGTCATTGCTGGCTTTCATCATGATCACATTTTT<br>GTCGGCAAAGGCGACGCCCAGAGAGCCATTGACGTTCTTTCTAATTTGGACCG<br>ATAGCCGTATAGTCCAGTCTATCTATAAGTTCAACTAACTCGTAACTATTACC<br>ATAACATATACTTCACTGCCCCAGATAAGGTTCCGATAAAAAGTTCTGCAGAC<br>TAAATTTATTTCAGTCTCCTCTTCACCACCAAAATGCCCTCCTACGAAGCTCG<br>AGCTAACGTCCACAAGTCCGCCTTTGCCGCTCGAGTGCTCAAGCTCGTGGCAG<br>CCAAGAAAACCAACCTGTGTGCTTCTCTGGATGTTACCACCACCAAGGGGCCG<br>CTCGAGCATGCATCTAGAGGGCCCAATTCGCCCTATAGTGAGTCGTATTACAA<br>TTCACTGGCCGTCGTTTTACAACGTCGTGACTGGGAAAACCCTGGCGTTACCC<br>AACTTAATCGCCTTGCAGCACATCCCCCTTTCGCCAGCTGGCGTAATAGCGAA | |

TABLE 6-continued list of sequences including protein and polynucleotide sequences. Nucleotide sequences with a "*" refer to codon-optimized sequences. "aa" refers to amino acids sequence, "nt" refers to nucleotide sequence. For more details, see text.

| Name | Sequence 5' to 3' | SEQ ID NO: |
|---|---|---|
| | GAGGCCCGCACCGATCGCCCTTCCCAACAGTTGCGCAGCCTGAATGGCGAATG<br>GACGCGCCCTGTAGCGGCGCATTAAGCGCGGCGGGTGTGGTGGTTACGCGCAG<br>CGTGACCGCTACACTTGCCAGCGCCCTAGCGCCCGCTCCTTTCGCTTTCTTCC<br>CTTCCTTTCTCGCCACGTTCGCCGGCTTTCCCCGTCAAGCTCTAAATCGGGGG<br>CTCCCTTTAGGGTTCCGATTTAGTGCTTTACGGCACCTCGACCCCAAAAAACT<br>TGATTAGGGTGATGGTTCACGTAGTGGGCCATCGCCCTGATAGACGGTTTTTC<br>GCCCTTTGACGTTGGAGTCCACGTTCTTTAATAGTGGACTCTTGTTCCAAACT<br>GGAACAACACTCAACCCTATCTCGGTCTATTCTTTTGATTTATAAGGGATTTT<br>GCCGATTTCGGCCTATTGGTTAAAAAATGAGCTGATTTAACAAAAATTTAACG<br>CGAATTTTAACAAAATTCAGGGCGCAAGGGCTGCTAAAGGAAGCGGAACACGT<br>AGAAAGCCAGTCCGCAGAAACGGTGCTGACCCCGGATGAATGTCAGCTACTGG<br>GCTATCTGGACAAGGGAAAACGCAAGCGCAAAGAGAAAGCAGGTAGCTTGCAG<br>TGGGCTTACATGGCGATAGCTAGACTGGGCGGTTTTATGGACAGCAAGCGAAC<br>CGGAATTGCCAGCTGGGGCGCCCTCTGGTAAGGTTGGGAAGCCCTGCAAAGTA<br>AACTGGATGGCTTTCTTGCCGCCAAGGATCTGATGGCGCAGGGGATCAAGATC<br>TGATCAAGAGACAGGATGAGGATCGTTTCGCATGATTGAACAAGATGGATTGC<br>ACGCAGGTTCTCCGGCCGCTTGGGTGGAGAGGCTATTCGGCTATGACTGGGCA<br>CAACAGACAATCGGCTGCTCTGATGCCGCCGTGTTCCGGCTGTCAGCGCAGGG<br>GCGCCCGGTTCTTTTTGTCAAGACCGACCTGTCCGGTGCCCTGAATGAACTGC<br>AGGACGAGGCAGCGCGGCTATCGTGGCTGGCCACGACGGGCGTTCCTTGCGCA<br>GCTGTGCTCGACGTTGTCACTGAAGCGGGAAGGGACTGGCTGCTATTGGGCGA<br>AGTGCCGGGGCAGGATCTCCTGTCATCCCACCTTGCTCCTGCCGAGAAAGTAT<br>CCATCATGGCTGATGCAATGCGGCGGCTGCATACGCTTGATCCGGCTACCTGC<br>CCATTCGACCACCAAGCGAAACATCGCATCGAGCGAGCACGTACTCGGATGGA<br>AGCCGGTCTTGTCGATCAGGATGATCTGGACGAAGAGCATCAGGGGCTCGCGC<br>CAGCCGAACTGTTCGCCAGGCTCAAGGCGCGCATGCCCGACGGCGAGGATCTC<br>GTCGTGACCCATGGCGATGCCTGCTTGCCGAATATCATGGTGGAAAATGGCCG<br>CTTTTCTGGATTCATCGACTGTGGCCGGCTGGGTGTGGCGGACCGCTATCAGG<br>ACATAGCGTTGGCTACCCGTGATATTGCTGAAGAGCTTGGCGGCGAATGGGCT<br>GACCGCTTCCTCGTGCTTTACGGTATCGCCGCTCCCGATTCGCAGCGCATCGC<br>CTTCTATCGCCTTCTTGACGAGTTCTTCTGAATTGAAAAAGGAAGAGTATGAG<br>TATTCAACATTTCCGTGTCGCCCTTATTCCCTTTTTTGCGGCATTTTGCCTTC<br>CTGTTTTTGCTCACCCAGAAACGCTGGTGAAAGTAAAAGATGCTGAAGATCAG<br>TTGGGTGCACGAGTGGGTTACATCGAACTGGATCTCAACAGCGGTAAGATCCT<br>TGAGAGTTTTCGCCCCGAAGAACGTTTTCCAATGATGAGCACTTTTAAAGTTC<br>TGCTATGTGGCGCGGTATTATCCCGTATTGACGCCGGGCAAGAGCAACTCGGT<br>CGCCGCATACACTATTCTCAGAATGACTTGGTTGAGTACTCACCAGTCACAGA<br>AAAGCATCTTACGGATGGCATGACAGTAAGAGAATTATGCAGTGCTGCCATAA<br>CCATGAGTGATAACACTGCGGCCAACTTACTTCTGACAACGATCGGAGGACCG<br>AAGGAGCTAACCGCTTTTTTGCACAACATGGGGGATCATGTAACTCGCCTTGA<br>TCGTTGGGAACCGGAGCTGAATGAAGCCATACCAAACGACGAGCGTGACACCA<br>CGATGCCTGTAGCAATGGCAACAACGTTGCGCAAACTATTAACTGGCGAACTA<br>CTTACTCTAGCTTCCCGGCAACAATTAATAGACTGGATGGAGGCGGATAAAGT<br>TGCAGGACCACTTCTGCGCTCGGCCCTTCCGGCTGGCTGGTTTATTGCTGATA<br>AATCTGGAGCCGGTGAGCGTGGGTCTCGCGGTATCATTGCAGCACTGGGGCCA<br>GATGGTAAGCCCTCCCGTATCGTAGTTATCTACACGACGGGGAGTCAGGCAAC<br>TATGGATGAACGAAATAGACAGATCGCTGAGATAGGTGCCTCACTGATTAAGC<br>ATTGGTAACTGTCAGACCAAGTTTACTCATATATACTTTAGATTGATTTAAAA<br>CTTCATTTTTAATTTAAAAGGATCTAGGTGAAGATCCTTTTTGATAATCTCAT<br>GACCAAAATCCCTTAACGTGAGTTTTCGTTCCACTGAGCGTCAGACCCCGTAG<br>AAAAGATCAAAGGATCTTCTTGAGATCCTTTTTTTCTGCGCGTAATCTGCTGC<br>TTGCAAACAAAAAAACCACCGCTACCAGCGGTGGTTTGTTTGCCGGATCAAGA<br>GCTACCAACTCTTTTTCCGAAGGTAACTGGCTTCAGCAGAGCGCAGATACCAA<br>ATACTGTTCTTCTAGTGTAGCCGTAGTTAGGCCACCACTTCAAGAACTCTGTA<br>GCACCGCCTACATACCTCGCTCTGCTAATCCTGTTACCAGTGGCTGCTGCCAG<br>TGGCGATAAGTCGTGTCTTACCGGGTTGGACTCAAGACGATAGTTACCGGATA<br>AGGCGCAGCGGTCGGGCTGAACGGGGGGTTCGTGCACACAGCCCAGCTTGGAG<br>CGAACGACCTACACCGAACTGAGATACCTACAGCGTGAGCTATGAGAAAGCGC<br>CACGCTTCCCGAAGGGAGAAAGGCGGACAGGTATCCGGTAAGCGGCAGGGTCG<br>GAACAGGAGAGCGCACGAGGGAGCTTCCAGGGGGAAACGCCTGGTATCTTTAT<br>AGTCCTGTCGGGTTTCGCCACCTCTGACTTGAGCGTCGATTTTTGTGATGCTC<br>GTCAGGGGGGCGGAGCCTATGGAAAAACGCCAGCAACGCGGCCTTTTTACGGT<br>TCCTGGCCTTTTGCTGGCCTTTTGCTCACATGTTCTTTCCTGCGTTATCCCCT<br>GATTCTGTGGATAACCGTATTACCGCCTTTGAGTGAGCTGATACCGCTCGCCG<br>CAGCCGAACGACCGAGCGCAGCGAGTCAGTGAGCGAGG | |

The invention claimed is:

1. A retinol-producing host cell expressing a retinol dehydrogenase 22 (RDH22) homolog with at least 95% identity to the polypeptide of SEQ ID NO:1 or 4, wherein the host cell has been transformed with a polynucleotide encoding said RDH22 homolog, said host cell further expressing polypeptides involved in enzymatic conversion of beta-carotene into retinal, said host cell being capable of producing a mix of retinoids comprising retinol, retinal and dihydroretinoids and wherein the percentage of dihydroretinoids in the mix of retinoids produced under suitable culture conditions is less than 10% based on total retinoids as compared to production of retinoids using a respective retinol-producing host cell not expressing a polypeptide with at least 95% identity to SEQ ID NO: 1 or 4.

2. The retinol-producing host cell according to claim 1, further expressing polypeptides involved in enzymatic conversion of retinol into retinyl acetate, wherein the percentage of retinyl acetate in said mix of retinoids is at least 80% based on total retinoids.

3. The retinol producing host cell according to claim 1 or claim 2, wherein the percentage of retinal in said mix is less than 8% based on total retinoids.

4. The retinol-producing host cell according to claim 3, wherein the percentage of retinal is reduced to less than 2% based on total retinoids.

5. The retinol producing host cell according to claim 1 or claim 2, wherein said mix of retinoids comprises trans and cis-isomers and wherein the percentage of trans-isomers is at least 80% based on total cis and trans-isomers in said mix.

6. The retinol-producing host cell according to claim 1 or claim 2, wherein the RDH22 homolog is obtained from Yarrowia or Wickerhamomyces.

7. The retinol-producing host cell according to claim 1 or claim 2, furthermore expressing a retinol dehydrogenase 12 (RDH12) homolog.

8. A process for the production of a retinoid-mix comprising retinol, retinal, retinyl acetate and dihydroretinoids, said process comprising cultivation of a retinol-producing host cell according to claim 1 or claim 2 under suitable culture conditions, wherein the host cell is cultivated in the presence of a lipophilic solvent.

9. The process of claim 8, wherein said retinoid mix comprises dihydroretinal, dihydroretinol and dihydroretinyl acetate, retinol, retinal, retinyl acetate, and wherein the percentage of dihydroretinoids based on total retinoids is less than 10%.

10. The process of claim 9, wherein the retinoids are accumulated in the lipophilic solvent and optionally extracted from the lipophilic solvent.

11. The process of claim 9, wherein the lipophilic solvent is selected from isoparaffins including mixtures of alkanes, cycloparaffin, isoalkanes, cycloalkanes, or dodecanes.

12. The process of claim 8, wherein the host cell is a fungal host cell.

13. The process according to claim 8 for production of a retinoid mix comprising retinyl acetate and dihydroretinoids, wherein the percentage of retinyl acetate is at least 80% and the percentage of dihydroretinoids is 2% or less based on total retinoids.

14. A process for reducing the percentage of dihydroretinoids in the fermentative production of retinoids comprising cultivation of a retinol-producing host cell according to claim 8 under suitable culture conditions comprising the presence of a lipophilic substance, wherein the reduction of dihydroretinoids is at least 80% as compared to a process using a respective retinol-producing host cell not expressing a polypeptide with at least 95% identity to SEQ ID NO: 1 or 4.

15. A retinol-producing host cell expressing a retinol dehydrogenase 22 (RDH22) homolog of SEQ ID NO: 1 or 4, wherein the host cell has been transformed with a polynucleotide encoding said RDH22 homolog, said host cell further expressing polypeptides involved in enzymatic conversion of beta-carotene into retinal said host cell capable of producing a mix of retinoids comprising retinol, retinal and dihydroretinoids and wherein the percentage of dihydroretinoids in the mix of retinoids produced under suitable culture conditions is less than 10% based on total retinoids and as compared to production of retinoids using a respective retinol-producing host cell not expressing a retinol dehydrogenase 22 (RDH22) homolog of SEQ ID NO:1 or 4.

* * * * *